(12) United States Patent
Yoshida et al.

(10) Patent No.: US 8,476,290 B2
(45) Date of Patent: Jul. 2, 2013

(54) COMPOUND HAVING SPIRO-BONDED CYCLIC GROUP AND USE THEREOF

(75) Inventors: Koji Yoshida, Osaka (JP); Hiroshi Ochiai, Osaka (JP); Kousuke Tani, Osaka (JP); Shiro Shibayama, Ibaraki (JP); Miki Kasano, Ibaraki (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 17 days.

(21) Appl. No.: 13/378,799

(22) PCT Filed: Jun. 15, 2010

(86) PCT No.: PCT/JP2010/060068
§ 371 (c)(1),
(2), (4) Date: Dec. 16, 2011

(87) PCT Pub. No.: WO2010/147094
PCT Pub. Date: Dec. 23, 2010

(65) Prior Publication Data
US 2012/0101280 A1 Apr. 26, 2012

(30) Foreign Application Priority Data
Jun. 16, 2009 (JP) .................................. 2009-143458

(51) Int. Cl.
*A61K 31/438* (2006.01)
*C07D 471/10* (2006.01)

(52) U.S. Cl.
USPC ............................................ 514/278; 546/16

(58) Field of Classification Search
USPC ............................................ 514/278; 546/16
See application file for complete search history.

(56) References Cited

U.S. PATENT DOCUMENTS

| | | |
|---|---|---|
| 2008/0009495 A1 | 1/2008 | Kokubo et al. |
| 2009/0118279 A1 | 5/2009 | Kokubo et al. |
| 2009/0169567 A1 | 7/2009 | Kokubo et al. |
| 2009/0192182 A1 | 7/2009 | Kusumi et al. |

FOREIGN PATENT DOCUMENTS

| | | |
|---|---|---|
| WO | WO 2006/022454 A1 | 3/2006 |
| WO | WO 2007/049771 A1 | 5/2007 |
| WO | WO 2007/058322 A1 | 5/2007 |
| WO | WO 2007/132846 A1 | 11/2007 |

OTHER PUBLICATIONS

International Search Report [PCT/ISA/210] issued by the International Searching Authority in International Application No. PCT/JP2010/060068 on Aug. 31, 2010.

*Primary Examiner* — Charanjit Aulakh
(74) *Attorney, Agent, or Firm* — Sughrue Mion, PLLC

(57) ABSTRACT

A compound represented by formula (I):

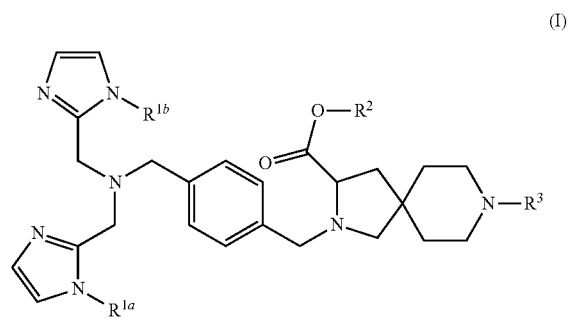

a salt thereof, an N-oxide thereof, or a solvate thereof (symbols in the formula are as described in the specification). The compounds of the present invention exhibit very low risk of side effects and also have persistent and strong antagonistic activity against CXCR4, and are therefore useful as pharmaceuticals, for example, as a preventive and/or therapeutic agent for inflammatory and immune diseases, infections (for example, HIV infection), diseases associated with HIV infection (for example, acquired immunodeficiency syndrome (AIDS)), cancer, cancer metastasis, psychoneurotic diseases and cardiovascular diseases (for example, retinopathy), metabolic diseases, cancerous diseases, or as an agent for regeneration therapy.

7 Claims, No Drawings

COMPOUND HAVING SPIRO-BONDED CYCLIC GROUP AND USE THEREOF

TECHNICAL FIELD

The present invention relates to compounds having a Spiro-bound cyclic group and use thereof.

More particularly, the present invention relates to (1) compound represented by formula (I):

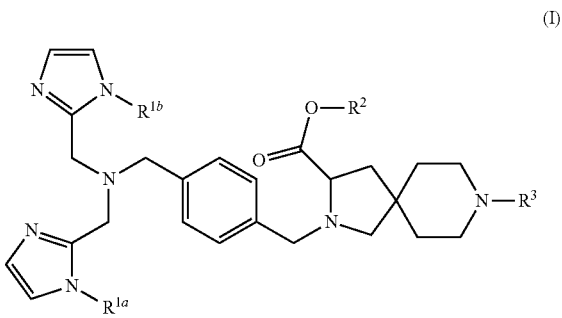

(wherein all symbols have the same meaning as described hereinafter), salts thereof, N-oxides thereof or solvates thereof, (2) use thereof, and (3) a method for producing the same.

BACKGROUND ART

Chemokine is known as a basic protein which has chemotaxis and an activating activity against endogenous leucocytes and also has strong heparin-binding abilities. It is now considered that chemokine is associated with not only control of infiltration of specific leucocytes upon inflammatory and immune responses, but also development, homing of lymphocytes under physiological conditions and migration of hemocyte precursor cells and somatic cells.

Differentiation, proliferation and cell death of blood cells are controlled by various cytokines. Inflammation occurs at a local region in a living body. Differentiation and maturation of lymphocytes, and the like are carried out at a specific site. More particularly, required various cells migrate and accumulate in the specific site and a sequence of inflammatory and immune responses arise. Thus, in addition to differentiation, proliferation and death of cells, cell migration is also an essential phenomenon to an immune system.

In the living body, migration of blood cells start with sifting hemopoiesis that started at AGM (Aorta Gonad Mesonephros) region via fetal liver to permanent hematopoiesis at bone marrow in a development course. Moreover, precursors of T cells and thymus dendritic cells migrate from fetal liver into bone marrow and then into the thymus gland. They differentiate under thymus environment. The T cells are subjected to clonal selection migrates into secondary lymphoid tissues, where they contribute to immune responses in periphery. Skin Langerhans cells that caught antigen, thereby undergone activation and differentiation migrate to T cell region in a topical lymph node, where they activate naive T cells therein as dendritic cells. The memory T cells again perform its homing into the lymph node via lymphatic and blood vessels. In addition, B cells, T cells in intestinal epithelia, γδT cells, NKT cells, and dendritic cells migrate from bone marrow not via thymus, differentiate and contribute to immune responses.

Chemokine is closely associated with such a migration of the various cells. For example, SDF-1 (Stromal cell derived factor-1) and its receptor, CXCR4 also act on various immune- and inflammatory reactions. For example, they have been reported to be associated with accumulation and activation of CD4+T cells in a synovial membrane from a human patient suffering from rheumatoid arthritis (J. Immunol., 165, 6590-6598 (2000)). In addition, in a CIA model mouse, CXCR4 inhibitor inhibited accumulation of leucocytes in a joint and dramatically reduced arthritis score (J. Immunol., 167, 4648-4692 (2001)). In a mouse OVA-induced airway hypersensitive model, an anti-CXCR4 antibody reduced the number of eosinophiles accumulating in pulmonary interstitial tissues and prevented airway hypersensitivity (J. Immunol., 165, 499-508 (2000)). In a mouse bleomycin-induced pulmonary disorder models, an anti-SDF-1 antibody inhibited invasion of fibrous cells to the lung and inhibited fibrosis of the lung (J. Clin. Invest., 114, 438-446 (2004)). In a mouse LPS-induced pneumonia model, it was observed that the number of neutrophils was increased with an increase in an SDF-1 concentration in an alveolar lavage fluid, and the number of neutrophils in the alveolar lavage fluid was prevented from being increased by administration of anti-SDF-1 antibody (J. Immunol., 178, 8148 (2007)). In a mouse retinopathy model, an anti-SDF-1 antibody inhibited vascular endothelial progenitor cell invasion to the retina and inhibited neovascularization at the retina (J. Clin. Invest., 115, 86-93 (2005)).

There has been reported that SDF-1 and its receptor, CXCR4 play an important role in maintaining hemopoietic stem cells in bone marrow (J. Exp. Med., 185, 111-120 (1997), Blood, 97, 3354-3360 (2001)). Accordingly, control of SDF-1 and CXCR4 is expected to modulate recruitment of hemopoietic stem cells to peripheral blood and are useful for peripheral blood stem cell transplantation and reproduction transplantation treatment.

SDF-1 and CXCR4 are associated with proliferation and infiltration of various cancer cells such as breast cancer, prostate cancer, ovarian cancer, medulloblastoma and the like (Nature, 410, 50 (2001), Cancer Res., 62, 1832 (2002), Cancer Res., 62, 5930 (2002), Proc. Nat. Acad. Sci. USA, 100, 13513 (2003)). In a model of transplanting a human breast cancer cell strain into a SCID mouse, an anti-CXCR4 antibody inhibited metastasis of breast cancer cells to lung (Nature, 410, 50-56 (2001)) and an anti-SDF-1 antibody inhibited neovascularization around cancer and inhibited proliferation of cancer cells (Cell, 121, 335 (2005)). In human ovarian epithelial tumor, highly expression of SDF-1 promotes accumulation of precursor cells of plasmacytoid dendritic cells which inhibit the act of T cells and suppresses tumor immune (Nat. Med., 12, 1339 (2001)). Moreover, SDF-1 is associated with proliferation and migration of non-Hodgkin's lymphoma cells, and in a model of transplanting a human non-Hodgkin's lymphoma cells into a NOD/SCID mouse, an anti-CXCR4 antibody inhibited proliferation of the tumor cells and improved mouse mortality (Cancer Res., 62, 3106-3112 (2002)). A low molecular weight CXCR4 antagonist increased apoptosis of medulloblastoma transplanted in the mouse skull and inhibited tumor proliferation (Proc. Nat. Acad. Sci. USA, 100, 13513 (2003)). In a lung metastasis model using malignant melanoma, the low molecular weight CXCR4 antagonist enhanced the antitumor effect of an immunostimulant and an anticancer drug (Mol Cancer Ther., 5, 2592 (2006)).

SDF-1 and CXCR4 play an important role for formation of hippocampus dentate gyrus granulocyte, that is essential for memory and learning and are associated with development of a disease associated with adult plasticity and pathology of hippocampus, for example Alzheimer's disease, stroke and epilepsy (Development, 129, 4249 (2002), Trends in Neurosci., 25, 548 (2002)).

SDF-1 and CXCR4 are essential for a function of self-reactive B cells associated with development of diabetes. In NOD mouse, an anti-SDF-1 antibody reduced blood glucose level and the number of mature IgM+B cells in a periphery tissue (Immunology, 107, 222 (2002)). In a human arteriosclerotic plaque, SDF-1 was highly expressed and activated blood platelets (Circ. Res., 86, 131 (2000)).

SDF-1 and CXCR4 are associated with residence of hemopoietic stem cells and hemopoietic precursor cells in bone marrow, and use of AMD3100 being CXCR4 antagonist in combination with G-CSF enabled an increase in the number of hemopoietic stem cells and hemopoietic precursor cells in peripheral blood (J. Exp. Med., 2001, 1307 (2005)). It is known that the number of neutrophils, lymphocytes and monocytes in peripheral blood are increased by administering a low molecular weight CXCR4 antagonist to human (Blood, 102, 2728-2730 (2003)). Therefore, the immunological enhancing effect is expected to the low molecular weight CXCR4 antagonist.

In addition, the results of SDF-1/CXCR4 knock-out mice showed that SDF-1 is essential for functions of central nervous tissue, heart and vessels of gastrointestinal tract in addition to lymphocytes (Nature, 382, 635 (1996), Nature, 393, 591 (1998), Nature, 393, 595 (1998)). Accordingly, it may be associated with a disease of these tissues.

Thus, chemokine receptors are expressed at various specific cells and at a specific time. They are largely associated with the control of inflammatory- and immune-responses through a mechanism by which their effector cells accumulate in a site where chemokine is produced.

Acquired immunodeficiency syndrome (also called AIDS) that caused by infection of human immunodeficiency virus (hereinafter abbreviated to HIV) is one of diseases for which therapies are the most eagerly desired lately. Once HIV infection has been established in a main target cell, CD4+cell, HIV repetitively proliferates in a patient's body and in the event deathly destroys T cells responsible for immunological functions. In this process, immunological functions are gradually deteriorated, various immunocompromised states become to develop such as fever, diarrhea and swelling of a lymph node, and various opportunistic infections such as carinii pneumonia are easily complicated. It is well known that such a state is the onset of AIDS and induces malignant tumors such as Kaposi's sarcoma and becomes severe.

Currently, there are tried various preventive and/or therapeutic treatments for AIDS as follows: for example, (1) inhibition of HIV proliferation by administration of reverse transcriptase inhibitors and protease inhibitors, and (2) prevention or alleviation of opportunistic infections by administration of an immunostimulant, etc.

HIV mainly infects helper T cells which play a key role in the immune system. Since 1985, it has been known that in this process HIV utilizes a membrane protein CD4 that is expressed on the membrane of T cells (Cell, 52, 631 (1985)). CD4 molecule consists of 433 amino acid residues and is expressed in macrophages, some B cells, vascular endothelial cells, Langerhans cells in skin tissues, dendritic cells located in lymphatic tissues, glia cells of central nervous system and the like in addition to mature helper T cells. However, as it becomes obvious that HIV infection cannot be established with only CD4 molecule, the possible presence of some factor that is responsible for infection of cell with HIV, other than CD4 molecule, has been suggested.

In 1996, a cell membrane protein called Fusin has been identified as a factor responsible for HIV infection other than a CD4 molecule (Science, 272, 872 (1996)). This Fusin molecule has been demonstrated to be a receptor for SDF-1, namely, CXCR4. In addition, it has been shown that SDF-1 specifically inhibits infection of T cell-directed (X4) HIV in vitro (Nature, 382, 829 (1996), Nature, 382, 833 (1996)). This may be considered that SDF-1 binds to CXCR4 prior to HIV, thereby taking away a scaffold for infecting a cell from HIV resulting in inhibition of HIV infection.

Also, at the same period, there has been found that another chemokine receptor CCR5, that is a receptor for RANTES, MIP-1α, and MIP-1β, is utilized at infection of macrophage-directed (R5) HIV (Science, 272, 1955 (1996)).

Namely, CXCR4 and CCR5 are expressed on a surface of host cells and both of them are employed as a coreceptor upon HIV infection.

Accordingly, those which can compete with HIV for CXCR4 and CCR5 or those which bind to a HIV virus and prevent for said virus from binding to CXCR4 and CCR5 may be a HIV infection inhibitor. In addition, there is a case where a low molecular weight compound discovered as a HIV infection inhibitor was showed to be indeed an antagonist of CXCR4 (Nat. Med., 4, 72 (1998)).

As described above, compounds having an antagonistic activity against CXCR4 are effective, such as, for prevention and/or the treatment of inflammatory and immune diseases, allergic diseases, infections (HIV infection, etc.), diseases associated with HIV infection (acquired immunodeficiency syndrome, etc.), cancer, cancer metastasis, psychoneurotic diseases, cardiovascular diseases, metabolic diseases and cancerous diseases, and are also useful for regeneration therapy.

Heretofore, the following compound has been reported. For example, it is disclosed that a compound represented by formula (R):

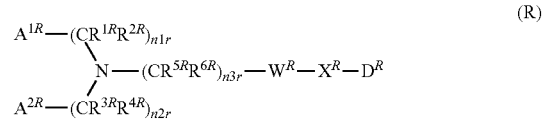

(wherein n1r, n2r and n3r represent 0 to 3; $R^{1R}$, $R^{2R}$, $R^{3R}$, $R^{4R}$, $R^{5R}$, $R^{6R}$ each independently represents a hydrogen atom or an optionally substituted C1-15 alkyl group, etc.; $A^{1R}$ and $A^{2R}$ each independently represents an optionally substituted monocyclic or polycyclic heterocyclic aromatic ring, etc.; $W^R$ represents an optionally substituted C1-15 alkylene group, etc.; $X^R$ represents O, $CH_2$ or $NR^{11R}$, etc.; $R^{11R}$ represents a hydrogen atom or an optionally substituted C1-15 alkyl group, etc.; $D^R$ represents -$Q^R$-$Y^R$—$B^R$, in which $Q^R$ represents a bond or —CO— when $X^R$ is $NR^{11R}$, $Y^R$ represents —$(CR^{18R}R^{19R})_{m3r}$—, $R^{18R}$ and $R^{19R}$ each independently represents a hydrogen atom or an optionally substituted C1-15 alkyl group, etc.; m3r represents 0 to 6; $B^R$ represents —$NR^{25R}R^{26R}$, etc.; and $R^{25R}$ and $R^{26R}$ represent a hydrogen atom or an optionally substituted C1-15 alkyl group when $X^R$ is not $CH_2$, etc.; and only required portions were extracted with respect to definition of each group), or a pharmaceutically acceptable salt thereof, or a prodrug thereof has an antagonistic activity against CXCR4. However, compounds having a spiro-bound cyclic group are not disclosed (refer to Patent Document 1).

It is disclosed that a compound represented by formula (S):

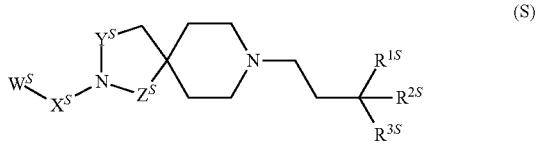

(wherein $W^S$ represents a C6-12 aralkyl optionally having a substituent, etc.; $X^S$, $Y^S$ and $Z^S$ each independently represents —CO— or —CH$_2$—, etc.; $R^{1S}$ represents a hydrogen atom, a hydroxyl group or a C1-10 alkyl which may have a substituent(s), etc.; $R^{2S}$ represents an alkyl which may have a substituent(s), etc.; $R^{3S}$ represents a hydrogen atom or an alkyl group which may have a substituent(s), etc.; and only required portions were extracted with respect to definition of each group), a pharmaceutically acceptable salt thereof, a hydrate thereof, or a solvate thereof has an antagonistic activity against CCR5. However, it is not disclosed to have an antagonistic activity against CXCR4 (refer to Patent Document 2).

It is disclosed that a compound represented by formula (T):

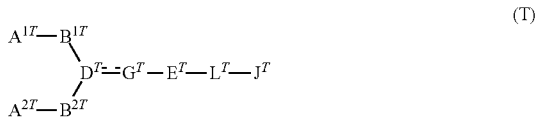

(wherein $A^{1T}$ and $A^{2T}$ each independently represents a nitrogen-containing heterocyclic group which may have a substituent(s), etc.; $B^{1T}$, $B^{2T}$ and $G^T$u each independently represents —CO—, —SO$_2$—, or —CH$_2$—, etc.; $D^T$ represents a carbon atom or a nitrogen atom; $E^T$ represents a cyclic group, etc.; $L^T$ represent a bond or a spacer having 1 to 4 atom(s) in its main chain; $J^T$ represents (1) a cyclic group which is substituted with a group having a basic group, and also may have a substituent(s)) or (2) a spirocyclic group which can be substituted with a group having a basic group, and also may have a substituent(s), provided that any one of $B^{1T}$, $B^{2T}$ and $G^T$u represents —CO— or —SO$_2$—; and only required portions were extracted with respect to definition of each group), a salt thereof, an N-oxide thereof or a solvate thereof, a prodrug thereof has an antagonistic activity against CXCR4 (refer to Patent Document 3).

It is disclosed that a compound represented by formula (U):

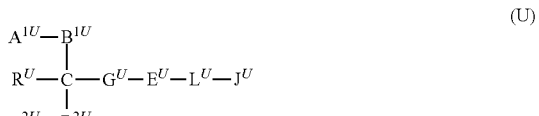

(wherein $A^{1U}$ and $A^{2U}$ each independently represents a nitrogen-containing heterocycle which may have a substituent(s), etc.; $B^{1U}$ and $B^{2U}$ each independently represents a bond or —CH$_2$—, etc.; $E^U$ represents a 3- to 8-membered monocyclic cyclic group which may have a substituent(s), etc.; $L^U$ represents a bond, —CH$_2$— or —CH$_2$—NH—, etc.; $J^u$ represents (1) a monocyclic or condensed cyclic group which is substituted with a group having a basic group, and also may have a substituent(s), or (2) a spiro-bound cyclic group which may be substituted with a group having a basic group, and also may have a substituent(s), etc.; $G^U$ represents —CO—, —CH$_2$—, —CH(OH)— or —NH—, etc.; $R^U$ represents a hydrogen atom or a substituent; and only required portions were extracted with respect to definition of each group), a salt thereof, an N-oxide thereof or a solvate thereof or a prodrug thereof has an antagonistic activity against CXCR4 (refer to Patent Document 4).

It is disclosed that a compound represented by formula (V):

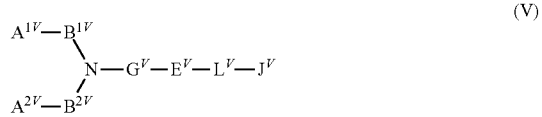

(wherein $A^{1V}$ and $A^{2V}$ each independently represents a nitrogen-containing heterocyclic group which may have a substituent(s), etc.; $B^{1V}$ and $B^{2V}$ each independently represents —CO—, —SO$_2$— or —CH$_2$—, etc.; $G^V$ represents a bond, —CO—, —SO$_2$— or —CH$_2$—, etc.; $E^V$ represents cyclic group which may have a substituent(s), etc.; $L^V$ represents a bond or spacer having 1 to 4 atom(s) in its main chain; $J^V$ represents (1) a cyclic group which is substituted with a group having a basic group, and may also have a substituent(s), or (2) spirocyclic group which may be substituted with a group having a basic group, and also may have a substituent(s), etc.; and only required portions were extracted with respect to definition of each group), a salt thereof, an N-oxide thereof or a solvate thereof, or a prodrug thereof has an antagonistic activity against CXCR4 (refer to Patent Document 5).

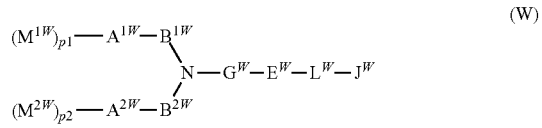

(wherein $M^{1W}$ and $M^{2W}$ each independently represents a group having an acidic group which may be protected with a protective group; $A^{1W}$ and $A^{2W}$ each independently represents a nitrogen-containing heterocycle which may have a substituent(s); $B^{1W}$ and $B^{2W}$ each independently represents a bond, —CO—, —SO$_2$— or —CH$_2$—, etc.; $G^W$ represents a bond, —CO—, —SO$_2$— or —CH$_2$—, etc.; $E^W$ represents a cyclic group which may have a substituent(s), etc.; $L^W$ represents a bond or spacer having 1 to 4 atom(s) in its main chain; $J^W$ represents (1) a cyclic group which is substituted with a group having a basic group, and also may have a substituent(s), or (2) spirocyclic group which may be substituted with a group having a basic group, and also may have a substituent(s), etc.; and only required portions were extracted with respect to definition of each group), a salt thereof, an N-oxide thereof or a solvate thereof, or a prodrug thereof has an antagonistic activity against CXCR4 (refer to Patent Document 6).

It is disclosed that a compound represented by formula (X):

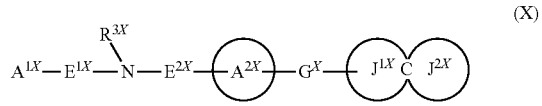

(wherein $A^{1X}$ represents a nitrogen-containing heterocycle which may have a substituent(s), etc.; ring $A^{2X}$ represents a divalent monocyclic cyclic group which may have a substituent(s); $E^{1X}$ represents a divalent C1-4 aliphatic hydrocarbon group which may have a substituent(s); $E^{2X}$ represents a methylene group or a carbonyl group; $R^{3X}$ represents (1) a hydrogen atom, (2) a hydroxyl group which may be protected with a protective group, a carboxyl group which may be protected with a protective group, or a C1-4 aliphatic hydrocarbon group which may be substituted with a sulfo group which may be protected with a protective group, and also may have a substituent(s), etc.; $G^X$ represents:

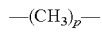

(in the group, p represents an integer of 1 to 4), etc.; ring $J^{1X}$ represents a 3- to 10-membered monocyclic or dicyclic heterocycle which has at least one nitrogen atom, and also may have an oxygen atom or an optionally oxidized sulfur atom; ring $J^{2X}$ represents (i) a C3-10 monocyclic or dicyclic carbon ring which is substituted with a group having a basic group, (ii) a 3- to 10-membered monocyclic or dicyclic heterocycle composed of a carbon atom, an oxygen atom and/or an optionally oxidized sulfur atom, which is substituted with a group having a basic group, or (iii) a 3- to 10-membered monocyclic or dicyclic heterocycle which may be substituted with a group having a basic group, and also has at least one nitrogen atom and may have an oxygen atom and/or an optionally oxidized sulfur atom; and ring $J^{1X}$ and ring $J^{2X}$ may have 1 to 8 substituents on the substitutable position and, when 2 or more substituent are present, a plurality of the substituents may be the same or different), a salt thereof, an N-oxide thereof, or a solvate thereof, or a prodrug thereof has an antagonistic activity against CXCR4 (refer to Patent Document 7).

It is disclosed that a compound represented by formula (Y):

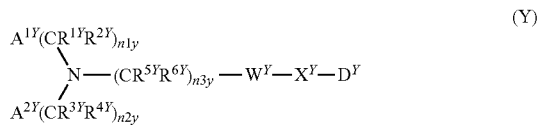

(wherein n1y, n2y and n3y represent 0 to 3; $R^{1Y}$, $R^{2Y}$, $R^{3Y}$, $R^{4Y}$, $R^{5Y}$ and $R^{6Y}$ each independently represents a hydrogen atom or an optionally substituted C1-15 alkyl group, etc.; $A^{1Y}$ and $A^{2Y}$ each independently represents a hydrogen atom or an optionally substituted monocyclic or polycyclic heterocyclic aromatic ring, etc.; $W^Y$ represents an optionally substituted benzene ring, etc.; $X^Y$ represents an optionally substituted monocyclic or polycyclic heterocyclic aromatic ring, an optionally substituted monocyclic or polycyclic aromatic ring, O, $CH_2$, $NR^{11Y}$ or $CHR^{35Y}$, etc.; $R^{11Y}$ represents a hydrogen atom or an optionally substituted C1-15 alkyl group, etc.; $CHR^{35Y}$ represents a carboxyl group, an alkoxycarbonyl group or a carbonyl group; $D^Y$ represents $-Q^Y-Y^Y-B^Y$, in which $Q^Y$ represents a bond or —CO— when $X^Y$ is $NR^{11Y}$, etc.; $Y^Y$ represents $-(CR^{18Y}R^{19Y})_{m3y}-$, etc.; $R^{18Y}$ and $R^{19Y}$ each independently represents a hydrogen atom or an optionally substituted C1-15 alkyl group, etc.; m3y represents 0 to 6; $B^Y$ represents $-NR^{25Y}R^{26Y}$, etc.; and $R^{25Y}$ and $R^{26Y}$ represent a hydrogen atom or an optionally substituted C1-15 alkyl group when $X^Y$ is not $CH_2$, etc.; and only required portions were extracted with respect to definition of each group), or a pharmaceutically acceptable salt thereof, or a prodrug thereof has an antagonistic activity against CXCR4. However, compounds having a spiro-bound cyclic group are not disclosed (refer to Patent Document 8).

However, Patent Documents 3 and 5 do not disclose specific compound having a carboxyl group. Patent Document 4 discloses a compound having a carboxyl group. However, activity of the compound was too insufficient to be formed into pharmaceuticals. Patent Documents 6 and 7 disclose that toxicity is avoided in a compound having a carboxyl group. However, there was neither description nor suggestion about stability in blood (elimination rate in blood) of these compounds and, actually, stability in blood of these compounds was insufficient.

PRIOR ART DOCUMENT

Patent Document

[Patent Document 1] International Publication WO 2004/024697 pamphlet
[Patent Document 2] International Publication WO 2005/007656 pamphlet
[Patent Document 3] International Publication WO 2006/022454 pamphlet
[Patent Document 4] International Publication WO 2007/049771 pamphlet
[Patent Document 5] International Publication WO 2007/058322 pamphlet
[Patent Document 6] International Publication WO 2007/132846 pamphlet
[Patent Document 7] International Publication WO 2008/016006 pamphlet
[Patent Document 8] International Publication WO 2005/085209 pamphlet

DISCLOSURE OF THE INVENTION

Problems to be Solved by the Invention

It is earnestly desired to develop a CXCR4 antagonist which is useful as pharmaceuticals such as a preventive and/or therapeutic agent for inflammatory and immune diseases, infections (for example, HIV infection), diseases associated with HIV infection (for example, acquired immunodeficiency syndrome (AIDS)), cancer, cancer metastasis, psychoneurotic diseases, cardiovascular diseases (for example, retinopathy), metabolic diseases, cancerous diseases, or an agent for regeneration therapy, and is also safe with less side effects. Particularly in the treatment of HIV infection, it is considered that HIV cannot be eradicated by drugs at present, and it is necessary to take drugs for a long period so as to prevent the onset of AIDS. It has been found that expression of drug-resistant viruses occurs with very high probability when the blood concentration of a therapeutic agent becomes the effective concentration or less (Virus, 53, 141 (2003)). Under these circumstances, it is earnestly desired to develop drugs which have high safety and persist an effective blood concentration for a long period of time, and also has a strong antagonistic activity against CXCR4. Examples of a compound having an antagonistic activity against CXCR4 include compounds described in Patent Document 3, Patent Document 5, Patent Document 6 and Patent Document 7. However, the compounds described in Patent Document 3 and Patent Document 5 have a risk (particularly, phospholipidosis induction activity) of exerting serious side effects upon administration to animals, while the compounds described in Patent Document 3, Patent Document 5, Patent Document 6 and Patent Document 7 were compounds which are unsuited for the development of pharmaceuticals since the compounds are early eliminated in blood and duration of action is short.

Means for Solving the Problems

The present inventors have intensively studied to overcome the above problems and intensively studied so as to create a compound which has a low risk of side effects and persists an effective blood concentration for a long period of time (stability in blood is very high), and also has a strong antagonistic activity against CXCR4. As a result, we have found, surprisingly, the compound represented by formula (I) of the present application can solve all problems, which have never been solved by the compound group of the prior art, in other words, the compound of the present invention persists an effective blood concentration for a long period of time, and also has a strong antagonistic activity against CXCR4 and can serve as a very high-safety CXCR4 antagonist drug when the compound of the present application has a basic nitrogen atom and a carboxyl group in the molecule and also maintain a specific spatial positional relation between the basic nitrogen atom and the carboxyl group. Thus, the present invention has been completed.

Thus, the present invention relates to:
[1] a compound represented by formula (I):

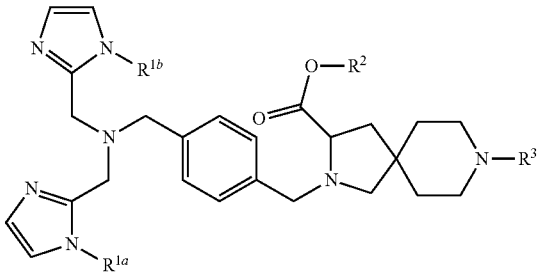

(I)

(wherein $R^{1a}$ and $R^{1b}$ each independently represents a hydrogen atom or a C1-4 alkyl group, $R^3$ represents a C3-8 branched-chain alkyl group or a C5-6 cycloalkyl group, $R^2$ represents a hydrogen atom or a C1-4 alkyl group), a salt thereof, an N-oxide thereof, or a solvate thereof;
[2] the compound according to the above-described [1], wherein $R^2$ is a hydrogen atom;
[3] the compound according to the above-described [1], wherein $R^{1a}$ is a hydrogen atom, and also $R^{1b}$ is a hydrogen atom or a methyl group;
[4] the compound according to the above-described [1], wherein $R^3$ is 1-ethylpropyl, 2,2-dimethylpropyl, 2-methylpropyl or cyclohexyl group;
[5] The compound according to the above-described [1], which is
(1) 2-(4-{[bis(1H-imidazol-2-ylmethyl)amino]methyl}benzyl)-8-(1-ethylpropyl)-2,8-diazaspiro[4.5]decane-3-carboxylic acid,
(2) 8-(1-ethylpropyl)-2-[4-({(1H-imidazol-2-ylmethyl)[(1-methyl-1H-imidazol-2-yl)methyl]amino}methyl)benzyl]-2,8-diazaspiro[4.5]decane-3-carboxylic acid,
(3) (3R)-8-(1-ethylpropyl)-2-[4-({(1H-imidazol-2-ylmethyl)[(1-methyl-1H-imidazol-2-yl)methyl]amino}methyl)benzyl]-2,8-diazaspiro[4.5]decane-3-carboxylic acid,
(4) (3S)-8-(1-ethylpropyl)-2-[4-({(1H-imidazol-2-ylmethyl)[(1-methyl-1H-imidazol-2-yl)methyl]amino}methyl)benzyl]-2,8-diazaspiro[4.5]decane-3-carboxylic acid,
(5) (3R)-2-(4-{[bis(1H-imidazol-2-ylmethyl)amino]methyl}benzyl)-8-(1-ethylpropyl)-2,8-diazaspiro[4.5]decane-3-carboxylic acid, or
(6) (3S)-2-(4-{[bis(1H-imidazol-2-ylmethyl)amino]methyl}benzyl)-8-(1-ethylpropyl)-2,8-diazaspiro[4.5]decane-3-carboxylic acid;

[6] a pharmaceutical composition comprising the compound represented by formula (I) according to the above-described [1], a salt thereof, an N-oxide thereof or a solvate thereof;
[7] the pharmaceutical composition according to the above-described [6], which is a CXCR4 antagonist;
[8] the pharmaceutical composition according to the above-described [6], which is preventive and/or therapeutic agent for CXCR4-mediated diseases or cancerous diseases, or an agent for regeneration therapy;
[9] the pharmaceutical composition according to the above-described [8], wherein the CXCR4-mediated disease is human immunodeficiency virus infection, acquired immunodeficiency syndrome, cancer, cancer metastasis, rheumatoid arthritis, arthritis, retinopathy, macular degeneration, pulmonary fibrosis, asthma, ischemic disease, systemic lupus erythematosus, neutropenia or transplanted organ rejection, or the agent for regeneration therapy is an agent for mobilization of peripheral blood stem cells;
[10] the pharmaceutical composition according to the above-described [9], wherein the CXCR4-mediated disease is human immunodeficiency virus infection;
[11] the pharmaceutical composition according to the above-described [8], wherein the cancerous disease is malignant lymphoma, multiple myeloma, acute myeloid leukemia, acute lymphocytic leukemia or chronic myeloid leukemia;
[12] a pharmaceutical comprising the compound represented by formula (I) according to the above-described [1], a salt thereof, an N-oxide thereof or a solvate thereof, and one or more kinds selected from reverse transcriptase inhibitor, protease inhibitor, CCR2 antagonist, CCR3 antagonist, CCR4 antagonist, CCR5 antagonist, CXCR4 antagonist, HIV integrase inhibitor, fusion inhibitor, CD4 antagonist, antibody against surface antigen of HIV, HIV-associated short interfering RNA, vaccine of HIV, and immunostimulant:
[13] a pharmaceutical comprising the compound represented by formula (I) according to the above-described [1], a salt thereof, an N-oxide thereof, or a solvate thereof, and one or more kinds selected from alkylation agent, platinum preparation, antimetabolite, antitumor antimicrobial agent, microtubule inhibitor, topoisomerase inhibitor, hormone therapeutic agent, immunopotentiator and molecular target drug;
[14] a pharmaceutical comprising the compound represented by formula (I) according to the above-described [1], a salt thereof, an N-oxide thereof, or a solvate thereof, and one or more kinds selected from G-CSF preparation, GM-CSF preparation, stem cell growth factor preparation and cyclophosphamide;
[15] a method for antagonizing CXCR4 in a mammal, which comprises administering an effective dosage of a compound represented by formula (I) according to the above-described [1], a salt thereof, an N-oxide thereof or a solvate thereof, to the mammal;
[16] a method for preventing and/or treating CXCR4-mediated diseases in a mammal, which comprises administering an effective dosage of a compound represented by formula (I) according to the above-described [1], a salt thereof, an N-oxide thereof or a solvate thereof to the mammal;
[17] use of a compound represented by formula (I) according to the above-described [1], a salt thereof, an N-oxide thereof or a solvate thereof for the production of a CXCR4 antagonist;
[18] use of a compound represented by formula (I) according to the above-described [1], a salt thereof, an N-oxide thereof or a solvate thereof for the production of preventive and/or therapeutic agent for CXCR4-mediated diseases; and

[19] the compound represented by formula (I) according to the above-described [1], a salt thereof, an N-oxide thereof, or a solvate thereof for use in a CXCR4 antagonist;
[20] use of the compound represented by formula (I) according to the above-described [1], a salt thereof, an N-oxide thereof, or a solvate thereof for prevention and/or treatment of CXCR4-mediated diseases; and
[21] the compound according to the above-described [1] represented by formula (II):

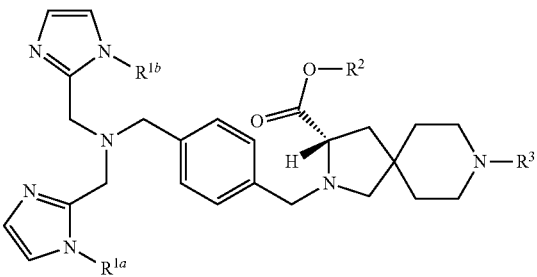

(II)

or formula (III):

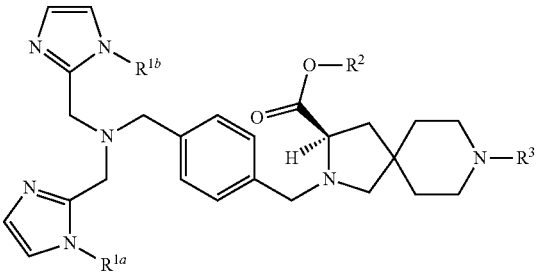

(III)

(wherein the symbol:

represents binding to the α-position, the symbol:

represents binding to the β-position, and other symbols have the same meaning as in the above-described [1]).

EFFECTS OF THE INVENTION

The compound of the present invention has an excellent antagonistic activity against CXCR4 and is useful as a preventive and/or therapeutic agent for CXCR4-mediated diseases or cancerous diseases, or an agent for regeneration therapy. Furthermore, the compound of the present invention is a very high-safety compound exhibiting a highly reduced risk of side effects (for example, phospholipidosis induction activity). Particularly, the compound of the present invention has a very strong HIV infection inhibitory activity and has very high stability in blood, and is therefore very useful as a therapeutic agent for HIV infection.

BEST MODE FOR CARRYING OUT THE INVENTION

In the present specification, the "C1-4 alkyl group" includes, for example, a methyl, ethyl, propyl, isopropyl, butyl, sec-butyl, tert-butyl or isobutyl group.

In the present specification, the "C1-4 alkyl group" represented by $R^{1a}$ and $R^{1b}$ has the same meaning as that of the above "C1-4 alkyl group".

In the present specification, the "C1-4 alkyl group" represented by $R^2$ has the same meaning as that of the above "C1-4 alkyl group". The compound in which $R^2$ represents a "C1-4 alkyl group", namely, a C1-4 alkyl ester represented by formula (I) immediately undergoes metabolism in vivo to convert into carboxylic acid. Therefore, it is a compound in which $R^2$ represents a "hydrogen atom", namely, a equivalent of carboxylic acid represented by formula (I). This can be confirmed by physiological conditions described in "Bunshisekkei (Molecular Design)", pp. 163-198, in "Iyakuhin no Kaihatsu (Development of Pharmaceuticals)" Vol. 7, 1990, published by Hirokawa Shoten.

In the present specification, examples of the "C3-8 branched-chain alkyl group" represented by $R^3$ include isopropyl, 2-methylpropyl, sec-butyl, tert-butyl, 1-methylbutyl, 2-methylbutyl, 3-methylbutyl, 1-ethylpropyl, 2,2-dimethylpropyl, 1-methylpentyl, 2-methylpentyl, 3-methylpentyl, 1-ethylpentyl, 1-methylhexyl, 2-methylhexyl, 3-methylhexyl, 2-ethylhexyl, 3-ethylhexyl, 1-methylheptyl, 2-methylheptyl and 3-methylheptyl groups.

In the present specification, examples of the "C5-6 cycloalkyl group" represented by $R^3$ include cyclopentyl and cyclohexyl.

In the present specification, unless otherwise specified, as is apparent to those skilled in the art, the symbol:

represents binding to the α-position, the symbol:

represents binding to the β-position, and the symbol:

represents a mixture of the α-position and the (3-position in optional ratio.

In formula (I) of the present invention, all of the respective definitions represented by $R^{1a}$, $R^{1b}$, $R^2$ and $R^3$ are preferred. Preferred groups are listed below.

In the present specification, $R^{1a}$ is more preferably a hydrogen atom.

In the present specification, $R^{1b}$ is more preferably a hydrogen atom or methyl, and most preferably a hydrogen atom.

In the present specification, $R^2$ is preferably, for example, a hydrogen atom, or a methyl, ethyl, propyl, isopropyl, butyl, sec-butyl, tert-butyl or isobutyl group, particularly preferably a hydrogen atom or methyl, and most preferably a hydrogen atom.

In the present specification, $R^3$ is preferably 1-ethylpropyl, 2,2-dimethylpropyl, 2-methylpropyl, cyclohexyl, and most preferably 1-ethylpropyl.

In the invention, a compound represented by formula (II):

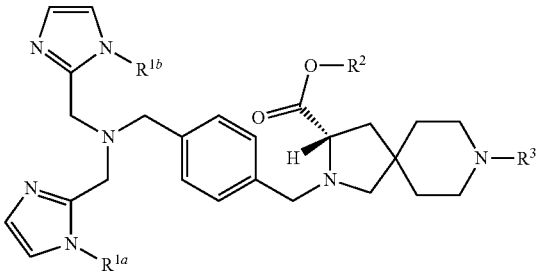

(II)

or formula (III):

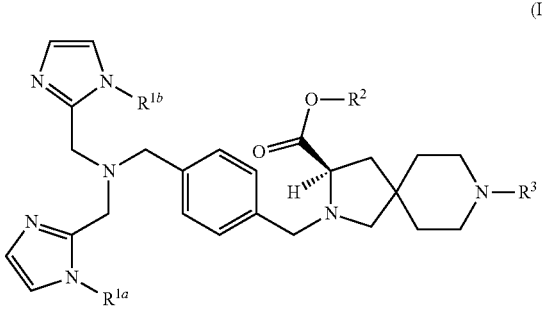

is particularly preferred, and a compound represented by formula (II) is more preferred.

All of compounds described in Examples, salts thereof, N-oxides thereof, or solvates thereof are preferred. More preferably, there can be exemplified (1) ethyl 2-(4-{[bis(1H-imidazol-2-ylmethyl)amino]methyl}benzyl)-8-(1-ethylpropyl)-2,8-diazaspiro[4.5]decane-3-carboxylate,
(2) 2-(4-{[bis(1H-imidazol-2-ylmethyl)amino]methyl}benzyl)-8-(1-ethylpropyl)-2,8-diazaspiro[4.5]decane-3-carboxylic acid,
(3) ethyl 8-(1-ethylpropyl)-2-[4-({(1H-imidazol-2-ylmethyl)[(1-methyl-1H-imidazol-2-yl)methyl]amino}methyl)benzyl]-2,8-diazaspiro[4.5]decane-3-carboxylate,
(4) 8-(1-ethylpropyl)-2-[4-({(1H-imidazol-2-ylmethyl)[(1-methyl-1H-imidazol-2-yl)methyl]amino}methyl)benzyl]-2,8-diazaspiro[4.5]decane-3-carboxylic acid,
(5) ethyl (3R)-2-(4-{[bis(1H-imidazol-2-ylmethyl)amino]methyl}benzyl)-8-cyclohexyl-2,8-diazaspiro[4.5]decane-3-carboxylate,
(6) (3R)-2-(4-{[bis(1H-imidazol-2-ylmethyl)amino]methyl}benzyl)-8-cyclohexyl-2,8-diazaspiro[4.5]decane-3-carboxylic acid,
(7) (3S)-2-(4-{[bis(1H-imidazol-2-ylmethyl)amino]methyl}benzyl)-8-cyclohexyl-2,8-diazaspiro[4.5]decane-3-carboxylic acid,
(8) ethyl (3S)-2-(4-{[bis(1H-imidazol-2-ylmethyl)amino]methyl}benzyl)-8-cyclohexyl-2,8-diazaspiro[4.5]decane-3-carboxylate,
(9) ethyl (3R)-2-(4-{[bis(1H-imidazol-2-ylmethyl)amino]methyl}benzyl)-8-(2,2-dimethylpropyl)-2,8-diazaspiro[4.5]decane-3-carboxylate,
(10) ethyl (3S)-2-(4-{[bis(1H-imidazol-2-ylmethyl)amino]methyl}benzyl)-8-(2,2-dimethylpropyl)-2,8-diazaspiro[4.5]decane-3-carboxylate,
(11) (3R)-2-(4-{[bis(1H-imidazol-2-ylmethyl)amino]methyl}benzyl)-8-(2,2-dimethylpropyl)-2,8-diazaspiro[4.5]decane-3-carboxylic acid,
(12) (3S)-2-(4-{[bis(1H-imidazol-2-ylmethyl)amino]methyl}benzyl)-8-(2,2-dimethylpropyl)-2,8-diazaspiro[4.5]decane-3-carboxylic acid,
(13) ethyl (3R)-8-(1-ethylpropyl)-2-[4-({(1H-imidazol-2-ylmethyl)[(1-methyl-1H-imidazol-2-yl)methyl]amino}methyl)benzyl]-2,8-diazaspiro[4.5]decane-3-carboxylate,
(14) ethyl (3S)-8-(1-ethylpropyl)-2-[4-({(1H-imidazol-2-ylmethyl)[(1-methyl-1H-imidazol-2-yl)methyl]amino}methyl)benzyl]-2,8-diazaspiro[4.5]decane-3-carboxylate,
(15) (3R)-8-(1-ethylpropyl)-2-[4-({(1H-imidazol-2-ylmethyl)[(1-methyl-1H-imidazol-2-yl)methyl]amino}methyl)benzyl]-2,8-diazaspiro[4.5]decane-3-carboxylic acid,
(16) (3S)-8-(1-ethylpropyl)-2-[4-({(1H-imidazol-2-ylmethyl)[(1-methyl-1H-imidazol-2-yl)methyl]amino}methyl)benzyl]-2,8-diazaspiro[4.5]decane-3-carboxylic acid,
(17) ethyl (3R)-2-(4-{[bis(1H-imidazol-2-ylmethyl)amino]methyl}benzyl)-8-isobutyl-2,8-diazaspiro[4.5]decane-3-carboxylate,
(18) ethyl (3S)-2-(4-{[bis(1H-imidazol-2-ylmethyl)amino]methyl}benzyl)-8-isobutyl-2,8-diazaspiro[4.5]decane-3-carboxylate,
(19) (3R)-2-(4-{[bis(1H-imidazol-2-ylmethyl)amino]methyl}benzyl)-8-isobutyl-2,8-diazaspiro[4.5]decane-3-carboxylic acid,
(20) (3S)-2-(4-{[bis(1H-imidazol-2-ylmethyl)amino]methyl}benzyl)-8-isobutyl-2,8-diazaspiro[4.5]decane-3-carboxylic acid,
(21) ethyl (3R)-2-(4-{[bis(1H-imidazol-2-ylmethyl)amino]methyl}benzyl)-8-(1-ethylpropyl)-2,8-diazaspiro[4.5]decane-3-carboxylate,
(22) ethyl (3S)-2-(4-{[bis(1H-imidazol-2-ylmethyl)amino]methyl}benzyl)-8-(1-ethylpropyl)-2,8-diazaspiro[4.5]decane-3-carboxylate,
(23) (3R)-2-(4-{[bis(1H-imidazol-2-ylmethyl)amino]methyl}benzyl)-8-(1-ethylpropyl)-2,8-diazaspiro[4.5]decane-3-carboxylic acid,
(24) (3S)-2-(4-{[bis(1H-imidazol-2-ylmethyl)amino]methyl}benzyl)-8-(1-ethylpropyl)-2,8-diazaspiro[4.5]decane-3-carboxylic acid,
(25) methyl (3S)-2-(4-{[bis(1H-imidazol-2-ylmethyl)amino]methyl}benzyl)-8-(1-ethylpropyl)-2,8-diazaspiro[4.5]decane-3-carboxylate,
(26) ethyl 2-(4-{[bis(1H-imidazol-2-ylmethyl)amino]methyl}benzyl)-8-cyclohexyl-2,8-diazaspiro[4.5]decane-3-carboxylate,
(27) 2-(4-{[bis(1H-imidazol-2-ylmethyl)amino]methyl}benzyl)-8-cyclohexyl-2,8-diazaspiro[4.5]decane-3-carboxylic acid,
(28) ethyl 2-(4-{[bis(1H-imidazol-2-ylmethyl)amino]methyl}benzyl)-8-(2,2-dimethylpropyl)-2,8-diazaspiro[4.5]decane-3-carboxylate,
(29) 2-(4-{[bis(1H-imidazol-2-ylmethyl)amino]methyl}benzyl)-8-(2,2-dimethylpropyl)-2,8-diazaspiro[4.5]decane-3-carboxylic acid,
(30) ethyl 2-(4-{[bis(1H-imidazol-2-ylmethyl)amino]methyl}benzyl)-8-isobutyl-2,8-diazaspiro[4.5]decane-3-carboxylate,
(31) 2-(4-{[bis(1H-imidazol-2-ylmethyl)amino]methyl}benzyl)-8-isobutyl-2,8-diazaspiro[4.5]decane-3-carboxylic acid, salts thereof, N-oxides thereof, or solvates thereof.

Most preferably, there can be exemplified 2-(4-{[bis(1H-imidazol-2-ylmethyl)amino]methyl}benzyl)-8-(1-ethylpropyl)-2,8-diazaspiro[4.5]decane-3-carboxylic acid, 8-(1-ethylpropyl)-2-[4-({(1H-imidazol-2-ylmethyl)[(1-methyl-1H-imidazol-2-yl)methyl]amino}methyl)benzyl]-2,8-diazaspiro[4.5]decane-3-carboxylic acid, (3R)-8-(1-ethylpropyl)-2-[4-({(1H-imidazol-2-ylmethyl)[(1-methyl-1H-imidazol-2-yl)methyl]amino}methyl)benzyl]-2,8-diazaspiro[4.5]decane-3-carboxylic acid, (3S)-8-(1-ethylpropyl)-2-[4-({(1H-imidazol-2-ylmethyl)[(1-methyl-1H-imidazol-2-yl)methyl]amino}methyl)benzyl]-2,8-diazaspiro[4.5]decane-3-carboxylic acid, (3R)-2-(4-{[bis(1H-imidazol-2-ylmethyl)amino]methyl}benzyl)-8-(1-ethylpropyl)-2,8-diazaspiro

[4.5]decane-3-carboxylic acid, (3S)-2-(4-{[bis(1H-imidazol-2-ylmethyl)amino]methyl}benzyl)-8-(1-ethylpropyl)-2,8-diazaspiro[4.5]decane-3-carboxylic acid, (3R)-2-(4-{[bis(1H-imidazol-2-ylmethyl)amino]methyl}benzyl)-8-cyclohexyl-2,8-diazaspiro[4.5]decane-3-carboxylic acid, (3S)-2-(4-{[bis(1H-imidazol-2-ylmethyl)amino]methyl}benzyl)-8-cyclohexyl-2,8-diazaspiro[4.5]decane-3-carboxylic acid, (3R)-2-(4-{[bis(1H-imidazol-2-ylmethyl)amino]methyl}benzyl)-8-(2,2-dimethylpropyl)-2,8-diazaspiro[4.5]decane-3-carboxylic acid, (3S)-2-(4-{[bis(1H-imidazol-2-ylmethyl)amino]methyl}benzyl)-8-(2,2-dimethylpropyl)-2,8-diazaspiro[4.5]decane-3-carboxylic acid, (3R)-2-(4-{[bis(1H-imidazol-2-ylmethyl)amino]methyl}benzyl)-8-isobutyl-2,8-diazaspiro[4.5]decane-3-carboxylic acid, (3S)-2-(4-{[bis(1H-imidazol-2-ylmethyl)amino]methyl}benzyl)-8-isobutyl-2,8-diazaspiro[4.5]decane-3-carboxylic acid, 2-(4-{[bis(1H-imidazol-2-ylmethyl)amino]methyl}benzyl)-8-cyclohexyl-2,8-diazaspiro[4.5]decane-3-carboxylic acid, 2-(4-{[bis(1H-imidazol-2-ylmethyl)amino]methyl}benzyl)-8-(2,2-dimethylpropyl)-2,8-diazaspiro[4.5]decane-3-carboxylic acid, 2-(4-{[bis(1H-imidazol-2-ylmethyl)amino]methyl}benzyl)-8-isobutyl-2,8-diazaspiro[4.5]decane-3-carboxylic acid, salts thereof, N-oxides thereof, or solvates thereof. Particularly preferably, 2-(4-{[bis(1H-imidazol-2-ylmethyl)amino]methyl}benzyl)-8-(1-ethylpropyl)-2,8-diazaspiro[4.5]decane-3-carboxylic acid, (3R)-2-(4-{[bis(1H-imidazol-2-ylmethyl)amino]methyl}benzyl)-8-(1-ethylpropyl)-2,8-diazaspiro[4.5]decane-3-carboxylic acid, (3S)-2-(4-{[bis(1H-imidazol-2-ylmethyl)amino]methyl}benzyl)-8-(1-ethylpropyl)-2,8-diazaspiro[4.5]decane-3-carboxylic acid, salts thereof, N-oxides thereof, or solvates thereof.

[Isomers]

In the present invention, all isomers are included unless otherwise specified. For example, linear and branched alkyl groups are included in the alkyl group. Furthermore, all of isomers (E-, Z-, cis-, and trans-isomers) on the ring and condensed ring, isomers (R-isomer, S-isomer, α, β configuration, enantiomer, and diastereomer) due to the presence of a symmetric carbon, optically active substances with optical rotation (D-, L-, d-, and l-compounds), polar compounds (high polar compound and low polar compound) generated by chromatographic separation, equilibrium compounds, rotational isomers, mixtures in an optional mixing ratio and racemic mixtures are included in the present invention.

[Salts and Solvates]

Salts of the compound represented by formula (I) include all of nontoxic salts and pharmaceutically acceptable salts. The pharmaceutically acceptable salt is preferably a water soluble salt which shows less toxicity. Among suitable salts of the compound represented by formula (I), examples of the salt to be formed with carboxylic acid include salts of alkali metals (potassium, sodium, lithium, etc.), salts of alkali earth metals (calcium, magnesium, etc.), salts of zinc group elements (zinc), ammonium salts (tetramethylammonium salt, tetrabutylammonium salt, etc.), salts of organic amines (triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine, etc.) or combinations thereof. For example, salts of sodium, calcium or a combination thereof are exemplified. Examples of the salt to be formed with a basic nitrogen include acid addition salts [inorganic acid salts (hydrochloride, hydrobromide, hydroiodide, sulfate, phosphate, nitrate, etc.), and organic acid salts (acetate, trifluoroacetate, lactate, tartrate, oxalate, fumarate, maleate, benzoate, citrate, methanesulfonate, ethanesulfonate, benzenesulfonate, toluenesulfonate, isethionate, glucuronate, gluconate, camphorsulfonate, ascorbate, xinafoate, etc.)] or combinations thereof.

Furthermore, salts include quaternary ammonium salts. The quaternary ammonium salt is obtained by quaternizing a nitrogen atom of the compound represented by formula (I) with $R^0$ group ($R^0$ group represents a C1-4 alkyl group, or a C1-4 alkyl group substituted with a phenyl group).

The compound of the present invention can be converted into N-oxide by an optional method. N-oxide is obtained by oxidizing a nitrogen atom of the compound represented by formula (I).

Examples of suitable solvate of the compound represented by formula (I) include solvates such as water, alcoholic solvent (for example, methanol, ethanol, etc.) and the like. The solvate is preferably nontoxic and water soluble. The solvate of the compound of the present invention also includes solvates of alkali metal salts, alkali earth metal salts, ammonium salts, salts of organic amine, and acid addition salts of the compound of the present invention.

The compound of the present invention can be converted into the above salts, N-oxides and solvates by a known method.

[Method for Producing Compound of the Present Invention]

The compound of the present invention represented by formula (I) can be prepared by appropriately improving a known method, for example, methods shown below, methods described in Examples, and a method described in Comprehensive Organic Transformations: A Guide to Functional Group Preparations, Second edition (written by Richard C. Larock, John Wiley & Sons Inc, 1999) and using improved methods in combination. In the following production methods, starting compounds may be used in the form of a salt. As the salt, those described as a salt of the compound of the above described formula (I) are used.

Among the compound represented by formula (I) of the present invention, a compound in which $R^{1a}$ represents a hydrogen atom, $R^{1b}$ represents a C1-4 alkyl group, and $R^2$ represents a C1-4 alkyl group, namely, a compound represented by formula (I-A):

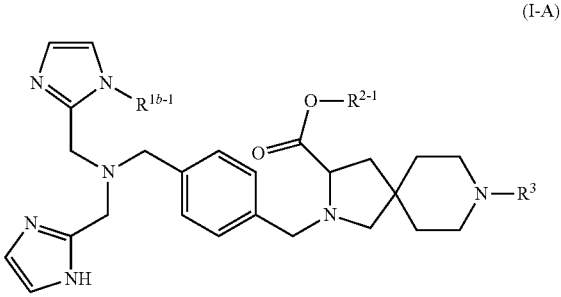

(I-A)

(wherein $R^{1b-1}$ represents C1-4 alkyl group, $R^{2-1}$ represents a C1-4 alkyl group, and $R^3$ has the same meaning as described above) can be prepared by subjecting a compound represented by formula (2):

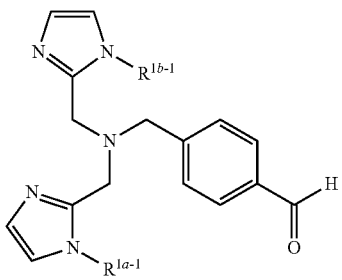

(wherein $R^{1a-1}$ represents a protective group of an imidazole group, and $R^{1b-1}$ has the same meaning as described above) and a compound represented by formula (3):

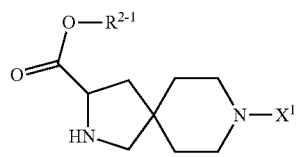

(wherein $X^1$ represents a protective group of an amino group, and $R^{2-1}$ has the same meaning as described above) to the reductive amination reaction and then subjecting to the deprotection reaction of the protective group and/or the cleavage reaction from a resin to obtain a compound, and subjecting the obtained compound and a compound represented by formula (4):

(wherein $R^{3-1}$ represents the remaining moiety in which carbon atoms combined with nitrogen atoms are substituted with an oxo group among $R^3$) to the reductive amination reaction.

These reductive amination reaction are known and carried out, for example, in an organic solvent (tetrahydrofuran, diethylether, dichloroethane, dichloromethane, dimethylformamide, acetic acid, methanol, ethanol, or a mixture thereof) at a temperature of 0 to 40° C. in the presence of a reducing agent (sodium triacetoxyborohydride, sodium cyanoborohydride, sodium borohydride, zinc borohydride, diisobutylalminium hydride, etc.), or carried out in a solvent (ether-based solvent (tetrahydrofuran, dioxane, dimethoxyethane, diethylether, etc.), alcohol-based solvent (methanol, ethanol, etc.), benzene-based solvent (benzene, toluene, etc.), nitrile-based solvent (acetonitrile, etc.), amide-based solvent (dimethylformamide, etc.), water, ethyl acetate, acetic acid, or a solvent mixture of two or more kinds of them) under a normal pressure or under a pressure in a hydrogen atmosphere at a temperature of 0 to 200° C. in the presence of a catalyst (palladium-carbon, palladium black, palladium hydroxide, platinum oxide, Raney nickel, etc.).

The deprotection reaction of a protective group can be carried out by the following method.

Examples of the protective group of the carboxyl group include methyl group, ethyl group, allyl group, tert-butyl group, trichloroethyl group, benzyl (Bn) group, and phenacyl group.

Examples of the protective group of the imidazole group and amino group include benzyloxycarbonyl group, t-butoxycarbonyl group, allyloxycarbonyl (Alloc) group, 1-methyl-1-(4-biphenyl)ethoxycarbonyl (Bpoc) group, trifluoroacetyl group, 9-fluorenylmethoxycarbonyl group, N,N-dimethylaminosulfamoyl group, benzyl(Bn) group, p-methoxybenzyl group, benzyloxymethyl (BOM) group, and 2-(trimethylsilyl)ethoxymethyl (SEM) group.

Other protective groups of the carboxyl group, imidazole group, or amino group can be used without any limitation as long as they are groups capable of being eliminated easily and selectively. For example, those described in T. W. Greene, Protective Groups in Organic Synthesis, Wiley, New York, 1999 can be used.

The deprotection reaction of the protective group of the carboxyl group, imidazole group or amino group is well known and include:

(1) deprotection reaction through alkali hydrolysis,
(2) deprotection reaction under acidic conditions,
(3) deprotection reaction through hydrogenolysis,
(4) deprotection reaction of silyl group,
(5) deprotection reaction using metal, and
(6) deprotection reaction using metal complex.

(1) These methods are described in detail below.

The deprotection reaction through alkali hydrolysis is carried out, for example, in an organic solvent (methanol, tetrahydrofuran, dioxane, etc.) at 0° C. to a reflux temperature of the solvent by using a hydroxide (sodium hydroxide, potassium hydroxide, lithium hydroxide, etc.) of alkali metal, a hydroxide (barium hydroxide, calcium hydroxide, etc.) of alkali earth metal or a carbonate (sodium carbonate, potassium carbonate, etc.), or an aqueous solution thereof or a mixture of them.

(2) The deprotection reaction under acidic conditions is carried out, for example, in an organic solvent (dichloromethane, chloroform, dioxane, ethyl acetate, anisole, etc.), an organic acid (acetic acid, trifluoroacetic acid, methanesulfonic acid, p-tosic acid, etc.), or an inorganic acid (hydrochloric acid, sulfuric acid, etc.) or a mixture (hydrogen bromide/acetic acid, etc.) thereof at 0° C. to a reflux temperature of the solvent.

(3) The deprotection reaction through hydrolysis is carried out, for example, in a solvent (ether-based solvent (tetrahydrofuran, dioxane, dimethoxyethane, diethylether, etc.), alcohol-based solvent (methanol, ethanol, etc.), benzene-based solvent (benzene, toluene, etc.), ketone-based solvent (acetone, methyl ethyl ketone, etc.), nitrile-based solvent (acetonitrile, etc.), amide-based solvent (dimethylformamide, etc.), water, ethyl acetate, acetic acid, or a solvent mixture of two or more kinds of them, etc.) under normal pressure or under a pressure in a hydrogen atmosphere in the presence of a catalyst (palladium-carbon, palladium black, palladium hydroxide, platinum oxide, Raney nickel, etc.), or in the presence of ammonium formate at 0° C. to a reflux temperature of the solvent.

(4) The deprotection reaction of a silyl group is carried out, for example, in an organic solvent (tetrahydrofuran, acetonitrile, etc.) which is miscible with water at a temperature of 0 to 40° C. by using tetrabutylammonium fluoride or hydrogen fluoride.

(5) The deprotection reaction using metal is carried out, for example, in an acidic solvent (acetic acid, buffer of pH 4.2 to 7.2, or a mixed solution of a solution thereof and an organic solvent such as tetrahydrofuran) at a temperature of 0 to 40° C. in the presence of a zinc powder while optionally applying ultrasonic wave.

(6) The deprotection reaction using a metal complex is carried out, for example, in an organic solvent (dichloromethane, dimethylformamide, tetrahydrofuran, ethyl acetate, acetonitrile, dioxane, ethanol, etc.), water or a solvent mixture thereof at a temperature of 0 to 40° C. in the presence of a trapping reagent (tributyltin hydride, triethylsilane, dimedone, morpholine, diethylamine, pyrrolidine, etc.), an organic acid (acetic acid, formic acid, 2-ethylhexanoic acid, etc.) and/or an organic acid salt (sodium 2-ethylhexanoate, potassium 2-ethylhexanoate, etc.), in the presence or absence of a phosphine-based reagent (triphenylphosphine, etc.) by using a metal complex (tetralcistriphenylphosphine palladium(0), bis(triphenylphosphine)palladium(II) dichloride, palladium(II) acetate, tris(triphenylphosphine)rhodium(I) chloride, etc.).

The deprotection reaction can also be carried out, for example, by the method described in T. W. Greene, Protective Groups in Organic Synthesis, Wiley, New York, 1999. As is apparent to those skilled in the art, the objective compound of the present invention can be easily prepared by selecting these deprotection reactions.

If the compound has a moiety to bind to a resin in the molecule and the resin is a polystyrene resin, the compound of the present invention can be cleaved from the resin by the following method. The reaction for cleavage from the resin is known and can be carried out, for example, by reacting in an organic solvent (dichloromethane, 1,2-dichloroethane, toluene, etc.) at 0 to 100° C. by using an acid (acetic acid, trifluoroacetic acid, hydrochloric acid, etc.).

The compound represented by formula (I-A) can also be produced by subjecting a compound represented by formula (5):

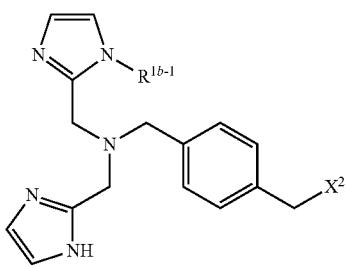

(5)

(wherein $X^2$ represents a sulfonate (for example, mesylate, nosylate, tosylate, trifluoromethane sulfonate, etc.) or a halogen atom (bromine atom, chlorine atom, etc.), and $R^{1b-1}$ has the same meaning as described above) with a compound represented by formula (6):

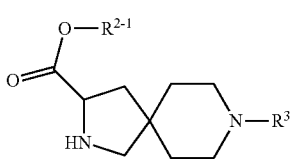

(6)

(wherein all symbols have the same meanings as described above), to the alkylation reaction and optionally subjecting to the deprotection reaction of a protective group and/or the cleavage reaction from a resin.

This alkylation reaction is known and is carried out, for example, in an organic solvent (for example, dimethylformamide, dimethyl sulfoxide, etc.) at a temperature of about 0 to 150° C. in the presence or absence of an alkali (potassium carbonate, sodium carbonate, triethylamine, etc.) and sodium iodide or potassium iodide.

This reaction is preferably carried out under an inert gas (argon, nitrogen, etc.) atmosphere under anhydrous conditions.

The deprotection reaction of this protective group can be performed by the above-described method.

Among the compound of the present invention represented by formula (I), a compound wherein $R^2$ represents a hydrogen atom, namely, a compound represented by formula (I-B):

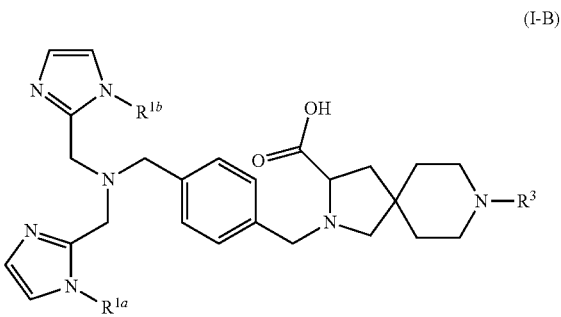

(I-B)

(wherein all symbols have the same meanings as described above), can be prepared by subjecting a compound represented by formula (I-C):

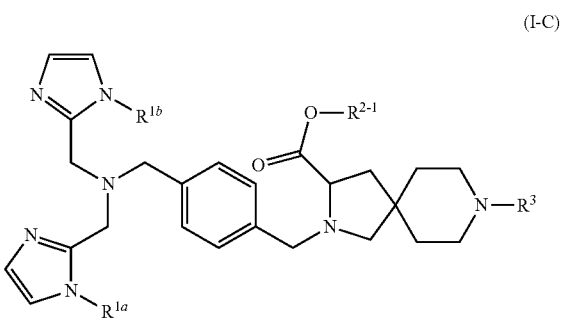

(I-C)

(wherein all symbols have the same meanings as described above) to the deprotection reaction through alkali hydrolysis, or the deprotection reaction under acidic conditions.

The deprotection reaction through alkali hydrolysis and the deprotection reaction under acidic conditions herein can be carried out by the same manner as that described above.

The compounds represented by formulas (2) to (6) used as other starting materials or reagents can be easily prepared by using per se known methods or known methods, for example, methods described in Comprehensive Organic Transformations: A Guide to Functional Group Preparations, Second edition (written by Richard C. Larock, John Wiley & Sons Inc, 1999) in combination.

Among the compound represented by formula (I) of the present invention, the compound other than those described above can be prepared by using the method described in Examples in the present description, or using known methods, for example, methods described in Comprehensive Organic Transformations: A Guide to Functional Group Preparations, Second edition (written by Richard C. Larock, John Wiley & Sons Inc, 1999) in combination.

In the respective reactions in the present specification, as is apparent to those skilled in the art, the reaction with heating can be carried out using a water bath, an oil bath, a sand bath, or microwave.

In the respective reactions in the present specification, a solid phase supported reagent obtained by supporting on a polymer (for example, polystyrene, polyacrylamide, polypropylene, polyethylene glycol, etc.) may be used.

In the respective reactions in the present specification, the reaction product can be purified by conventional purification means, for example, distillation under normal pressure or reduced pressure, high performance liquid chromatography using a silica gel or magnesium silicate, thin layer chromatography, ion-exchange resin, scavenger resin or column chromatography or washing, or recrystallization. The purification may be carried out for every reaction, or may be carried out after the completion of some reactions.

In the reaction using a polystyrene resin in the present specification, the reaction product can be purified by conventional purification methods, for example, washing plural times with a solvent (N,N-dimethylformamide, dichloromethane, methanol, tetrahydrofuran, toluene, acetic acid/toluene, etc.).

[Toxicity]

The compound of the present invention has very low toxicity and is considered to be safe enough for pharmaceutical use. It is considered that the compound of the present invention has high safety since there is very low risk of side effects such as phospholipidosis.

[Application to Pharmaceuticals]

The compound of the present invention has CXCR4 antagonistic activity in an animal including human, particularly human, and is therefore effective for prevention and/or treatment for CXCR4-mediated diseases [for example, inflammatory and immune diseases (for example, rheumatoid arthritis, joint pain, retinopathy, pulmonary fibrosis, transplanted organ rejection, graft-versus-host disease (GVHD), autoimmune diseases (systemic lupus erythematosus, etc.), etc.), allergic diseases (for example, asthma, atopic dermatitis, etc.), infections (for example, HIV infection, RSV infections, etc.), diseases associated with HIV infection (for example, acquired immunodeficiency syndrome (AIDS), carinii pneumonia, Kaposi's sarcoma, malignant lymphoma, etc.), psychoneurotic diseases (for example, dementia including Alzheimer's disease, Parkinson's disease, stroke, epilepsy, etc.), cerebral and cardiovascular diseases (for example, ischemic heart disease (arteriosclerosis, ischemia reperfusion, hypertension, myocardial infarction, etc.), diseases associated with neovascularization (for example, retinopathy (diabetic retinopathy, etc.), macular degeneration (age-related macular degeneration, etc.), cancerproliferation, etc.), etc.), blood diseases (for example, neutropenia, etc.), metabolic diseases (for example, diabetes, osteoporosis, etc.), cancer, cancer metastasis, etc.], cancerous diseases and the like. The compound of the present invention is also useful as a sensitizer against a cancer treating agent, and an agent for regeneration therapy (for example, agent for mobilization of peripheral blood stem cells, etc.).

In the present specification, examples of "cancer" in cancer and cancer metastasis include lung cancer, breast cancer, gastric cancer, esophageal cancer, large bowel cancer, liver cancer, biliary tract cancer, pancreatic cancer, uterine cervix cancer, endometrium cancer, ovarian cancer, germ cell tumor, malignant lymphoma, acute leukemia, chronic leukemia, adult T cell leukemia, multiple myeloma, malignant bone tumor, malignant soft tissue tumor, bladder cancer, upper urinary tract cancer, prostatic cancer, renal cell cancer, cutaneous cancer, head and neck cancer, and malignant tumor such as brain tumor.

In the present specification, examples of cancerous diseases include malignant lymphoma, multiple myeloma, acute leukemia, chronic leukemia, adult T cell leukemia, primary microglobulinemia, myeloproliferative disorder diseases, renal cell cancer, malignant melanoma, large bowel cancer, ovarian cancer, lung cancer, pancreatic cancer, breast cancer, rhabdomyosarcoma, germ cell tumor, sarcoma, Ewing's sarcoma, Wilms tumor, neuroblastoma, central nervous system tumor, medulloblastoma, brain tumor, testicular tumor, and cancer metastasis.

In the present specification, examples of diseases, to which the agent for mobilization of peripheral blood stem cells can be applied, include blood diseases (myelodysplastic syndrome, blood dyscrasias, aplastic anemia, paroxysmal nocturnal hemoglobinuria, disease of inborn error of metabolism, chronic active EBV infection, hemophagocytic syndrome, congenital hematopoietic injury, neutropenia, etc.), immunodeficiency diseases, autoimmune diseases, leukopenia and thrombocytopenia due to myeloablation after radiation therapy/chemical therapy against cancerous diseases, cardiovascular diseases (ischemic disease (peripheral arterial obstruction, arterial sclerosis, myocardial infarction, etc.), liver diseases (hepatic cirrhosis, acute hepatitis, chronic hepatitis, viral hepatitis, etc.), respiratory diseases (acute lung injury, pneumonia, etc.), bone diseases (osteoporosis, bone fracture, etc.) and the like. Particularly, non-Hodgkin's lymphoma, multiple myeloma and the like are exemplified.

The compound represented by formula (I) of the present invention, a salt thereof, an N-oxide thereof, or a solvate thereof is a compound which has high pharmaceutical activity, and is also less likely to be inhibited by a drug metabolizing enzyme and has low toxicity. These properties are most important properties required when preparations are developed, described in "The Merck Manual of Diagnosis and Therapy (17th Ed.), Merck & Co. ▯ The compound of the present invention satisfies these conditions and is expected to be useful for developing extremely excellent pharmaceuticals.

The fact that the compound of the present invention is useful as pharmaceuticals can be evaluated by methods described in various tests and biological examples described hereinafter, and methods which can be carried out by appropriately improving the above methods. The fact that the compound of the present invention is kinetically excellent can be easily evaluated by a known method, for example, a method described in "Drug Bioavailability (Science of Evaluation and Improvement) ▯ E Gendai Iryosha, published on Jul. 6, 1998. It is possible to easily evaluate the fact that the compound of the present invention is excellent in toxicity by methods described in various tests or known methods described hereinafter.

(1) Evaluation Experiment of Inhibitory Activity of Drug Metabolizing Enzyme of Compound of the Present Invention (i) Inhibitory Activity against Human CYP2C9

An inhibitory activity against CYP2C9 of the compound of the present invention can be evaluated by improving accuracy and/or sensitivity of the measurement in accordance with the method of Sato et al. (Pharmacokinetic, Xenobio. Metabol. and Dispos., 16(2), pp. 115-126 (2001)).

(ii) Inhibitory Activity against Human CYP3A4

Inhibitory activity against CYP3A4 of the compound of the present invention can be evaluated by an improved method described in "DRUG METABOLISM AND DISPOSITION", Vol. 28 (12), 1440-1448 (2000).

(2) Evaluation Experiment of Toxicity of Compound of Present Invention (i) Single Acute Toxicity Test in Rat The test compound is administered to six-week Crj:CD (SD) male and female rats by single intravenous dose or single oral administration. While comparing with value at the addition of the solvent, basic evaluation of toxicity can be performed by, for example, observation of performance status, autonomic movement and the like.

(ii) Evaluation of Activity of Compound of Present Invention Against hERG $I_{Kr}$ Current According to the report by Zou et al. (Biophys. J., Vol. 74, 230-241 (1998)), using HEK293 cell overexpressed of human ether-a-go-go-related gene (hERG), max tale current of hERG $I_{Kr}$ current induced by depolarization pulse followed by repolarization pulse is measured by patch-clamp recording. Rate of change (inhibition rate) is calculated by comparison max tale current between before addition of the test compound and 10 minutes after. The influence of the test compound against hERG $I_{Kr}$ current can be evaluated by the inhibition rate.

(iii) Evaluation of Influence of Compound of the Present Invention on Blood Pressure and Heart Rate A rat was anesthetized with urethane (1.2 g/kg subcutaneous administration). After neck midline dissection, a catheter for measuring blood pressure was inserted into a right common carotid artery. Then, after dissecting inguinal region, a catheter for chemical injection was inserted into a femoral vein and fixed. A catheter for measurement of blood pressure was connected to a pressure transducer and then the pressure waveform was recorded on a thermal writing pen recorder through an amplifier for strain compression (AP-641G (manufactured by NIHON KOHDEN CORPORATION)). In this case, regarding a heart rate, a value through a cardiotachometer (AT-601G (manufactured by NIHON KOHDEN CORPORATION)) using the pressure waveform obtained from the amplifier for strain compression as a trigger was recorded on a thermal writing pen recorder. The test compound was dissolved in a 10% WellSolve (trade name; manufactured by Celeste B Corporation) so as to adjust the concentration to 0.1, 0.3, 1, 3 or 10 mg/mL to prepare solutions. Each solution was intravenous administered at 1 mL/kg through the caudal vein over about 10 seconds. Accumulative administration of stepwise increasing of a dosage was carried out to an individual to evaluate a reduction in blood pressure and an increasing in heart rate.

The experiment systems (1) to (2) are not limited to the above methods and conventional methods can be utilized based on the basic technology. The measuring methods of the present invention can be modified to improve accuracy and/or sensitivity of the measurement for evaluating the compound of the present invention.

The compound of the present invention may be administered as a concomitant drug by using in combination with other drugs for the purpose of:
1) complementation and/or enhancement of the preventive and/or therapeutic effects of the compound,
2) improvement of pharmacokinetics and absorption of the compound and reduction of the dosage, and/or reduction of side effects of the compound.

Also, the compound of the present invention may be administered as a concomitant drug by using in combination with other drugs for the purpose of (1) complementation and/or enhancement of preventive and/or therapeutic effects, (2) improvement of pharmacokinetics and absorption of the compound and reduction of the dosage, and/or (3) reduction of side effects.

The concomitant drug of the compound of the present invention and other drugs may be administered in the form of a compounding agent(s) comprising both these components, or may be in the form of separation. In case of separately administering a preparation, simultaneous administration and administration with time-lag are included. In case of administration with time-lag, other drugs may be administered after the compound of the present invention is administered, or the compound of the present invention may be administered after other drugs may be administered. The administration method may be the same or different.

The disease, on which the preventive and/or therapeutic effects are exerted by the concomitant drug, is not particularly limited, and may be any disease which complements and/or enhances the preventive and/or therapeutic effects of the compound of the present invention.

A mass ratio of the compound of the present invention to other drugs is not particularly limited.

Examples of the other drug, which is used in combination with the compound of the present invention for complementation and/or enhancement of preventive and/or therapeutic effects against HIV infection and acquired immunodeficiency syndrome include reverse transcriptase inhibitors, protease inhibitors, chemokine (for example, CCR2, CCR3, CCR4, CCR5, CXCR4, etc.) antagonists, CD4 antagonists, antibody against surface antigen of HIV (for example, HIV-1, HIV-2, etc.), vaccine of HIV (for example, HIV-1, HIV-2, etc.), HIV-associated short interfering RNA and the like.

Examples of the reverse transcriptase inhibitors include (1) nucleoside reverse transcriptase inhibitors such as zidovudine (trade name: Retrovir), didanosine (trade name: Videx), zalcitabine (trade name: Hivid), stavudine (trade name: Zerit), lamivudine (trade name: Epivir), abacavir (trade name: Ziagen), adefovir, dipivoxil, emtricitabine (trade name: coviracil), tenofovir (trade name: viread), Combivir, Trizivir, truvada, or epzicom, (2) non-nucleoside reverse transcriptase inhibitors such as nevirapine (trade name: viramune), delavirdine (trade name: Rescriptor), efavirenz (trade name: Sustiva, Stocrin), capravirine (AG1549) and the like.

Examples of the protease inhibitors include indinavir (trade name: Kurikisiban), ritonavir (trade name: norvir), nelfinavir (trade name: Viracept), saquinavir (trade name: Invirase, Fortovase), amprenavir (trade name: agenerase), lopinavir (trade name: Kaletra), atazanavir (trade name: Reyataz), fosamprenavir (trade name: lexiva), tipranavir and the like.

Examples of the chemokine antagonist include an intrinsic ligand of a chemokine receptor, or a derivative thereof and a nonpeptidic low molecular weight compound, or an antibody against the chemokine receptor.

Examples of the intrinsic ligand of the chemokine receptor include MIP-1α, MIP-1β, RANTES, SDF-1α, SDF-1β, MCP-1, MCP-2, MCP-4, Eotaxin, and MDC.

Examples of the derivative of the intrinsic ligand include AOP-RANTES, Met-SDF-1a, and Met-SDF-1β.

Examples of the antibody of the chemokine receptor include Pro-140.

Examples of the CCR2 antagonist include compounds described in International Publication WO 99/07351 pamphlet, International Publication WO 99/40913 pamphlet, International Publication WO 00/46195 pamphlet, International Publication WO 00/46196 pamphlet, International Publication WO 00/46197 pamphlet, International Publication WO 00/46198 pamphlet, International Publication WO 00/46199 pamphlet, International Publication WO 00/69432 pamphlet, International Publication WO 00/69815 pamphlet, and Bioorg. Med. Chem. Lett., 10, 1803 (2000).

Examples of the CCR3 antagonist include compounds described in DE19837386 pamphlet, International Publication WO 99/55324 pamphlet, International Publication WO 99/55330 pamphlet, International Publication WO 00/04003 pamphlet, International Publication WO 00/27800 pamphlet, International Publication WO 00/27835 pamphlet, International Publication WO 00/27843 pamphlet, International Publication WO 00/29377 pamphlet, International Publication WO 00/31032 pamphlet, International Publication WO 00/31033 pamphlet, International Publication WO 00/34278 pamphlet, International Publication WO 00/35449 pamphlet, International Publication WO 00/35451 pamphlet, International Publication WO 00/35452 pamphlet, International Publication WO 00/35453 pamphlet, International Publication WO 00/35454 pamphlet, International Publication WO 00/35876 pamphlet, International Publication WO 00/35877 pamphlet, International Publication WO 00/41685 pamphlet, International Publication WO 00/51607 pamphlet, International Publication WO 00/51608 pamphlet, International Publication WO 00/51609 pamphlet, International Publication WO 00/51610 pamphlet, International Publication WO 00/53172 pamphlet, International Publication WO 00/53600 pamphlet, International Publication WO 00/58305 pamphlet, International Publication WO 00/59497 pamphlet, International Publication WO 00/59498 pamphlet, International Publication WO 00/59502 pamphlet, International Publication WO 00/59503 pamphlet, International Publication WO 00/62814 pamphlet, International Publication WO 00/73327 pamphlet, and International Publication WO 01/09088 pamphlet.

Examples of the CCR4 antagonist include compounds described in International Publication WO 02/030357 pamphlet, and International Publication WO 02/030358 pamphlet.

Examples of the CCR5 antagonist include compounds TAK-779, SCH-351125(SCH-C), SCH-417690(SCH-D), UK-427857, GW 873140A(ONO-4128), TAK-220 and TAK-652, maraviroc (trade name: Selzentry, Celsentri) and the like described in International Publication WO 99/17773 pamphlet, International Publication WO 99/32100 pamphlet, International Publication WO 00/06085 pamphlet, International Publication WO 00/06146 pamphlet, International Publication WO 00/10965 pamphlet, International Publication WO 00/06153 pamphlet, International Publication WO 00/21916 pamphlet, International Publication WO 00/37455 pamphlet, EP1013276 pamphlet, International Publication WO 00/38680 pamphlet, International Publication WO 00/39125 pamphlet, International Publication WO 00/40239 pamphlet, International Publication WO 00/42045 pamphlet, International Publication WO 00/53175 pamphlet, International Publication WO 00/42852 pamphlet, International Publication WO 00/66551 pamphlet, International Publication WO 00/66558 pamphlet, International Publication WO 00/66559 pamphlet, International Publication WO 00/66141 pamphlet, International Publication WO 00/68203 pamphlet, JP-A-2000-309598 pamphlet, International Publication WO 00/51607 pamphlet, International Publication WO 00/51608 pamphlet, International Publication WO 00/51609 pamphlet, International Publication WO 00/51610 pamphlet, International Publication WO 00/56729 pamphlet, International Publication WO 00/59497 pamphlet, International Publication WO 00/59498 pamphlet, International Publication WO 00/59502 pamphlet, International Publication WO 00/59503 pamphlet, International Publication WO 00/76933 pamphlet, International Publication WO 98/25605 pamphlet, International Publication WO 99/04794 pamphlet, International Publication WO 99/38514 pamphlet, Bioorg. Med. Chem. Lett., 10, 1803 (2000).

Examples of the CD4 antagonist include curdlan sulfate, TNX-355, BT-061, CD4 antagonist 802-2, 4162W94, PP-0102, anti-CD4 antibody, AD-519, TRX-1, and CD4-IgG.

Examples of the CXCR3 antagonist include compounds described in International Publication WO 01/16114 pamphlet, International Publication WO 02/083143 pamphlet, International Publication WO 02/085862 pamphlet, U.S. Pat. No. 6,469,002 specification and International Publication WO 03/101970 pamphlet.

Examples of the CXCR4 antagonist include AMD-3100, AMD-070, T-22, KRH-1120, KRH-1636, KRH-2731, CS-3955, compounds described in International Publication WO 00/66112 pamphlet, International Publication WO 2003/055876 pamphlet, International Publication WO 2004/024697 pamphlet, International Publication WO 2004/052862 pamphlet, International Publication WO 2006/022454 pamphlet, International Publication WO 2006/023400 pamphlet, International Publication WO 2006/020415 pamphlet, International Publication WO 2006/020891 pamphlet, International Publication WO 2006/036816 pamphlet, U.S. Patent No. 2006/069122A1 specification, International Publication WO 2006/034001 pamphlet, International Publication WO 2006/028896 pamphlet, International Publication WO 2006/048862 pamphlet, International Publication WO 2006/074426 pamphlet, U.S. Patent No. 2006/160860 specification, International Publication WO 2006/076131 pamphlet, International Publication WO 2006/026703 pamphlet, Japanese Unexamined Patent publication (Kokai) No. 2006-188445, International Publication WO 2006/090853 pamphlet, International Publication WO 2006/096444 pamphlet, U.S. Patent No. 2006/281712A1 specification, International Publication WO 2007/008539 pamphlet, U.S. Patent No. 2006/0293324A1 specification, International Publication WO 2006/117011 pamphlet, International Publication WO 2007/022385 pamphlet, and International Publication WO 2007/027999 pamphlet.

Examples of the fusion inhibitor include T-20 (pentafuside, Enfuvirtide, Fuseon (trade names)), and T-1249.

Examples of the HIV integrase inhibitor include Equisetin, Temacrazine, MK0518 (Raltegravir), PL-2500, V-165, NSC-618929, L-870810, and L-708906 analog, S-1360, and S-1838.

HIV-associated short interfering RNA is short interfering RNA with the gene of a HIV-associated factor as a target. Examples of the HIV-associated factor include reverse transcriptadse, protease, chemokine (for example, CCR2, CCR3, CCR4, CCR5, CXCR4, etc.), CD4, and HIV (HIV-1, HIV-2, etc.). Examples of the HIV-associated short interfering RNA include GPs-0193, HGTV-43, GEM-132, GEM-92, GEM-93, HYB-0184, GEM-91, UL36ANTI, ISIS-2922, ISIS-14803, GPI-2A, R-95288, and VRX-496.

Examples of the vaccine of HIV include Inflexal V, Vacc-4x, Vacc-5q, Typhim Vi, HBV-ISS, EP-1043, Tat Toxoid, IR-103, Remune, Flumist, AIDSVAX, and Therapore-P24.

The conventional clinical dosage of typical reverse transcriptase inhibitors and protease inhibitors is, for example, as described below, but is not limited thereto in the present invention.

Zidovudine: 100 mg capsule, three times per day in a dosage of 200 mg; 300 mg tablet, twice per day in a dosage of 300 mg;

Didanosine: 25 to 200 mg tablet, twice per day in a dosage of 125 to 200 mg;

Zalcitabine: 0.375 mg to 0.75 mg tablet, three times per day in a dosage of 0.75 mg;

Stavudine: 15 to 40 mg capsule, twice per day in a dosage of 30 to 40 mg;

Lamivudine: 150 mg tablet, twice per day in a dosage of 150 mg;

Abacavir: 300 mg tablet, twice per day in a dosage of 300 mg;

Nevirapine: 200 mg tablet, once per day for 14 days in a dosage of 200 mg, followed by twice per day;

Delavirdine: 100 mg tablet, three times per day in a dosage of 400 mg;

Efavirenz: 50 to 200 mg capsule, once per day in a dosage of 600 mg;

Indinavir: 200 to 400 mg capsule, three times per day in a dosage of 800 mg;

Ritonavir: 100 mg capsule, twice per day in a dosage of 600 mg;

Nelfinavir: 250 mg tablet, three times per day in a dosage of 750 mg;

Saquinavir: 200 mg capsule, three times per day in a dosage of 1,200 mg;

Amprenavir: 50 to 150 mg tablet, twice per day in a dosage of 1,200 mg.

Examples of the other drug, which is used in combination with the compound of the present invention for complementation and/or enhancement of preventive and/or therapeutic effects against cancer and cancer metastasis include alkylation agents (for example, cyclophosphamide, ifosfamide, thiotepa, melphalan, busulfan, nimustine hydrochloride, ranimustine, dacarbazine, procarbazine hydrochloride, temozolomide, etc.), platinum preparations (for example, cisplatin, carboplatin, Nedaplatin, oxaliplatin, etc.), antimetabolites (for example, methotrexate, pemetrexed, fluorouracil, tegafur, doxifluridine, capecitabine, cytarabine, enocitabine, gemcitabine hydrochloride, mercaptopurine, fludarabine phosphate, pentostatin, cladribine, hydroxyurea, etc.), antitumor antimicrobial agents (for example, doxorubicin hydrochloride, epirubicin, daunorubicin, idarubicin hydrochloride, pirarubicin, mitoxantrone hydrochloride, amrubicin hydrochloride, actinomycin D, bleomycin, sulfuric acid peplomycin, mytomycin C, aclarubicin, zinostatin, etc.), microtubule inhibitors (for example, vincristine, vindesine, vinblastine, vinorelbine, paclitaxel, docetaxel, etc.), topoisomerase inhibitors (for example, irinotecan, topotecan, etoposide, etc.), hormone therapeutic agents (for example, prednisolone, dexamethasone, tamoxifen, toremifene, medroxyprogesterone acetate, anastrozole, exemestane, letrozole, goserelin acetate, leuprorelin acetate, flutamide, bicalutamide, estramustine phosphate, fosfestrol, chlormadinone acetate, mepitiostane, methyltestosterone, etc.), immunopotentiators (for example, interferon α, interferon α-2a, interferon α-2b, interferon β, interferon γ-1a, interferon γ-n1, picibanil, krestin, GVAX, ipilimumab, anti-PD-1 antibody, etc.), molecular target drugs (for example, trastuzumab, rituximab, imatinib, gefitinib, gemtuzumab ozogamicin, bortezomib, erlotinib, cetuximab, bevacizumab, sunitinib, sorafenib, dasatinib, panitumumab, pegaptanib, vatalanib, ranibizumab, SU-6668, SU-11248, neovastat, vandetanib, etc.) and the like.

Examples of the other drug, which is used in combination with the compound of the present invention for complementation and/or enhancement of an agent for regeneration therapy, include cytokines and various growth factors, for example, various CSFs (for example, G-CSF, GM-CSF, etc.), various interleukins (for example, IL-3, 6, 7, 11, 12, etc.), EPO, TPO, SCF, FLT3 ligand, MIP-1α, cyclophosphamide and the like.

Examples of the other drug, which is used in combination with the compound of the present invention include the followings.

Examples of the other drug for complementation and/or enhancement of the preventive and/or therapeutic effects against inflammatory diseases (arthritis and rheumatoid arthritis, etc.) of the compound of the present invention include metalloproteinase inhibitor, immune inhibitor, non-steroid anti-inflammatory drug (NSAID), steroid drug, prostaglandins, phosphodiesterase inhibitor, cannabinoid-2 receptor stimulant, disease modifying anti-rheumatic drug (slow-acting anti-rheumatic drug), anti-inflammatory enzyme preparation, cartilage protective agent, T cell inhibitor, TNFα inhibitor, prostaglandin synthetase inhibitor, L-6 inhibitor, interferon γ agonist, IL-1 inhibitor and the like.

Examples of the other drug for complementation and/or enhancement of the preventive and/or therapeutic effects against inflammatory, immune disease (for example, autoimmune disease, transplanted organ rejection, etc.) of the compound of the present invention include immune inhibitor. Examples of the immune inhibitor include tacrolimus (FK506), cyclosporine, sirolimus (rapamycin), corticosteroid, azathioprine, mycophenolate mophetyl, FTY720, cyclophosphamide and the like.

Examples of the other drug for complementation and/or enhancement of the preventive and/or therapeutic effects against diseases associated with neovascularization (for example, macular degeneration, retinopathy, etc.) of the compound of the present invention include antiangiogenic agents (for example, ranibizumab, pegaptanib, bevasiranib, etc.), steroiods, antioxidants (for example, vitamin C (ascorbic acid), vitamin E (tocopherol acetate), β carotin, zinc ions (zinc sulfurate, etc.) such as zinc chelating agent, zinc ion agent, copper ions (sodium copper-chlorophyllin, etc.) such as copper chelating agent, copper ion agent, and the like.

Examples of the other drugs for complementation and/or enhancement of the preventive and/or therapeutic effects of the compound of the present invention against allergic diseases (e.g. asthma, etc.) include antihistaminic agents, anti-allergic agents (chemical mediator release inhibitors, histamine antagonists, thromboxane synthetase inhibitors, thromboxane antagonists, Th2 cytokine inhibitors), steroids, bronchodilator agents (xanthine derivatives, sympathomimetic agents, parasympathomimetic agents), vaccinotherapeutic agents, gold preparations, Chinese medicines, basic nonsteroidal anti-inflammatory drugs, 5-lipoxygenase inhibitors, 5-lipoxygenase activation protein antagonists, leukotriene synthesis inhibitors, prostaglandins, cannabinoid-2 receptor stimulants, antitussive drugs, expectorants and the like.

Examples of the other drug for complementation and/or enhancement of the preventive and/or therapeutic effects against bone diseases (for example, osteoporosis, bone fracture, etc.) of the compound of the present invention include phosphodiesterase 4 inhibitor, bisphosphonate preparation, vitamin D preparation, calcium adjuvant, estrogen preparation, calcitonin preparation, isoflavone-based preparation, anabolic steroid preparation, vitamin K preparation, cathepsin K inhibitor, prostaglandins, HMG-CoA reductase inhibitor, parathyroid hormone, growth factors, caspase-1 inhibitor, PTHrP derivative, metalloproteinase inhibitor, farnesoid X receptor agonist, estrogen agonist, progesterone agonist and the like.

A combination of any two or more kinds other drugs may be administered.

The other drugs, which complements and/or enhances the preventive and/or therapeutic effects of the compound of the present invention, includes not only those which have ever been found based on the above described mechanism, but also those which may be found in future.

The compound of the present invention is safe and has low toxicity and therefore can be administered to human and mammal other than human (for example, rat, mouse, rabbit, sheep, pig, cow, cat, dog, monkey, etc.).

In order to use a pharmaceutical composition comprising the compound of the present invention or a concomitant drug of the compound of the present invention and other drugs, it is commonly administered, systemically or locally, in an oral or parenteral dosage form.

The dosage of the pharmaceutical preparation varies depending on the age, body weight, symptom, desired therapeutic effect, route of administration and duration of treatment. For the human adult, the dosage per person is between 0.1 ng and 5,000 mg, by oral administration, up to several times per day, between 0.1 ng and 500 mg, by parenteral administration, or continuous administration between 1 hour to 24 hours per day intravenously.

As a matter of course, since the dosage varies under various conditions as is described above, the dosage may be sometimes sufficient which is smaller than the above range, or sometimes the dosage must be more than the above range.

In case of administering a pharmaceutical composition comprising the compound of the present invention, or a concomitant drug of the compound of the present invention and other drugs, it is used as solid preparations for internal use and solutions for internal use for oral administration, and injections, external preparations, suppositories, ophthalmic solutions, nasal drops, inhalants and the like for parenteral administration.

Examples of the solid preparation for internal use for oral administration include tablets, pills, capsules, powders, and granules. Capsules include hard capsules and soft capsules.

In such a solid preparation for internal use, one or more active substances are used as they are, or used after mixing with excipients (lactose, mannitol, glucose, microcrystalline cellulose, starch, etc.), binders (hydroxypropyl cellulose, polyvinyl pyrrolidone, magnesium aluminometasilicate, etc.), disintegrants (calcium glycolate cellulose, etc.), lubricants (magnesium stearate, etc.), stabilizers and solubilizing agents (glutamic acid, aspartic acid, etc.) and forming into a preparation according to a conventional method. If necessary, the preparation may be coated with a coating agent (saccharose, gelatin, hydroxypropyl cellulose, hydroxypropylmethyl cellulosephthalate, etc.) or may be coated with two or more layers. Furthermore, capsules made of an absorbable substance such as gelatin is included.

The solutions for internal use for oral administration include pharmaceutically acceptable water, suspensions, emulsions, syrups, and elixirs. In such a solution, one or more active substances are dissolved, suspended or emulsified in a diluent used commonly (purified water, ethanol, mixed solution thereof, etc.). Furthermore, this solution may contain humectants, suspending agents, emulsifiers, sweeteners, flavors, aromatics, preservatives, buffers, and the like.

The dosage form of the external preparation for parenteral administration includes, for example, ointment, gel, cream, fomentation, patch, liniment, propellant, inhalant, spray, aerosol, ophthalmic solution, and nasal drop. These products contain one or more active substances and are prepared according to the formulation which is known or commonly used.

An ointment is prepared in accordance with a well known formulation or a commonly employed formulation. For example, it is prepared by triturating or dissolving one or more active substances in a base. An ointment base is selected from well known ones or those commonly employed. For example, those selected from higher fatty acids or higher fatty acid esters (adipic acid, myristic acid, palmitic acid, stearic acid, oleic acid, adipate ester, myristate ester, palmitate ester, stearate ester, oleate ester, etc.), waxes (beeswax, whale wax, ceresin, etc.), surfactants (polyoxyethylene alkyl ether phosphate ester, etc.), higher alcohols (cetanol, stearyl alcohol, cetostearyl alcohol, etc.), silicone oils (dimethylpolysiloxane, etc.), hydrocarbons (hydrophilic petrolatum, white petrolatum, purified lanolin, liquid paraffin, etc.), glycols (ethylene glycol, diethylene glycol, propylene glycol, polyethylene glycol, macrogol, etc.), vegetable oils (castor oil, olive oil, sesame oil, turpentine oil, etc.), animal oils (mink oil, egg yolk oil, squalane, squalene, etc.), water, absorption accelerators, agents for preventing contact dermatitis are used alone or in combination. Furthermore, it may contain humectants, preservatives, stabilizers, antioxidizing agents, flavors, and the like.

A gel is prepared according to the formulation which is known or commonly used. For example, it is prepared by dissolving one or more active substances in a base. A gel base is selected from a base which is known or commonly used. For example, those selected from lower alcohols (ethanol, isopropyl alcohol, etc.), gelling agents (carboxymethyl cellulose, hydroxyethyl cellulose, hydroxypropyl cellulose, ethyl cellulose, etc.), neutralizers (triethanolamine, diisopropanolamine, etc.), surfactants (monostearic acid polyethylene glycol, etc.), gums, water, absorption accelerator, and agent for preventing contact dermatitis are used alone or in combination. Furthermore, it may contain preservatives, antioxidizing agents, and flavoring agent.

A cream is prepared according to the formulation which is known or commonly used. For example, it is prepared by dissolving or emulsifying one or more active substances in a base. A cream base is selected from a base which is known or commonly used. For example, those selected from higher fatty acid esters, lower alcohols, hydrocarbons, polyhydric alcohols (propylene glycol, 1,3-butylene glycol, etc.), higher alcohols (2-hexyl decanol, cetanol, etc.), emulsifiers (polyoxyethylene alkyl ethers, fatty acid esters, etc.), water, absorption accelerators, and agents for preventing contact dermatitis are used alone or in combination. Furthermore, it may contain preservatives, antioxidizing agents, and flavoring agent.

A fomentation is prepared according to the formulation which is known or commonly used. For example, it is prepared by dissolving one or more active substances in a base to obtain a kneaded mixture and spreading the kneaded mixture over a substrate. A fomentation base is selected from a base which is known or commonly used. For example, those selected from thickeners (polyacrylic acid, polyvinyl pyrrolidone, gum arabic, starch, gelatin, methyl cellulose, etc.), humectants (urea, glycerin, propylene glycol, etc.), fillers (kaolin, zinc oxide, talc, calcium, magnesium, etc.), water, solubilizing agents, tackifiers, and agents for preventing contact dermatitis are used alone or in combination. Furthermore, it may contain preservatives, antioxidizing agents, and flavoring agent.

A patch is prepared according to the formulation which is known or commonly used. For example, it is prepared by dissolving one or more active substances in a base, and spreading the solution over a substrate. A patch base is selected from a base which is known or commonly used. For example, those selected from polymer bases, fats and oils, higher fatty acids, tackifiers, and agents for preventing contact dermatitis are used alone or in combination. Furthermore, it may contain preservatives, antioxidizing agents, and flavoring agent.

A liniment is prepared according to the formulation which is known or commonly used. For example, it is prepared by dissolving, suspending or emulsifying one or more active substances in one or more kinds selected from water, alcohol (ethanol, polyethylene glycol, etc.), higher fatty acid, glycerin, soap, emulsifier, and suspending agent. Furthermore, it may contain preservatives, antioxidizing agents, and flavoring agent.

A propellant, an inhalant, and a spray may contain, in addition to a diluent used commonly, a stabilizer such as sodium hydrogensulfite and a buffer capable of imparting isotonicity, for example, an isotonic agent such as sodium chloride, sodium citrate or citric acid.

An injection for parenteral administration includes all injections and also includes a drop. For example, it includes intramuscular injection, subcutaneous injection, endermic injection, intraarterial injection, intravenous injection, intraperitoneal injection, intraspinal injection, intravitreous injection, and intravenous drop.

The injection for parenteral administration includes solutions, suspensions, emulsions, and solid injections used by dissolving or suspending in a solvent before use. The injection is used after dissolving, suspending, or emulsifying one or more active substances in a solvent. As the solvent, for example, distilled water for injection, physiological saline, vegetable oil, and alcohols such as propylene glycol, polyethylene glycol or ethanol are used alone or in combination. Furthermore, the injection may contain stabilizers, solubilizing agents (glutamic acid, aspartic acid, Polysolvate 80®, etc.), suspending agents, emulsifiers, soothing agents, buffers, and preservatives. These injections are prepared by sterilizing in the final process, or prepared by an aseptic treatment. Also, a sterile solid, for example, a freeze-dried product is prepared and can be used after dissolving in sterilized distilled water or distilled water for sterile injection, or the other solvent before use.

An ophthalmic solution for parenteral administration includes ophthalmic solution, suspension type ophthalmic solution, emulsion type ophthalmic solution, ophthalmic solution soluble when used, and eye ointment.

These ophthalmic solutions are prepared according to a known method. For example, one or more active substances are dissolved, suspended or emulsified in a solvent before use. As the solvent for ophthalmic solution, for example, sterilized purified water, physiological saline, and other aqueous solvent or non-aqueous agent for injection (for example, vegetable oil, etc.) are used alone or in combination. If necessary, the ophthalmic solution may contain appropriately selected isotonizing agents (sodium chloride, concentrated glycerin, etc.), buffering agents (sodium phoshoate, sodium acetate, etc.), surfactants (polysolvate 80 (trade name), polyoxyl 40 stearate, polyoxyethylene hardened castor oil, etc.), stabilizers (sodium citrate, sodium edetate, etc.), and antiseptics (benzalkonium chloride, paraben, etc.). These ophthalmic solutions are prepared by sterilizing in the final process, or prepared by an aseptic treatment. Also, a sterile solid, for example, a freeze-dried product is prepared and can be used after dissolving in sterile purified water or the other solvent before use.

An inhalant for parenteral administration includes aerozol, inhalation powder, and inhalation solution, and the inhalation solution may be such a configuration that it is used after dissolving in water or other suitable medium at the point of use.

These inhalants are prepared according to a known method. For example, an inhalation solution is prepared by appropriately selecting antiseptics (benzalkonium chloride, paraben, etc.), colorants, buffering agents (sodium phosphate, sodium acetate, etc.), isotonizing agents (sodium chloride, concentrated glycerin, etc.), thickeners (carboxyvinyl polymer, etc.), and absorption accelerator, if necessary.

An inhalation powder is prepared by appropriately selecting lubricants (stearic acid and a salt thereof, etc.), binders (starch, dextrin, etc.), excipients (lactose, cellulose, etc.), colorants, antiseptics (benzalkonium chloride, paraben, etc.), and absorption accelerator, if necessary.

In case of administering the inhalation solution, a spraying apparatus (atomizer, nebulizer) is commonly used. In case of administering the inhalation powder, an inhalation administration apparatus for powder is commonly used.

The other composition for parenteral administration includes suppositories for intrarectal injection and pessaries for vaginal administration, which contain one or more active substances and are formulate by a conventional method.

Designation of the compound of the present invention is described below.

The compounds used in the present invention were commonly designated using a computer program ACD/Name Batch® (manufactured by Advanced Chemistry Development Inc.) which designates according to the regulation of IUPAC, or commonly designated according to IUPAC Nomenclature. For example, a compound of formula (I) in which $R^{1a}$ and $R^2$ are hydrogen atoms, $R^{1b}$ is methyl, and $R^3$ is isobutyl, namely, a compound represented by formula:

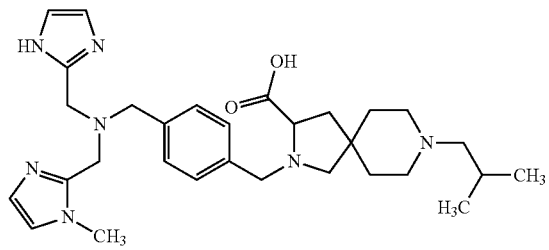 [SMILES: CC(C)CN1CCC2(CC1)CC(C(=O)O)N(Cc1ccc(CN(Cc3ncc[nH]3)Cc3nccn3C)cc1)C2]

was designated as 2-[4-({(1H-imidazol-2-ylmethyl)[(1-methyl-1H-imidazol-2-yl)methyl]amino}methyl)benzyl]-8-isobutyl-2,8-diazaspiro[4.5]decane-3-carboxylic acid.

EXAMPLES

The present invention is described in detail based on Examples, but the present invention is not limited thereto.

Among the compound of the present invention, an optically active compound can be prepared, for example, by optically resolving a racemate of the compound of the present invention using chromatography or recrystallization, or using an optically active raw material or asymmetric synthesis reaction. It is also possible to optically resolve at a stage of a synthesis intermediate.

The point of separation by chromatography and the solvent in the parentheses shown in TLC indicate a dissolution medium or an eluent used, and the proportion indicates a volume ratio.

NMR is a measured value of $^1$HNMR at 300 MHz and the solvent shown in the parentheses of NMR indicates a solvent used in the measurement.

Example 1

8-tert-butyl 3-ethyl 2-(4-{[bis(1H-imidazol-2-ylmethyl)amino]methyl}benzyl)-2,8-diazaspiro[4.5]decane-3,8-dicarboxylate Under an argon atmosphere, 4-{[bis(1H-imidazol-2-ylmethyl)amino]methyl}benzaldehyde (International Publication WO 2007/058322 pamphlet, Example 28; 21.0 g) and 8-tert-butyl 3-ethyl 2,8-diazaspiro[4.5]decane-3,8-dicarboxylate (JP 2004-002470, Example 21f; 21.2 g) were dissolved in acetic acid (4.5 mL) and anhydrous N,N-dimethylformamide (225 mL), followed by stirring at room temperature for 10 minutes. To this solution, sodium triacetoxyborohydride (17.3 g) was added. The reaction solution was stirred at room temperature for 3 hours. To the reaction solution, an aqueous sodium hydrogen carbonate solution was added, followed by extraction with ethyl acetate. The organic layer was washed with saturated brine and then dried over anhydrous sodium sulfate, and concentrated under reduced pressure. The residue was dissolved in ethanol (300 mL) and the solution was heated at reflux for 2 hours. The reaction solution was concentrated under reduced pressure and the residue was purified by silica gel chromatography (CHROMATOREX NH (trade name), manufactured by Fuji Silysia Chemical Ltd.) (n-hexane:ethyl acetate=1:1→1:2→0:1→ethyl acetate:ethanol=19:1→9:1) to obtain the title compound (24.4 g) having the following physical properties.

TLC: Rf 0.25 (dichloromethane:methanol:28% ammonia water=90:10:1);

NMR (CDCl$_3$): δ 1.24 (t, J=7.0 Hz, 3H), 1.37-1.47 (m, 1H), 1.55-1.65 (m, 2H), 1.82 (dd, J=13.0, 7.3 Hz, 1H), 1.96 (dd, J=13.0, 8.8 Hz, 1H), 2.23 (d, J=9.1 Hz, 1H), 2.91 (d, J=9.1 Hz, 1H), 3.24-3.40 (m, 5H), 3.50 (d, J=13.2 Hz, 1H), 3.60 (s, 6H), 3.86 (d, J=13.2 Hz, 1H), 4.09 (q, J=7.0 Hz, 2H), 7.03 (s, 4H), 7.18-7.29 (m, 4H).

Example 2

Ethyl 2-(4-{[bis(1H-imidazol-2-ylmethyl)amino]methyl}benzyl)-2,8-diazaspiro[4.5]decane-3-carboxylate Under an argon atmosphere, the compound obtained in Example 1(1) (24.4 g) was dissolved in ethanol (120 mL) and a 4N hydrogen chloride-dioxane solution (102 mL) was added, followed by stirring at room temperature for 3 hours. The reaction solution was concentrated under reduced pressure and the residue was diluted with dichloromethane and neutralized with an aqueous 2N sodium hydroxide solution, and then the brine was added. The mixed solution was extracted with dichloromethane and then washed with saturated brine. The organic layer was dried over anhydrous sodium sulfate, concentrated under reduced pressure to obtain the title compound (20.9 g) having the following physical properties.

TLC: Rf 0.35 (dichloromethane:methanol:28% ammonia water=80:20:2);

NMR (CDCl$_3$): δ 1.24 (t, J=7.1 Hz, 3H), 1.42-1.53 (m, 2H), 1.59-1.67 (m, 2H), 1.83 (dd, J=12.8, 8.1 Hz, 1H), 1.98 (dd, J=12.8, 8.1 Hz, 1H), 2.21 (d, J=9.3 Hz, 1H), 2.66-2.83 (m, 4H), 2.93 (d, J=9.3 Hz, 1H), 3.33 (t, J=8.1 Hz, 1H), 3.49 (d, J=13.2 Hz, 1H), 3.59 (s, 6H), 3.86 (d, J=13.2 Hz, 1H), 4.09 (q, J=7.1 Hz, 2H), 7.02 (s, 4H), 7.19-7.31 (m, 4H).

Example 3

Ethyl 2-(4-{[bis(1H-imidazol-2-ylmethyl)amino]methyl}benzyl)-8-isobutyl-2,8-diazaspiro[4.5]decane-3-carboxylate Under an argon atmosphere, the compound (158 mg) obtained in Example 2 and isobutylaldehyde (45.7 mg) were dissolved in acetic acid (0.2 mL) and anhydrous N,N-dimethylformamide (2 mL), and sodium triacetoxyborohydride (134 mg) was added. The reaction solution was stirred at room temperature for 2 hours. To the reaction solution, an aqueous sodium hydrogen carbonate solution was added, followed by extraction with ethyl acetate. The organic layer was washed with saturated brine, dried over anhydrous sodium sulfate and concentrated under reduced pressure. The residue was purified by silica gel chromatography (CHROMATOREX NH (trade name), manufactured by Fuji Silysia Chemical Ltd.) (ethyl acetate:ethanol=1:0→9:1→4:1) to obtain the title compound (113 mg) having the following physical properties.

TLC: Rf 0.29 (dichloromethane:methanol:28% ammonia water=90:10:1);

NMR (CDCl$_3$): δ 0.86 (d, J=6.9 Hz, 6H), 1.24 (t, J=7.2 Hz, 3H), 1.48-1.58 (m, 2H), 1.60-1.83 (m, 4H), 1.94 (dd, J=8.4, 12.9 Hz, 1H), 2.01 (d, J=6.9 Hz, 2H), 2.15-2.35 (m, 5H), 2.93 (d, J=9.3 Hz, 1H), 3.31 (t, J=8.4 Hz, 1H), 3.51 (d, J=12.9 Hz, 1H), 3.60 (s, 4H), 3.62 (s, 2H), 3.83 (d, J=12.9 Hz, 1H), 4.07 (q, J=7.2 Hz, 2H), 7.04 (s, 4H), 7.22-7.30 (m, 4H).

Examples 3(1) to 3(4)

The same procedure as in Example 3 was carried out, except that corresponding compound was used in place of isobutylaldehyde in Example 3, the title compound was obtained.

Example 3(1)

Ethyl 2-(4-{[bis(1H-imidazol-2-ylmethyl)amino]methyl}benzyl)-8-cyclohexyl-2,8-diazaspiro[4.5]decane-3-carboxylate TLC: Rf 0.42 (chloroform:methanol: 28% ammonia water=90:13:2);

NMR (DMSO-d$_6$): δ 1.03-1.18 (m, 8H), 1.36-1.42 (m, 2H), 1.45-1.55 (m, 3H), 1.59-1.72 (m, 5H), 1.85 (dd, J=12.9, 9.0 Hz, 1H), 2.06-2.19 (m, 2H), 2.25-2.40 (m, 4H), 2.72 (d, J=8.8 Hz, 1H), 3.21-3.29 (m, 1H), 3.42 (d, J=13.2 Hz, 1H), 3.46 (s, 2H), 3.54 (s, 4H), 3.80 (d, J=13.2 Hz, 1H), 3.94-4.06 (m, 2H), 6.84 (s, 2H), 7.12 (s, 2H), 7.18-7.26 (m, 2H), 7.27-7.37 (m, 2H), 12.02 (s, 2H).

Example 3(2)

Ethyl 2-(4-{[bis(1H-imidazol-2-ylmethyl)amino]methyl}benzyl)-8-(2,2-dimethylpropyl)-2,8-diazaspiro[4.5]decane-3-carboxylate TLC: Rf 0.29 (dichloromethane:methanol:28% ammonia water=90:10:1);

NMR (CDCl$_3$): δ 0.82 (s, 9H), 1.24 (t, J=7.2 Hz, 3H), 1.40-1.52 (m, 2H), 1.58-1.67 (m, 2H), 1.77 (dd, J=8.1, 12.9 Hz, 1H), 1.94 (dd, J=8.1, 12.9 Hz, 1H), 1.97 (s, 2H), 2.21 (d, J=9.3 Hz, 1H), 2.30-2.48 (m, 4H), 2.94 (d, J=9.3 Hz, 1H), 3.30 (t, J=8.1 Hz, 1H), 3.53 (d, J=12.9 Hz, 1H), 3.61 (s, 4H), 3.64 (s, 2H), 3.83 (d, J=12.9 Hz, 1H), 4.07 (q, J=7.2 Hz, 2H), 7.05 (s, 4H), 7.25-7.32 (m, 4H).

Example 3(3)

Ethyl 8-benzyl-2-(4-{[bis(1H-imidazol-2-ylmethyl)amino]methyl}benzyl)-2,8-diazaspiro[4.5]decane-3-carboxylate TLC: Rf 0.55 (dichloromethane:methanol:28% ammonia water=90:10:1);

NMR (CDCl$_3$): δ 1.23 (t, J=7.1 Hz, 3H), 1.48-1.57 (m, 2H), 1.64-1.72 (m, 2H), 1.79 (dd, J=12.9, 8.0 Hz, 1H), 1.94 (dd, J=12.9, 8.0 Hz, 1H), 2.24 (d, J=9.2 Hz, 1H), 2.26-2.40 (m, 4H), 2.95 (d, J=9.2 Hz, 1H), 3.31 (t, J=8.0 Hz, 1H), 3.44 (s, 2H), 3.55 (d, J=13.0 Hz, 1H), 3.61 (s, 4H), 3.66 (s, 2H), 3.83 (d, J=13.0 Hz, 1H), 4.06 (q, J=7.1 Hz, 2H), 7.05 (s, 4H), 7.18-7.34 (m, 9H).

Example 3(4)

Ethyl 2-(4-{[bis(1H-imidazol-2-ylmethyl)amino]methyl}benzyl)-8-[(3-methyl-2-thienyl)methyl]-2,8-diazaspiro[4.5]decane-3-carboxylate TLC: Rf 0.45 (dichloromethane:methanol:28% ammonia water=90:10:1);
NMR (CDCl$_3$): δ 1.23 (t, J=7.1 Hz, 3H), 1.44-1.73 (m, 4H), 1.79 (dd, J=12.9, 8.1 Hz, 1H), 1.95 (dd, J=12.9, 8.1 Hz, 1H), 2.16 (s, 3H), 2.24 (d, J=9.2 Hz, 1H), 2.28-2.50 (m, 4H), 2.95 (d, J=9.2 Hz, 1H), 3.30 (t, J=8.1 Hz, 1H), 3.55 (d, J=13.0 Hz, 1H), 3.55 (s, 2H), 3.62 (s, 4H), 3.65 (s, 2H), 3.83 (d, J=13.0 Hz, 1H), 4.06 (q, J=7.1 Hz, 2H), 6.76 (d, J=5.1 Hz, 1H), 7.05 (s, 4H), 7.09 (d, J=5.1 Hz, 1H), 7.24-7.34 (m, 4H).

Example 4

Ethyl 2-(4-{[bis(1H-imidazol-2-ylmethyl)amino]methyl}benzyl)-8-(1-ethylpropyl)-2,8-diazaspiro[4.5]decane-3-carboxylate Under an argon atmosphere, to the compound (180 mg) obtained in Example 2, 3-pentanone (0.31 mL) and tetraisopropyltitanate (0.16 mL) were added, followed by stirring at room temperature for 1 hour. To the reaction solution, ethanol (0.37 mL) and sodium borohydride (42 mg) were added, followed by stirring at room temperature for 1 hour. To the reaction solution, an aqueous sodium hydrogen carbonate solution was added, followed by extraction with ethyl acetate. The organic layers were combined, washed with saturated brine, dried over anhydrous sodium sulfate, and concentrated under reduced pressure. The residue was purified by silica gel chromatography (CHROMATOREX NH (trade name), manufactured by Fuji Silysia Chemical Ltd.) (ethyl acetate→ethyl acetate:methanol=30:1→15:1) to obtain the title compound (131 mg) having the following physical properties.
TLC: Rf 0.33 (dichloromethane:methanol:28% ammonia water=90:10:1);
NMR (CDCl$_3$): δ 0.86 (t, J=7.2 Hz, 6H), 1.16-1.34 (m, 5H), 1.36-1.55 (m, 4H), 1.62 (t, J=5.4 Hz, 2H), 1.77 (dd, J=8.1, 12.9 Hz, 1H), 1.94 (dd, J=8.1, 12.9 Hz, 1H), 2.09 (m, 1H), 2.31 (d, J=9.3 Hz, 1H), 2.30-2.48 (m, 4H), 2.95 (d, J=9.3 Hz, 1H), 3.30 (t, J=8.1 Hz, 1H), 3.55 (d, J=12.9 HZ, 1H), 3.61 (s, 4H), 3.65 (s, 2H), 3.84 (d, J=12.9 Hz, 1H), 4.07 (q, J=7.2 Hz, 2H), 7.06 (s, 4H), 7.25-7.32 (m, 4H).

Example 5

2-(4-{[bis(1H-imidazol-2-ylmethyl)amino]methyl}benzyl)-8-isobutyl-2,8-diazaspiro[4.5]decane-3-carboxylic acid To an ethanol (1 mL) solution of the compound (111 mg) synthesized in Example 3, an aqueous 2N sodium hydroxide solution (0.2 mL) was added, followed by stirring at 80° C. for 2 hours. The reaction solution was neutralized with 2N hydrochloric acid and concentrated under reduced pressure. The residue was dissolved in ethanol and an insoluble substance was removed by filtration. The filtrate was concentrated under reduced pressure and the residue was purified by silica gel chromatography (CHROMATOREX NH (trade name), manufactured by Fuji Silysia Chemical Ltd.) (ethyl acetate dichloromethane:methanol=20:1→4:1) to obtain the title compound (98.2 mg) having the following physical properties.
TLC: Rf 0.29 (dichloromethane:methanol:28% ammonia water=40:10:1);
NMR (CD$_3$OD): δ 0.88 (d, J=6.6 Hz, 6H), 1.50-1.60 (m, 2H), 1.64-1.72 (m, 2H), 1.75-1.87 (m, 2H), 2.05 (dd, J=9.1, 12.9 Hz, 1H), 2.14 (d, J=6.6 Hz, 2H), 2.26-2.48 (m, 5H), 2.97 (d, J=9.9 Hz, 1H), 3.50 (s, 2H), 3.60 (m, 1H), 3.65 (s, 4H), 4.14 (d, J=12.9 Hz, 1H), 6.99 (s, 4H), 7.30 (d, J=8.1 Hz, 2H), 7.36 (d, J=8.1 Hz, 2H).

Example 5(1) to 5(5)

The same procedure as in Example 5 was carried out, except that corresponding compound was used in place of the compound obtained in Example 3, the following title compound was obtained.

Example 5(1)

2-(4-{[bis(1H-imidazol-2-ylmethyl)amino]methyl}benzyl)-8-cyclohexyl-2,8-diazaspiro[4.5]decane-3-carboxylic acid TLC: Rf 0.14 (chloroform:methanol: 28% ammonia water=90:13:2);
NMR (CD$_3$OD): δ 0.90-1.48 (m, 6H), 1.52-2.01 (m, 9H), 2.02-2.21 (m, 1H), 2.25-2.53 (m, 1H), 2.57-2.91 (m, 5H), 2.94-3.10 (m, 1H), 3.19-3.42 (m, 1H), 3.51 (s, 2H), 3.57-3.80 (m, 5H), 4.02-4.21 (m, 1H), 6.99 (s, 4H), 7.21-7.43 (m, 4H).

Example 5(2)

2-(4-{[bis(1H-imidazol-2-ylmethyl)amino]methyl}benzyl)-8-(2,2-dimethylpropyl)-2,8-diazaspiro[4.5]decane-3-carboxylic acid TLC: Rf 0.32 (dichloromethane:methanol:28% ammonia water=40:10:1);
NMR (CD$_3$OD): δ 0.85 (s, 9H), 1.45-1.68 (m, 4H), 1.84 (dd, J=8.7, 12.9 Hz, 1H), 2.04 (s, 2H), 2.10 (dd, J=8.7, 12.9 Hz, 1H), 2.30-2.65 (m, 5H), 3.12 (d, J=10.5 Hz, 1H), 3.51 (s, 2H), 3.66 (s, 4H), 3.83 (m, 1H), 4.22 (d, J=12.9 Hz, 1H), 6.99 (s, 4H), 7.34 (d, J=8.1 Hz, 2H), 7.39 (d, J=8.1 Hz, 2H).

Example 5(3)

8-benzyl-2-(4-{[bis(1H-imidazol-2-ylmethyl)amino]methyl}benzyl)-2,8-diazaspiro[4.5]decane-3-carboxylic acid TLC: Rf 0.45 (dichloromethane:methanol:28% ammonia water=80:20:2);
NMR (DMSO-d$_6$): δ 1.37-1.57 (m, 4H), 1.66-1.77 (m, 1H), 1.84-1.97 (m, 1H), 2.10-2.34 (m, 5H), 2.90 (d, J=10.3 Hz, 1H), 3.11-3.66 (m, 1H), 3.98 (d, J=13.0 Hz, 1H), 6.86-7.09 (m, 4H), 7.13-7.38 (m, 9H).

Example 5(4)

2-(4-{[bis(1H-imidazol-2-ylmethyl)amino]
methyl}benzyl)-8-[(3-methyl-2-thienyl)methyl]-2,8-
diazaspiro[4.5]decane-3-carboxylic acid TLC: Rf 0.32 (dichloromethane:methanol:28% ammonia water=80:20:2);
NMR (DMSO-$d_6$): δ 1.35-1.56 (m, 4H), 1.63-1.92 (m, 2H), 2.06-2.17 (m, 4H), 2.17-2.38 (m, 4H), 2.77-2.87 (m, 1H), 3.11-3.62 (m, 10H), 3.98-4.09 (m, 1H), 6.76 (d, J=5.1 Hz, 1H), 6.95 (s, 4H), 7.17-7.37 (m, 5H).

Example 5(5)

2-(4-{[bis(1H-imidazol-2-ylmethyl)amino]
methyl}benzyl)-8-(1-ethylpropyl)-2,8-diazaspiro
[4.5]decane-3-carboxylic acid TLC: Rf 0.26 (dichloromethane:methanol:28% ammonia water=40:10:1);
NMR (CD$_3$OD): δ 0.92 (t, J=7.2 Hz, 6H), 1.25-1.80 (m, 8H), 1.87 (dd, J=9.1, 12.9 Hz, 1H), 2.14 (dd, J=9.1, 12.9 Hz, 1H), 2.35 (m, 1H), 2.52-2.78 (m, 5H), 3.14 (m, 1H), 3.51 (s, 2H), 3.56 (m, 1H), 3.66 (s, 4H), 3.85 (m, 1H), 4.22 (d, J=12.9 Hz, 1H), 6.99 (s, 4H), 7.34 (d, J=8.1 Hz, 2H), 7.39 (d, J=8.1 Hz, 2H).

Example 6

2-({[4-(hydroxymethyl)benzyl]amino}methyl)-N,N-
dimethyl-1H-imidazole-1-sulfonamide To an anhydrous methanol (40 mL) solution of 2-formyl-N,N-dimethyl-1H-imidazole-1-sulfonamide (International Publication WO 2007/049771 pamphlet, Example 64; 5.52 g) and 4-(aminomethyl)phenyl]methanol (CAS Registry Number: 39895-56-2; 2.48 mg), trimethyl orthoformate (3.96 mL) was added under an argon atmosphere. The reaction solution was stirred at room temperature for 31 hours. To the reaction solution, sodium borohydride (1.37 g) was added at 0° C., followed by stirring for 30 minutes. To the reaction solution, water was added, and then solvent was concentrated under reduced pressure. The aqueous layer was extracted three times with dichloromethane. The organic layers were combined, washed with saturated brine, dried over anhydrous magnesium sulfate and concentrated under reduces pressure. The residue was purified by silica gel chromatography (ethyl acetate:methanol:10% ammonia water=1:0:0→90:10:0→80:20:1) to obtain the title compound having the following physical properties (3.78 g).

TLC: Rf 0.52 (chloroform:methanol=9:1);
NMR (CDCl$_3$): δ 2.87 (s, 6H), 3.83 (s, 2H), 4.07 (s, 2H), 4.67 (s, 2H), 7.00 (d, J=1.5 Hz, 1H), 7.24 (d, J=1.5 Hz, 1H), 7.29-7.35 (m, 4H).

Example 7

2-({[4-(hydroxymethyl)benzyl][(1-methyl-1H-imi-
dazol-2-yl)methyl]amino}methyl)-N,N-dimethyl-
1H-imidazole-1-sulfonamide In the same procedure as in Example 3, except that the compound obtained in Example 6 was used in place of the compound obtained in Example 2 and 1-methyl-1H-imidazole-2-carboaldehyde (CAS Registry Number: 13750-81-7) was used in place of isobutylaldehyde in Example 3, the title compound having the following physical properties was obtained.

TLC: Rf 0.42 (dichloromethane:methanol:28% ammonia water=90:10:1);
NMR (CDCl$_3$): δ 2.73 (s, 6H), 3.53 (s, 3H), 3.78 (s, 2H), 3.82 (s, 2H), 3.91 (s, 2H), 4.66 (s, 2H), 6.78 (s, 1H), 6.86 (s, 1H), 7.01 (s, 1H), 7.17-7.36 (m, 5H).

Example 8

2-({(4-formylbenzyl)[(1-methyl-1H-imidazol-2-yl)
methyl]amino}methyl)-N,N-dimethyl-1H-imidazole-
1-sulfonamide To a dimethyl sulfoxide (7 mL)-dichloromethane (7 mL) solution of the compound (1.98 g) obtained in Example 7 and triethylamine (3.30 mL), a sulfur trioxide-pyridine complex (2.26 g) was added at 0° C. The reaction solution was stirred for 1 hour and then water was added. The mixed solution was extracted twice with ethyl acetate and then washed with saturated brine. The organic layer was dried over anhydrous magnesium sulfate and then concentrated under reduced pressure to obtain the title compound (2.16 g) having the following physical properties.

TLC: Rf 0.45 (dichloromethane:methanol:28% ammonia water=90:10:1);
NMR (CDCl$_3$): δ 2.81 (s, 6H), 3.57 (s, 3H), 3.93 (s, 2H), 4.02 (s, 2H), 4.04 (s, 2H), 6.77 (d, J=1.3 Hz, 1H), 7.01 (d, J=1.7 Hz, 1H), 7.04 (d, J=1.3 Hz, 1H), 7.23 (d, J=1.7 Hz, 1H), 7.48 (d, J=8.2 Hz, 2H), 7.78 (d, J=8.2 Hz, 2H), 9.96 (s, 1H).

Example 9

8-tert-butyl 3-ethyl 2-[4-({({1-[(dimethylamino)
sulfonyl]-1H-imidazol-2-yl}methyl)[(1-methyl-1H-
imidazol-2-yl)methyl]amino}methyl)benzyl]-2,8-
diazaspiro[4.5]decane-3,8-dicarboxylate The same procedure as in Example 1 was carried out, except that the compound obtained in Example 8 was used in place of 4-{[bis(1H-imidazol-2-ylmethyl)amino] methyl}benzaldehyde in Example 1, the title compound having the following physical properties was obtained.

TLC: Rf 0.48 (dichloromethane:methanol:28% ammonia water=90:10:1);
NMR (CDCl$_3$): δ 1.26 (t, J=6.7 Hz, 3H), 1.42-1.44 (m, 11H), 1.55-1.65 (m, 2H), 1.78-2.01 (m, 2H), 2.20 (d, J=9.1 Hz, 1H), 2.74 (s, 6H), 2.86 (d, J=9.1 Hz, 1H), 3.24-3.39 (m, 5H), 3.45 (d, J=13.1 Hz, 1H), 3.53 (s, 3H), 3.78 (s, 2H), 3.83 (s, 2H), 3.89-3.98 (m, 3H), 4.14 (q, J=6.7 Hz, 2H), 6.79 (d, J=1.2 Hz, 1H), 6.87 (d, J=1.2 Hz, 1H), 7.01 (d, J=1.7 Hz, 1H), 7.20-7.31 (m, 5H).

Example 10

Ethyl 2-[4-({(1H-imidazol-2-ylmethyl)[(1-methyl-
1H-imidazol-2-yl)methyl]amino}methyl)benzyl]-2,
8-diazaspiro[4.5]decane-3-carboxylate The same procedure as in Example 2 was carried out, except that the compound obtained in Example 9 was used in place of the compound obtained in Example 1 in Example 2, the title compound having the following physical properties was obtained.

TLC: Rf 0.43 (dichloromethane:methanol:28% ammonia water=80:20:1);

NMR (CDCl$_3$): δ 1.25 (t, J=6.9 Hz, 3H), 1.44-1.54 (m, 2H), 1.61-1.69 (m, 2H), 1.84 (dd, J=12.9, 7.5 Hz, 1H), 1.97 (dd, J=12.9, 8.5 Hz, 1H), 2.21 (d, J=9.1 Hz, 1H), 2.68-2.85 (m, 4H), 2.92 (d, J=9.1 Hz, 1H), 3.35 (dd, J=8.5, 7.5 Hz, 1H), 3.43-3.52 (m, 3H), 3.55 (s, 3H), 3.62 (s, 2H), 3.67 (s, 2H), 3.94 (d, J=13.1 Hz, 1H), 4.08-4.18 (m, 2H), 6.87 (d, J=1.3 Hz, 1H), 6.99 (d, J=1.3 Hz, 1H), 7.09 (s, 2H), 7.25-7.38 (m, 4H).

Example 11 ethyl 2-[4-({(1H-imidazol-2-ylmethyl)[(1-methyl-1H-imidazol-2-yl)methyl]amino}methyl)benzyl]-8-isobutyl-2,8-diazaspiro[4.5]decane-3-carboxylate The same procedure as in Example 3 was carried out, except that the compound obtained in Example 10 was used in place of the compound obtained in Example 2 in Example 3, the title compound having the following physical properties was obtained.

TLC: Rf 0.61 (dichloromethane:methanol:28% ammonia water=90:10:1);

NMR (CDCl$_3$): δ 0.86 (d, J=6.5 Hz, 6H), 1.25 (t, J=7.1 Hz, 3H), 1.46-1.55 (m, 2H), 1.59-1.85 (m, 4H), 1.89-2.04 (m, 3H), 2.15-2.35 (m, 5H), 2.89 (d, J=9.2 Hz, 1H), 3.32 (t, J=8.1 Hz, 1H), 3.43-3.52 (m, 3H), 3.55 (s, 3H), 3.62 (s, 2H), 3.68 (s, 2H), 3.92 (d, J=13.3 Hz, 1H), 4.06-4.18 (m, 2H), 6.87 (d, J=1.3 Hz, 1H), 7.00 (d, J=1.3 Hz, 1H), 7.06-7.16 (m, 2H), 7.27-7.38 (m, 4H), 12.31 (s, 1H).

Example 11(1) to Example 11(2)

The same procedure as in Example 11 was carried out, except that corresponding compound was used in place of isobutylaldehyde in Example 11, the following title compound was obtained.

Example 11(1)

Ethyl 8-cyclohexyl-2-[4-({(1H-imidazol-2-ylmethyl)[(1-methyl-1H-imidazol-2-yl)methyl]amino}methyl)benzyl]-2,8-diazaspiro[4.5]decane-3-carboxylate TLC: Rf 0.82 (chloroform:methanol: 28% ammonia water=40:10:2);

NMR (CDCl$_3$): δ 0.78-1.34 (m, 6H), 1.25 (t, J=6.8 Hz, 3H), 1.36-2.03 (m, 10H), 2.11-2.33 (m, 1H), 2.20 (d, J=9.2 Hz, 1H), 2.34-2.65 (m, 4H), 2.89 (d, J=9.2 Hz, 1H), 3.33 (t, J=8.1 Hz, 1H), 3.46 (s, 2H), 3.43-3.58 (m, 1H), 3.55 (s, 3H), 3.61 (s, 2H), 3.68 (s, 2H), 3.92 (d, J=13.2 Hz, 1H), 4.12 (q, J=6.8 Hz, 2H), 6.77-6.93 (m, 1H), 6.94-7.06 (m, 1H), 7.03-7.19 (m, 2H), 7.17-7.46 (m, 4H).

Example 11(2)

Ethyl 8-(2,2-dimethylpropyl)-2-[4-({(1H-imidazol-2-ylmethyl)[(1-methyl-1H-imidazol-2-yl)methyl]amino}methyl)benzyl]-2,8-diazaspiro[4.5]decane-3-carboxylate TLC: Rf 0.61 (dichloromethane:methanol:28% ammonia water=90:10:1);

NMR (CDCl$_3$): δ 0.82 (s, 9H), 1.25 (t, J=7.1 Hz, 3H), 1.42-1.52 (m, 2H), 1.59-1.71 (m, 2H), 1.79 (dd, J=12.8, 8.0 Hz, 1H), 1.88-1.99 (m, 3H), 2.18 (d, J=9.2 Hz, 1H), 2.27-2.46 (m, 4H), 2.89 (d, J=9.2 Hz, 1H), 3.32 (t, J=8.0 Hz, 1H), 3.43-3.50 (m, 3H), 3.55 (s, 3H), 3.62 (s, 2H), 3.68 (s, 2H), 3.92 (d, J=13.1 Hz, 1H), 4.07-4.18 (m, 2H), 6.87 (d, J=1.2 Hz, 1H), 7.00 (d, J=1.2 Hz, 1H), 7.06-7.15 (m, 2H), 7.27-7.37 (m, 4H), 12.31 (s, 1H).

Example 12

Ethyl 8-(1-ethylpropyl)-2-[4-({(1H-imidazol-2-ylmethyl)[(1-methyl-1H-imidazol-2-yl)methyl]amino}methyl)benzyl]-2,8-diazaspiro[4.5]decane-3-carboxylate The same procedure as in Example 4 was carried out, except that the compound obtained in Example 10 was used in place of the compound obtained in Example 2 in Example 4, the title compound having the following physical properties was obtained.

TLC: Rf 0.61 (dichloromethane:methanol:28% ammonia water=90:10:1);

NMR (CDCl$_3$): δ 0.85 (t, J=7.4 Hz, 6H), 1.16-1.32 (m, 5H), 1.34-1.51 (m, 4H), 1.57-1.65 (m, 2H), 1.73-1.85 (m, 1H), 1.87-1.99 (m, 1H), 2.02-2.13 (m, 1H), 2.18 (d, J=9.2 Hz, 1H), 2.27-2.47 (m, 4H), 2.89 (d, J=9.2 Hz, 1H), 3.32 (t, J=8.1 Hz, 1H), 3.41-3.51 (m, 3H), 3.54 (s, 3H), 3.63 (s, 2H), 3.67 (s, 2H), 3.92 (d, J=13.3 Hz, 1H), 4.06-4.17 (m, 2H), 6.87 (d, J=1.2 Hz, 1H), 7.00 (d, J=1.2 Hz, 1H), 7.05-7.15 (m, 2H), 7.24-7.38 (m, 4H), 12.31 (s, 1H).

Example 13

2-[4-({(1H-imidazol-2-ylmethyl)[(1-methyl-1,1-imidazol-2-yl)methyl]amino}methyl)benzyl]-8-isobutyl-2,8-diazaspiro[4.5]decane-3-carboxylic acid The same procedure as in Example 5 was carried out, except that the compound obtained in Example 11 was used in place of the compound obtained in Example 3 in Example 5, the title compound having the following physical properties was obtained.

TLC: Rf 0.28 (dichloromethane:methanol:28% ammonia water=80:20:1);

TLC: NMR (CD$_3$OD): δ 0.90 (d, J=6.5 Hz, 6H), 1.56-1.75 (m, 4H), 1.78-2.02 (m, 2H), 2.12-2.29 (m, 3H), 2.37-2.62 (m, 4H), 2.65-2.75 (m, 1H), 3.16-3.25 (m, 1H), 3.49 (s, 3H), 3.53 (s, 2H), 3.57-3.70 (m, 5H), 3.88-4.00 (m, 1H), 4.20-4.29 (m, 1H), 6.83 (d, J=1.3 Hz, 1H), 6.96 (d, J=1.3 Hz, 1H), 7.00 (s, 2H), 7.29 (d, J=8.1 Hz, 2H), 7.39 (d, J=8.1 Hz, 2H).

Example 13(1) to 13(3)

The same procedure as in Example 13 was carried out, except that corresponding compound was used in place of the compound obtained in Example 11 in Example 13, the following title compound was obtained.

Example 13(1)

8-cyclohexyl-2-[4-({(1H-imidazol-2-ylmethyl)[(1-methyl-1H-imidazol-2-yl)methyl]amino}methyl)benzyl]-2,8-diazaspiro[4.5]decane-3-carboxylic acid Rf 0.29 (chloroform:methanol: 28% ammonia water=40:10:2);

NMR (CD$_3$OD): δ ppm 0.93-1.50 (m, 6H), 1.57-2.09 (m, 9H), 2.10-2.25 (m, 1H), 2.57-2.72 (m, 1H), 2.74-3.07 (m, 5H), 3.10-3.22 (m, 1H), 3.42-3.60 (m, 7H), 3.65 (s, 3H), 3.80-3.91 (m, 1H), 4.20 (d, J=12.6 Hz, 1H), 6.83 (d, J=1.3 Hz, 1H), 6.97 (d, J=1.3 Hz, 1H), 7.00 (s, 2H), 7.28 (d, J=8.1 Hz, 2H), 7.38 (d, J=8.1 Hz, 2H).

Example 13(2)

8-(2,2-dimethylpropyl)-2-[4-({(1H-imidazol-2-ylmethyl)[(1-methyl-1H-imidazol-2-yl)methyl]amino}methyl)benzyl]-2,8-diazaspiro[4.5]decane-3-carboxylic acid TLC: Rf 0.33 (dichloromethane:methanol:28% ammonia water=80:20:1);
NMR (CD$_3$OD): δ 0.86 (s, 9H), 1.52-1.73 (m, 4H), 1.94-2.05 (m, 1H), 2.10 (s, 2H), 2.18-2.32 (m, 1H), 2.39-2.61 (m, 4H), 2.88-2.99 (m, 1H), 3.33-3.41 (m, 1H), 3.49 (s, 3H), 3.54 (s, 2H), 3.60-3.70 (m, 4H), 3.77-3.88 (m, 1H), 4.14-4.23 (m, 1H), 4.26-4.36 (m, 1H), 6.83 (d, J=1.3 Hz, 1H), 6.96 (d, J=1.3 Hz, 1H), 7.00 (s, 2H), 7.32 (d, J=8.1 Hz, 2H), 7.43 (d, J=8.1 Hz, 2H).

Example 13(3)

8-(1-ethylpropyl)-2-[4-({(1H-imidazol-2-ylmethyl)[(1-methyl-1H-imidazol-2-yl)methyl]amino}methyl)benzyl]-2,8-diazaspiro[4.5]decane-3-carboxylic acid TLC: Rf 0.58 (dichloromethane:methanol:28% ammonia water=80:20:4);
NMR (CD$_3$OD): δ 0.91 (t, J=7.4 Hz, 6H), 1.31-1.47 (m, 2H), 1.49-1.76 (m, 6H), 1.81-1.94 (m, 1H), 2.06-2.18 (m, 1H), 2.26-2.38 (m, 1H), 2.44-2.73 (m, 5H), 3.05-3.13 (m, 1H), 3.45-3.50 (m, 4H), 3.52 (s, 2H), 3.64 (s, 2H), 3.65 (s, 2H), 3.70-3.84 (m, 1H), 4.18 (d, J=12.8 Hz, 1H), 6.82 (d, J=1.2 Hz, 1H), 6.96 (d, J=1.2 Hz, 1H), 6.99 (s, 2H), 7.27 (d, J=8.1 Hz, 2H), 7.38 (d, J=8.1 Hz, 2H).

Example 14

1-propyl-1H-imidazole-2-carboaldehyde

To 1H-imidazole-2-carboaldehyde (800 mg), N-methylpyrrolidone (10 mL) was added, followed by dissolution with heating. To this solution, 1-bromopropane (2.05 g) and potassium carbonate (1.15 g) were added. The reaction solution was stirred at 40° C. for 12 hours. To the reaction solution, water (10 mL) was added. The aqueous layer was extracted twice with ethyl acetate. The organic layers were combined, washed with saturated brine and then dried over anhydrous sodium sulfate and concentrated under reduced pressure. The residue was purified by silica gel chromatography (dichloromethane) to obtain the title compound (893 mg) having the following physical properties.
TLC: Rf 0.73 (chloroform:methanol: 28% ammonia water=90:10:1).
NMR (CDCl$_3$): δ 0.90-0.96 (m, 3H), 1.75-1.89 (m, 2H), 4.32-4.40 (m, 2H), 7.14-7.16 (m, 1H), 7.27-7.29 (m, 1H), 9.80-9.82 (m, 1H).

Example 15

Benzyl({1-[(dimethylamino)sulfonyl]-1H-imidazol-2-yl}methyl)[4-(hydroxymethyl)benzyl]carbamate The compound obtained in Example 6 (2.55 g) was dissolved in water (8 mL) and tetrahydrofuran (8 mL), and sodium carbonate (2.5 g) was added. Benzyl chloroformate (2.68 g) was added at 0° C. The reaction solution was stirred at room temperature for 14 hours. To the reaction solution, water (30 mL) was added. The aqueous layer was extracted twice with dichloromethane. The organic layers were combined and washed with saturated brine and then dried over anhydrous sodium sulfate and the solvent was concentrated under reduced pressure. The residue was purified by silica gel chromatography (hexane:ethyl acetate=1:1→0:1) to obtain the title compound (1.23 g) having the following physical properties.
TLC: Rf 0.80 (chloroform:methanol: 28% ammonia water=40:10:2);
NMR (CDCl$_3$): δ 2.52 (s, 3H), 2.85-2.93 (m, 3H), 4.67 (s, 2H), 4.69 (s, 2H), 4.75 (s, 2H), 5.01-5.27 (m, 2H), 7.04 (d, J=1.6 Hz, 1H), 7.15-7.40 (m, 10H).

Example 16

Benzyl({1-[(dimethylamino)sulfonyl]-1H-imidazol-2-yl}methyl)(4-formylbenzyl)carbamate The same procedure as in Example 8 was carried out, except that the compound obtained in Example 15 was used in place of the compound obtained in Example 7 in Example 8, the title compound having the following physical properties was obtained.
TLC: Rf 0.55 (ethyl acetate);
NMR (CDCl$_3$): δ 2.49-2.59 (m, 3H), 2.86-2.95 (m, 3H), 4.48-4.92 (m, 4H), 5.05-5.26 (m, 2H), 7.03 (d, J=1.6 Hz, 1H), 7.12-8.07 (m, 10H), 9.99 (s, 1H).

Example 17

8-tert-butyl 3-ethyl 2-(4-{[[(benzyloxy)carbonyl]({1-[(dimethylamino)sulfonyl]-1H-imidazol-2-yl}methyl)amino]methyl}benzyl)-2,8-diazaspiro[4.5]decane-3,8-dicarboxylate The same procedure as in Example 1 was carried out, except that the compound obtained in Example 16 was used in place of 4-{[bis(1H-imidazol-2-ylmethyl)amino]methyl}benzaldehyde in Example 1, the title compound having the following physical properties were obtained.
TLC: Rf 0.61 (ethyl acetate);
NMR (CDCl$_3$): δ 1.25 (t, J=7.1 Hz, 3H), 1.43 (s, 9H), 1.43-1.49 (m, 2H), 1.55-1.68 (m, 2H), 1.77-2.04 (m, 2H), 2.14-2.26 (m, 1H), 2.47-2.58 (m, 3H), 2.88-3.01 (m, 3H), 3.25-3.46 (m, 5H), 3.49 (d, J=5.5 Hz, 4H), 3.94 (d, J=13.2 Hz, 1H), 4.14 (q, J=7.1 Hz, 2H), 4.36-4.85 (m, 4H), 4.94-5.32 (m, 2H), 7.04 (d, J=1.6 Hz, 1H), 7.11-7.43 (m, 10H).

Example 18

Ethyl 2-(4-{[[(benzyloxy)carbonyl](1H-imidazol-2-ylmethyl)amino]methyl}benzyl)-2,8-diazaspiro[4.5]decane-3-carboxylate The same procedure as in Example 2 was carried out, except that the compound obtained in Example 17 was used in place of the compound obtained in Example 1 in Example 2, the title compound having the following physical properties was obtained.
TLC: Rf 0.11 (ethyl acetate);

Example 19

Ethyl 2-(4-{[[(benzyloxy)carbonyl](1H-imidazol-2-ylmethyl)amino]methyl}benzyl)-8-isobutyl-2,8-diazaspiro[4.5]decane-3-carboxylate The same procedure as in Example 3 was carried out, except that the compound obtained in Example 18 was used in place of the compound obtained in Example 2 in Example 3, the title compound having the following physical properties was obtained.

TLC: Rf 0.57 (chloroform:methanol: 28% ammonia water=90:10:1).

Example 20

Ethyl 2-(4-{[(1H-imidazol-2-ylmethyl)amino]methyl}benzyl)-8-isobutyl-2,8-diazaspiro[4.5]decane-3-carboxylate The compound obtained in Example 19 was dissolved in ethyl acetate (30 mL) and hydrous 10% palladium-carbon (250 mg) was added, followed by stirring under a hydrogen atmosphere for 30 minutes. After filtering with Celite (trade name), the solvent was concentrated under reduced pressure. The residue was purified by silica gel chromatography (hexane:ethyl acetate=10:1→1:1) to obtain the title compound (297 mg) having the following physical properties.

TLC: Rf 0.76 (chloroform:methanol: 28% ammonia water=40:10:2);

NMR (CDCl$_3$): δ 0.86 (d, J=6.6 Hz, 6H), 1.25 (t, J=7.1 Hz, 3H), 1.38-2.06 (m, 12H), 2.89 (d, J=9.0 Hz, 1H), 3.32 (t, J=8.1 Hz, 2H), 3.47 (d, J=13.2 Hz, 1H), 3.74-3.79 (m, 3H), 3.87-3.97 (m, 3H), 4.07-4.17 (m, 2H), 6.98 (s, 1H), 7.11-7.37 (m, 5H).

Example 21

Ethyl 2-[4-({(1H-imidazol-2-ylmethyl)[(1-propyl-1H-imidazol-2-yl)methyl]amino}methyl)benzyl]-8-isobutyl-2,8-diazaspiro[4.5]decane-3-carboxylate The same procedure as in Example 3 was carried out, except that the compound obtained in Example 20 was used in place of the compound obtained in Example 2 and the compound obtained in Example 14 was used in place of isobutylaldehyde in Example 3, the title compound having the following physical properties was obtained.

TLC: Rf 0.76 (chloroform:methanol: 28% ammonia water=40:10:2);

Example 22

2-[4-({(1H-imidazol-2-ylmethyl)[(1-propyl-1H-imidazol-2-yl)methyl]amino}methyl)benzyl]-8-isobutyl-2,8-diazaspiro[4.5]decane-3-carboxylic acid The same procedure as in Example 5 was carried out, except that the compound obtained in Example 21 was used in place of the compound obtained in Example 3 in Example 5, the title compound having the following physical properties was obtained.

TLC: Rf 0.58 (chloroform:methanol: 28% ammonia water=40:10:2);

NMR (CD$_3$OD): δ 0.76 (t, J=7.4 Hz, 3H), 0.91 (d, J=6.6 Hz, 6H), 1.46-1.76 (m, 5H), 1.77-2.06 (m, 4H), 2.12-2.31 (m, 3H), 2.35-2.66 (m, 4H), 2.37-2.66 (m, 1H), 3.21-3.32 (m, 1H), 3.54 (s, 2H), 3.62 (s, 2H), 3.65 (s, 2H), 3.82 (t, J=6.9 Hz, 2H), 3.89-4.02 (m, 1H), 4.22-4.31 (m, 1H), 6.86 (d, J=1.3 Hz, 1H), 6.99-7.01 (m, 2H), 7.02 (d, J=1.3 Hz, 1H), 7.27-7.36 (m, 2H), 7.37-7.48 (m, 2H).

Example 22(1) to 22(3)

The same procedure as in Example 14→Example 21→Example 22 was carried out, except that corresponding compound was used in place of 1-bromopropane in Example 14, the following title compound was obtained.

Example 22(1)

2-[4-({(1H-imidazol-2-ylmethyl)[(1-isobutyl-1H-imidazol-2-yl)methyl]amino}methyl)benzyl]-8-isobutyl-2,8-diazaspiro[4.5]decane-3-carboxylic acid TLC: Rf 0.58 (chloroform:methanol: 28% ammonia water=40:10:2);

NMR (CD$_3$OD): δ 0.67-0.74 (m, 6H), 0.91 (d, J=6.6 Hz, 6H), 1.58-1.75 (m, 5H), 1.77-2.01 (m, 4H), 2.13-2.34 (m, 3H), 2.37-2.63 (m, 4H), 2.66-2.83 (m, 1H), 3.17-3.38 (m, 1H), 3.53 (s, 2H), 3.60 (s, 2H), 3.65 (s, 2H), 3.68 (d, J=7.7 Hz, 2H), 3.82-4.07 (m, 1H), 4.21-4.36 (m, 1H), 6.86 (d, J=1.3 Hz, 1H), 7.00 (d, J=1.3 Hz, 1H), 7.01-7.02 (m, 2H), 7.24-7.37 (m, 2H), 7.38-7.54 (m, 2H).

Example 22(2)

2-(4-{[{[1-(cyclopropylmethyl)-1H-imidazol-2-yl]methyl}(1H-imidazol-2-ylmethyl)amino]methyl}benzyl)-8-isobutyl-2,8-diazaspiro[4.5]decane-3-carboxylic acid TLC: Rf 0.58 (chloroform:methanol: 28% ammonia water=40:10:2);

NMR (CDCl$_3$): δ 0.18-0.44 (m, 2H), 0.43-0.69 (m, 2H), 0.85 (d, J=6.4 Hz, 6H), 0.99-1.38 (m, 1H), 1.41-1.84 (m, 5H), 1.85-2.11 (m, 4H), 2.12-2.94 (m, 7H), 3.04-3.23 (m, 1H), 3.33-3.84 (m, 8H), 3.87-4.00 (m, 1H), 6.92-7.11 (m, 4H), 7.28-7.35 (m, 4H).

Example 22(3)

2-(4-{[{[1-(2,2-dimethylpropyl)-1H-imidazol-2-yl]methyl}(1H-imidazol-2-ylmethyl)amino]methyl}benzyl)-8-isobutyl-2,8-diazaspiro[4.5]decane-3-carboxylic acid TLC: Rf 0.59 (chloroform:methanol: 28% ammonia water=40:10:2);

NMR (CD$_3$OD): δ 0.72 (s, 9H), 0.91 (d, J=6.8 Hz, 6H), 1.51-2.01 (m, 5H), 2.07-2.73 (m, 11H), 3.12-3.96 (m, 9H), 4.15-4.39 (m, 1H), 6.86 (d, J=1.1 Hz, 1H), 6.95-7.11 (m, 3H), 7.26-7.36 (m, 2H), 7.38-7.52 (m, 2H).

Example 23

8-tert-butyl 3-ethyl
(3R)-2,8-diazaspiro[4.5]decane-3,8-dicarboxylate

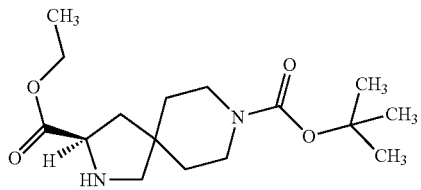

[Chemical Formula 30]

8-tert-butyl 3-ethyl 2,8-diazaspiro[4.5]decane-3,8-dicarboxylate (Japanese Unexamined Patent Publication (Kokai) No. 2004-002470, Example 21f; 25.0 g) and (S)-(+)-camphorsulfonic acid (18.6 g) were dissolved in acetonitrile (100 mL) and concentrated under reduced pressure. To the residue, methyl-tert-butyl ether (250 mL) was added and recrystallization was carried out by being left to stand at room temperature, and then a crystal was filtered (the crystal is used in Example 24). The filtrate was concentrated under reduced pressure and the resultant residue was diluted with a mixed solution of an aqueous saturated sodium hydrogen carbonate solution and saturated brine, and then extracted three times with ethyl acetate. The organic layer was washed with a mixed solution of an aqueous saturated sodium hydrogen carbonate solution and saturated brine, dried over anhydrous magnesium sulfate and concentrated under reduced pressure. To the residue, (R)-(−)-camphorsulfonic acid (8.97 g) was added and the mixture was dissolved in acetonitrile (121 mL) and then concentrated under reduced pressure. To the residue, a mixed solution of acetonitrile (4 mL) and methyl-tert-butyl ether (121 mL) were added and crystallization was carried out by being left to stand at room temperature, and then a crystal (9.98 g) was filtered. The resultant crystal was dissolved by heating at 60° C. in a mixed solution of methyl-tert-butyl ether (425 mL) and acetonitrile (85 mL). The solution was recrystallized by being left to stand at room temperature, and a crystal (6.18 g) was filtered. The resultant crystal was diluted with a mixed solution of an aqueous saturated sodium hydrogen carbonate solution and saturated brine, and then extracted five times with ethyl acetate. The organic layer was washed with a mixed solution of an aqueous saturated sodium hydrogen carbonate solution and saturated brine. The organic layer was dried over anhydrous sodium sulfate and concentrated under reduced pressure to obtain the title compound (3.63 g, 99% ee) having the following physical properties. Optical purity was confirmed using a high-performance liquid chromatography (HPLC).

Column: CHIRALPAK AD-H (0.46 cmϕ×25 cm L, manufactured by Daicel Chemical Industries Limited.);
Eluent: n-hexane:ethanol:diethylamine=80:20:0.1;
Flow rate: 1 mL/minute;
Detection wavelength: 210 nm.
HPLC retention time: 7.0 minutes;
Specific rotation: $[\alpha]_D^{25}$=+14.3 (c=0.52, chloroform).

Example 24

8-tert-butyl 3-ethyl
(3S)-2,8-diazaspiro[4.5]decane-3,8-dicarboxylate

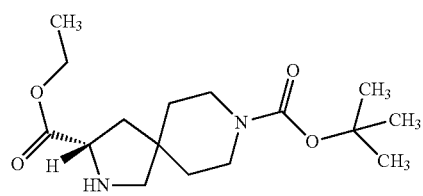

[Chemical Formula 31]

8-tert-butyl 3-ethyl 2,8-diazaspiro[4.5]decane-3,8-dicarboxylate (Japanese Unexamined Patent Publication (Kokai) No. 2004-002470, Example 21f; 25.0 g) and (S)-(+)-camphorsulfonic acid (18.6 g) were dissolved in acetonitrile (100 mL) and concentrated under reduced pressure. To the residue, methyl-tert-butyl ether (250 mL) was added and recrystallization was carried out by being left to stand at room temperature, and the crystal (21.8 g) was filtered (the crystal is the crystal mentioned in Example 23). The resultant crystal was dissolved by heating at 60° C. in a mixed solution of methyl-tert-butyl ether (833 mL) and acetonitrile (167 mL). The solution was recrystallized by being left to stand at room temperature, and the crystal (7.39 g) was filtered. The resultant crystal was diluted with a mixed solution of an aqueous saturated sodium hydrogen carbonate solution and saturated brine, and then extracted five times with ethyl acetate. The organic layer was washed with a mixed solution of an aqueous saturated sodium hydrogen carbonate solution and saturated brine. The organic layer was dried over anhydrous sodium sulfate and concentrated under reduced pressure to obtain the title compound having the following physical properties (4.11 g, 88% ee). Optical purity was confirmed using a high-performance liquid chromatography (HPLC).

Column: CHIRALPAK AD-H (0.46 cmϕ×25 cm L, manufactured by Daicel Chemical Industries Limited.);
Eluent: n-hexane:ethanol:diethylamine=80:20:0.1;
Flow rate: 1 mL/minute;
Detection wavelength: 210 nm.
HPLC retention time: 11.9 minutes;
Specific rotation: $[\alpha]_D^{25}$=−15.2 (c=1.03, chloroform).

Example 25

2,2'-[[(4-formylbenzyl)imino]bis(methylene)]bis(N,N-dimethyl-1H-imidazole-1-sulfonamide)

2,2'-[{[4-(diethoxymethyl)benzyl]imino}bis(methylene)] bis(N,N-dimethyl-1H-imidazole-1-sulfonamide) (International Publication WO 2007/058322 pamphlet, Example 27; 10.0 g), ethyl acetate (100 mL) and 2N hydrochloric acid (100 mL) were added, followed by stirring at room temperature for 3 minutes. The aqueous layer was neutralized with an aqueous saturated sodium carbonate solution, extracted with ethyl acetate and then washed with saturated brine. The organic layer was dried over anhydrous magnesium sulfate and then concentrated under reduced pressure to obtain the title compound (7.46 g) having the following physical properties.

TLC: Rf 0.42 (chloroform:methanol: 28% ammonia water=100:10:2);

NMR (CDCl$_3$): δ 2.81 (s, 12H), 4.18 (s, 2H), 4.22 (s, 4H), 7.00 (d, J=1.5 Hz, 2H), 7.24 (d, J=1.5 Hz, 2H), 7.54 (d, J=8.2 Hz, 2H), 7.80 (d, J=8.2 Hz, 2H), 9.97 (s, 1H).

Example 26

2,2'-[{[4-(hydroxymethyl)benzyl]imino}bis(methylene)]bis(N,N-dimethyl-1H-imidazole-1-sulfonamide)

Under an argon atmosphere, the compound (20.0 g) obtained in Example 25 was dissolved by adding anhydrous methanol (80 mL) and tetrahydrofuran (70 mL) and sodium borohydride (1.04 g) was added, followed by stirring for 2 hours. After water was added to the reaction solution, the solvent was concentrated under reduced pressure. The aqueous layer was extracted with ethyl acetate and then washed with saturated brine. The organic layer was dried over anhydrous magnesium sulfate and then concentrated under reduced pressure to obtain the title compound (19.4 g) having the following physical properties.
TLC: Rf 0.26 (chloroform:methanol: 28% ammonia water=100:10:2);
NMR (CDCl$_3$): δ 2.23 (s, 1H), 2.80 (s, 12H), 4.08 (s, 2H), 4.18 (s, 4H), 4.64 (s, 2H), 6.98 (d, J=1.7 Hz, 2H), 7.23 (d, J=1.7 Hz, 2H), 7.24-7.39 (m, 4H).

Example 27

2,2'-[{[4-(chloromethyl)benzyl]imino}bis(methylene)]bis(N,N-dimethyl-1H-imidazole-1-sulfonamide)

To a tetrahydrofuran (12 mL) solution of the compound (1.25 g) obtained in Example 26, diisopropylethylamine (0.64 mL) was added, and methanesulfonyl chloride (0.23 mL) and lithium chloride (207 mg) were added at 0° C. The reaction solution was stirred for 1 hour while raising the temperature to room temperature. To the reaction solution, an aqueous saturated sodium hydrogen carbonate solution was added and then the solution was extracted twice with ethyl acetate. The organic layers were combined, washed with saturated brine, dried over anhydrous sodium sulfate and then concentrated under reduced pressure to obtain the title compound (1.63 g) having the following physical properties.
TLC: Rf 0.51 (dichloromethane:methanol=9:1);
NMR (CDCl$_3$): δ 2.78 (s, 12H), 4.10 (s, 2H), 4.20 (s, 4H), 4.55 (s, 2H), 6.98 (s, 2H), 7.19-7.39 (m, 6H).

Example 28

8-tert-butyl 3-ethyl (3R)-2-(4-{[bis({1-[(dimethylamino)sulfonyl]-1H-imidazol-2-yl}methyl)amino]methyl}benzyl)-2,8-diazaspiro[4.5]decane-3,8-dicarboxylate Under an argon atmosphere, the compound (1.63 g) obtained in Example 27 and the compound (762 mg) obtained in Example 23 were dissolved in anhydrous acetonitrile (15 mL) and diisopropylethylamine (2.12 mL), followed by stirring at 50° C. for 15 hours. To the reaction solution, water was added and the solution was extracted with ethyl acetate. The organic layer was washed with saturated brine, dried over anhydrous sodium sulfate and then concentrated under reduced pressure. The residue was purified by silica gel chromatography (CHROMATOREX NH (trade name), manufactured by FUJI SILYSIA CHEMICAL LTD.) (n-hexane:ethyl acetate=1:1→1:2→0:1) to obtain the title compound (1.92 g) having the following physical properties.
TLC: Rf 0.62 (dichloromethane:methanol:28% ammonia water=90:10:1);
NMR (CDCl$_3$): δ 1.26 (t, J=7.1 Hz, 3H), 1.43 (s, 9H), 1.54-1.67 (m, 4H), 1.79-1.88 (m, 1H), 1.90-2.00 (m, 1H), 2.19 (d, J=9.0 Hz, 1H), 2.80 (s, 12H), 2.86 (d, J=9.0 Hz, 1H), 3.23-3.39 (m, 5H), 3.44 (d, J=13.0 Hz, 1H), 3.92 (d, J=13.0 Hz, 1H), 4.02-4.27 (m, 8H), 6.98 (s, 2H), 7.17-7.33 (m, 6H).

Example 29

Ethyl (3R)-2-(4-{[bis(1H-imidazol-2-ylmethyl)amino]methyl}benzyl)-2,8-diazaspiro[4.5]decane-3-carboxylate The same procedure as in Example 2 was carried out, except that the compound obtained in Example 28 was used in place of the compound obtained in Example 1 in Example 2, the title compound having the following physical properties was obtained.
TLC: Rf 0.35 (dichloromethane:methanol:28% ammonia water=80:20:2);
NMR (CDCl$_3$): δ 1.25 (t, J=7.1 Hz, 3H), 1.50-1.62 (m, 2H), 1.65-1.76 (m, 2H), 1.78-1.91 (m, 1H), 1.93-2.05 (m, 1H), 2.18-2.26 (m, 1H), 2.70-2.98 (m, 5H), 3.35 (t, J=7.8 Hz, 1H), 3.43-3.52 (m, 1H), 3.53-3.66 (m, 6H), 3.88 (d, J=13.2 Hz, 1H), 4.10 (q, J=7.1 Hz, 2H), 7.00 (s, 4H), 7.21-7.31 (m, 4H).

Example 30

Ethyl (3R)-2-(4-{[bis(1H-imidazol-2-ylmethyl)amino]methyl}benzyl)-8-isobutyl-2,8-diazaspiro[4.5]decane-3-carboxylate The same procedure as in Example 3 was carried out, except that the compound obtained in Example 29 was used in place of the compound obtained in Example 2 in Example 3, the title compound having the following physical properties was obtained.
TLC: Rf 0.30 (dichloromethane:methanol:28% ammonia water=90:10:1);
NMR (CDCl$_3$): δ 0.85 (d, J=6.6 Hz, 6H), 1.24 (t, J=7.2 Hz, 3H), 1.45-1.60 (m, 2H), 1.62-1.83 (m, 4H), 1.94 (dd, J=12.9, 9.0 Hz, 1H), 2.00 (d, J=7.2 Hz, 2H), 2.10-2.35 (m, 5H), 2.94 (d, J=9.0 Hz, 1H), 3.30 (t, J=8.1 Hz, 1H), 3.53 (d, J=12.9 Hz, 1H), 3.60 (s, 4H), 3.64 (s, 2H), 3.83 (d, J=12.9 Hz, 1H), 4.06 (q, J=7.2 Hz, 2H), 7.05 (s, 4H), 7.22-7.30 (m, 4H);
Specific rotation: $[\alpha]_D^{25}$=+44.5 (c=1.04, chloroform).

Example 30(1) to 30(5)

The same procedure as in Example 28→Example 29→Example 30 was carried out, except that the compound obtained in Example 23 or the compound obtained in Example 24 was used in place of the compound obtained in Example 23 in Example 28, and that isobutylaldehyde or corresponding compound was used in place of isobutylaldehyde in Example 30, the following title compound was obtained.

Example 30(1)

Ethyl (3S)-2-(4-{[bis(1H-imidazol-2-ylmethyl)amino]methyl}benzyl)-8-isobutyl-2,8-diazaspiro[4.5]decane-3-carboxylate TLC: Rf 0.30 (dichloromethane:methanol:28% ammonia water=90:10:1);

NMR (CDCl₃): δ 0.85 (d, J=6.6 Hz, 6H), 1.24 (t, J=7.2 Hz, 3H), 1.45-1.60 (m, 2H), 1.62-1.83 (m, 4H), 1.94 (dd, J=12.9, 9.0 Hz, 1H), 2.00 (d, J=7.2 Hz, 2H), 2.10-2.35 (m, 5H), 2.94 (d, J=9.0 Hz, 1H), 3.30 (t, J=8.1 Hz, 1H), 3.53 (d, J=12.9 Hz, 1H), 3.60 (s, 4H), 3.64 (s, 2H), 3.83 (d, J=12.9 Hz, 1H), 4.06 (q, J=7.2 Hz, 2H), 7.05 (s, 4H), 7.22-7.30 (m, 4H);

Specific rotation: $[\alpha]_D^{25}$=−41.7 (c=1.05, chloroform).

Example 30(2)

Ethyl (3R)-2-(4-{[bis(1H-imidazol-2-ylmethyl)amino]methyl}benzyl)-8-cyclohexyl-2,8-diazaspiro[4.5]decane-3-carboxylate TLC: Rf 0.23 (dichloromethane:methanol:28% ammonia water=90:10:1);

NMR (CDCl₃): δ 1.09-1.29 (m, 6H), 1.23 (t, J=7.1 Hz, 3H), 1.46-1.87 (m, 9H), 1.94 (dd, J=12.8, 8.0 Hz, 1H), 2.14-2.28 (m, 1H), 2.23 (d, J=9.3 Hz, 1H), 2.35-2.55 (m, 4H), 2.94 (d, J=9.3 Hz, 1H), 3.31 (t, J=8.0 Hz, 1H), 3.55 (d, J=13.0 Hz, 1H), 3.61 (s, 4H), 3.65 (s, 2H), 3.83 (d, J=13.0 Hz, 1H), 4.06 (q, J=7.1 Hz, 2H), 7.05 (s, 4H), 7.23-7.33 (m, 4H);

Specific rotation: $[\alpha]_D^{25}$=+45.7 (c=0.27, chloroform).

Example 30(3)

Ethyl (3S)-2-(4-{[bis(1H-imidazol-2-ylmethyl)amino]methyl}benzyl)-8-cyclohexyl-2,8-diazaspiro[4.5]decane-3-carboxylate TLC: Rf 0.23 (dichloromethane:methanol:28% ammonia water=90:10:1);

NMR (CDCl₃): δ 0.94-1.31 (m, 6H), 1.23 (t, J=7.1 Hz, 3H), 1.41-1.99 (m, 10H), 2.14-2.28 (m, 1H), 2.23 (d, J=9.2 Hz, 1H), 2.31-2.57 (m, 4H), 2.95 (d, J=9.2 Hz, 1H), 3.31 (t, J=8.1 Hz, 1H), 3.56 (d, J=13.2 Hz, 1H), 3.61 (s, 4H), 3.66 (s, 2H), 3.83 (d, J=13.2 Hz, 1H), 4.06 (q, J=7.1 Hz, 2H), 7.06 (s, 4H), 7.22-7.35 (m, 4H);

Specific rotation: $[\alpha]_D^{25}$=−42.9 (c=0.20, chloroform).

Example 30(4)

Ethyl (3R)-2-(4-{[bis(1H-imidazol-2-ylmethyl)amino]methyl}benzyl)-8-(2,2-dimethylpropyl)-2,8-diazaspiro[4.5]decane-3-carboxylate TLC: Rf 0.29 (dichloromethane:methanol:28% ammonia water=90:10:1);

NMR (CDCl₃): δ 0.82 (s, 9H), 1.24 (t, J=7.2 Hz, 3H), 1.42-1.52 (m, 2H), 1.58-1.66 (m, 2H), 1.77 (dd, J=12.9, 8.4 Hz, 1H), 1.94 (dd, J=12.9, 8.4 Hz, 1H), 1.97 (s, 2H), 2.20 (d, J=9.0 Hz, 1H), 2.30-2.46 (m, 4H), 2.94 (d, J=9.0 Hz, 1H), 3.30 (t, J=8.4 Hz, 1H), 3.52 (d, J=12.9 Hz, 1H), 3.61 (s, 4H), 3.63 (s, 2H), 3.83 (d, J=12.9 Hz, 1H), 4.07 (q, J=7.2 Hz, 2H), 7.05 (s, 4H), 7.23-7.30 (m, 4H);

Specific rotation: $[\alpha]_D^{25}$=+43.0 (c=1.05, chloroform).

Example 30(5)

Ethyl (3S)-2-(4-{[bis(1H-imidazol-2-ylmethyl)amino]methyl}benzyl)-8-(2,2-dimethylpropyl)-2,8-diazaspiro[4.5]decane-3-carboxylate TLC: Rf 0.29 (dichloromethane:methanol:28% ammonia water=90:10:1);

NMR (CDCl₃): δ 0.82 (s, 9H), 1.24 (t, J=7.2 Hz, 3H), 1.42-1.52 (m, 2H), 1.58-1.66 (m, 2H), 1.77 (dd, J=12.9, 8.4 Hz, 1H), 1.94 (dd, J=12.9, 8.4 Hz, 1H), 1.97 (s, 2H), 2.20 (d, J=9.0 Hz, 1H), 2.30-2.46 (m, 4H), 2.94 (d, J=9.0 Hz, 1H), 3.30 (t, J=8.4 Hz, 1H), 3.52 (d, J=12.9 Hz, 1H), 3.61 (s, 4H), 3.63 (s, 2H), 3.83 (d, J=12.9 Hz, 1H), 4.07 (q, J=7.2 Hz, 2H), 7.05 (s, 4H), 7.23-7.30 (m, 4H);

Specific rotation: $[\alpha]_D^{25}$=−41.5 (c=1.01, chloroform).

Example 31

Ethyl (3R)-2-(4-{[bis(1H-imidazol-2-ylmethyl)amino]methyl}benzyl)-8-(1-ethylpropyl)-2,8-diazaspiro[4.5]decane-3-carboxylate The same procedure as in Example 4 was carried out, except that the compound obtained in Example 29 was used in place of the compound obtained in Example 2 in Example 4, the title compound having the following physical properties was obtained.

TLC: Rf 0.32 (dichloromethane:methanol:28% ammonia water=90:10:1);

NMR (CDCl₃): δ 0.86 (t, J=7.2 Hz, 6H), 1.16-1.34 (m, 5H), 1.35-1.55 (m, 4H), 1.58-1.66 (m, 2H), 1.75 (dd, J=13.2, 8.4 Hz, 1H), 1.93 (dd, J=13.2, 8.4 Hz, 1H), 2.08 (m, 1H), 2.21 (d, J=9.3 Hz, 1H), 2.30-2.46 (m, 4H), 2.94 (d, J=9.3 Hz, 1H), 3.30 (t, J=8.4 Hz, 1H), 3.53 (d, J=13.2 Hz, 1H), 3.60 (s, 4H), 3.63 (s, 2H), 3.83 (d, J=13.2 Hz, 1H), 4.06 (q, J=6.9 Hz, 2H), 7.04 (s, 4H), 7.22-7.30 (m, 4H);

Specific rotation: $[\alpha]_D^{25}$=+42.9 (c=1.01, chloroform).

Example 31(1)

The same procedure as in Example 28→Example 29→Example 31 was carried out, except that the compound obtained in Example 24 was used in place of the compound obtained in Example 23 in Example 28, the title compound having the following physical properties was obtained.

Example 31(1)

Ethyl (3S)-2-(4-{[bis(1H-imidazol-2-ylmethyl)amino]methyl}benzyl)-8-(1-ethylpropyl)-2,8-diazaspiro[4.5]decane-3-carboxylate TLC: Rf 0.32 (dichloromethane:methanol:28% ammonia water=90:10:1);

NMR (CDCl₃): δ 0.86 (t, J=7.2 Hz, 6H), 1.16-1.34 (m, 5H), 1.35-1.55 (m, 4H), 1.58-1.66 (m, 2H), 1.75 (dd, J=13.2, 8.4 Hz, 1H), 1.93 (dd, J=13.2, 8.4 Hz, 1H), 2.08 (m, 1H), 2.21 (d, J=9.3 Hz, 1H), 2.30-2.46 (m, 4H), 2.94 (d, J=9.3 Hz, 1H), 3.30 (t, J=8.4 Hz, 1H), 3.53 (d, J=13.2 Hz, 1H), 3.60 (s, 4H), 3.63 (s, 2H), 3.83 (d, J=13.2 Hz, 1H), 4.06 (q, J=6.9 Hz, 2H), 7.04 (s, 4H), 7.22-7.30 (m, 4H);

Specific rotation: $[\alpha]_D^{25}$=−41.6 (c=1.06, chloroform).

Example 32

(3R)-2-(4-{[bis(1H-imidazol-2-ylmethyl)amino]methyl}benzyl)-8-isobutyl-2,8-diazaspiro[4.5]decane-3-carboxylic acid The compound (180 mg) obtained in Example 30 was dissolved in 5N hydrochloric acid (1.5 mL), followed by stirring at 95° C. for 30 minutes. The reaction solution was concentrated under reduced pressure, together with toluene. The residue was purified by silica gel chromatography (CHROMATOREX NH (trade name), manufactured by Fuji Silysia Chemical Ltd.) (dichloromethane:methanol=9:1→5:1) to obtain the title compound (101 mg) having the following physical properties.

TLC: Rf 0.29 (dichloromethane:methanol:28% ammonia water=50:10:1);

NMR (CD$_3$OD): δ 0.91 (d, J=6.6 Hz, 6H), 1.58-1.80 (m, 4H), 1.80-2.00 (m, 2H), 2.16-2.35 (m, 2H), 2.40-2.65 (m, 4H), 2.79 (m, 1H), 3.23 (m, 1H), 3.52 (s, 2H), 3.64 (s, 4H), 3.70 (m, 1H), 4.00 (m, 1H), 4.28 (d, J=12.9 Hz, 1H), 6.99 (s, 4H), 7.36 (d, J=8.1 Hz, 2H), 7.41 (d, J=8.1 Hz, 2H);

Specific rotation: $[\alpha]_D^{25}$=+31.7 (c=1.02, methanol).

Examples 32(1) to 32(7)

The same procedure as in Example 32 was carried out, except that Examples 30(1) to (5), Example 31 or Example 31(1) were used in place of the compound obtained in Example 30 in Example 32, the following title compound was obtained.

Example 32(1)

(3S)-2-(4-{[bis(1H-imidazol-2-ylmethyl)amino]methyl}benzyl)-8-isobutyl-2,8-diazaspiro[4.5]decane-3-carboxylic acid TLC: Rf 0.29 (dichloromethane:methanol:28% ammonia water=50:10:1);

NMR (CD$_3$OD): δ 0.91 (d, J=6.6 Hz, 6H), 1.58-1.80 (m, 4H), 1.80-2.00 (m, 2H), 2.16-2.35 (m, 2H), 2.40-2.65 (m, 4H), 2.79 (m, 1H), 3.23 (m, 1H), 3.52 (s, 2H), 3.64 (s, 4H), 3.70 (m, 1H), 4.00 (m, 1H), 4.28 (d, J=12.9 Hz, 1H), 6.99 (s, 4H), 7.36 (d, J=8.1 Hz, 2H), 7.41 (d, J=8.1 Hz, 2H);

Specific rotation: $[\alpha]_D^{25}$=−30.4 (c=1.02, methanol).

Example 32(2)

(3R)-2-(4-{[bis(1H-imidazol-2-ylmethyl)amino]methyl}benzyl)-8-cyclohexyl-2,8-diazaspiro[4.5]decane-3-carboxylic acid TLC: Rf 0.36 (dichloromethane:methanol:28% ammonia water=80:20:2);

NMR (DMSO-d$_6$): δ 0.89-1.84 (m, 16H), 1.93 (d, J=9.3 Hz, 1H), 2.07-2.21 (m, 1H), 2.21-2.45 (m, 4H), 2.72 (d, J=9.3 Hz, 1H), 3.00 (t, J=8.0 Hz, 1H), 3.20-3.56 (m, 7H), 4.12 (d, J=13.9 Hz, 1H), 6.92 (s, 4H), 7.15 (d, J=8.1 Hz, 2H), 7.27 (d, J=8.1 Hz, 2H);

Specific rotation: $[\alpha]_D^{25}$=+48.4 (c=0.44, methanol).

Example 32(3)

(3S)-2-(4-{[bis(1H-imidazol-2-ylmethyl)amino]methyl}benzyl)-8-cyclohexyl-2,8-diazaspiro[4.5]decane-3-carboxylic acid TLC: Rf 0.36 (dichloromethane:methanol:28% ammonia water=80:20:2);

NMR (DMSO-d$_6$): δ 0.96-1.24 (m, 6H), 1.31-1.84 (m, 10H), 2.04 (d, J=9.2 Hz, 1H), 2.09-2.23 (m, 1H), 2.23-2.42 (m, 4H), 2.78 (d, J=9.2 Hz, 1H), 3.05-3.49 (m, 4H), 3.52 (s, 4H), 4.08 (d, J=13.5 Hz, 1H), 6.94 (s, 4H), 7.20 (d, J=8.1 Hz, 2H), 7.29 (d, J=8.1 Hz, 2H);

Specific rotation: $[\alpha]_D^{25}$=−42.8 (c=0.31, methanol).

Example 32(4)

(3R)-2-(4-{[bis(1H-imidazol-2-ylmethyl)amino]methyl}benzyl)-8-(2,2-dimethylpropyl)-2,8-diazaspiro[4.5]decane-3-carboxylic acid TLC: Rf 0.31 (dichloromethane:methanol:28% ammonia water=50:10:1);

NMR (CD$_3$OD): δ 0.86 (s, 9H), 1.55-1.74 (m, 4H), 1.97 (dd, J=12.9, 8.7 Hz, 1H), 2.10 (s, 2H), 2.26 (dd, J=12.9, 8.7 Hz, 1H), 2.42-2.60 (m, 4H), 2.95 (m, 1H), 3.35 (m, 1H), 3.53 (s, 2H), 3.67 (s, 4H), 3.85 (m, 1H), 4.18 (m, 1H), 4.34 (d, J=12.9 Hz, 1H), 7.00 (s, 4H), 7.40 (d, J=8.1 Hz, 2H), 7.44 (d, J=8.1 Hz, 2H);

Specific rotation: $[\alpha]_D^{25}$=+24.1 (c=1.01, methanol).

Example 32(5)

(3S)-2-(4-{[bis(1H-imidazol-2-ylmethyl)amino]methyl}benzyl)-8-(2,2-dimethylpropyl)-2,8-diazaspiro[4.5]decane-3-carboxylic acid TLC: Rf 0.31 (dichloromethane:methanol:28% ammonia water=50:10:1);

NMR (CD$_3$OD): δ 0.86 (s, 9H), 1.55-1.74 (m, 4H), 1.97 (dd, J=12.9, 8.7 Hz, 1H), 2.10 (s, 2H), 2.26 (dd, J=12.9, 8.7 Hz, 1H), 2.42-2.60 (m, 4H), 2.95 (m, 1H), 3.35 (m, 1H), 3.53 (s, 2H), 3.67 (s, 4H), 3.85 (m, 1H), 4.18 (m, 1H), 4.34 (d, J=12.9 Hz, 1H), 7.00 (s, 4H), 7.40 (d, J=8.1 Hz, 2H), 7.44 (d, J=8.1 Hz, 2H);

Specific rotation: $[\alpha]_D^{25}$=−25.1 (c=1.04, methanol).

Example 32(6)

(3R)-2-(4-{[bis(1H-imidazol-2-ylmethyl)amino]methyl}benzyl)-8-(1-ethylpropyl)-2,8-diazaspiro[4.5]decane-3-carboxylic acid TLC: Rf 0.24 (dichloromethane:methanol:28% ammonia water=50:10:1);

NMR (CD$_3$OD): δ 0.94 (t, J=7.2 Hz, 6H), 1.35-1.82 (m, 8H), 1.91 (dd, J=12.6, 8.4 Hz, 1H), 2.19 (dd, J=12.6, 8.4 Hz, 1H), 2.42 (m, 1H), 2.60-2.82 (m, 5H), 3.20 (m, 1H), 3.52 (s, 2H), 3.58-3.72 (m, 5H), 3.95 (m, 1H), 4.25 (d, J=12.6 Hz, 1H), 6.99 (s, 4H), 7.35 (d, J=8.1 Hz, 2H), 7.40 (d, J=8.1 Hz, 2H);

Specific rotation: $[\alpha]_D^{25}$=+31.9 (c=1.02, methanol).

Example 32(7)

(3S)-2-(4-{[bis(1H-imidazol-2-ylmethyl)amino]methyl}benzyl)-8-(1-ethylpropyl)-2,8-diazaspiro[4.5]decane-3-carboxylic acid TLC: Rf 0.24 (dichloromethane:methanol:28% ammonia water=50:10:1);

NMR (CD$_3$OD): δ 0.94 (t, J=7.2 Hz, 6H), 1.35-1.82 (m, 8H), 1.91 (dd, J=12.6, 8.4 Hz, 1H), 2.19 (dd, J=12.6, 8.4 Hz, 1H), 2.42 (m, 1H), 2.60-2.82 (m, 5H), 3.20 (m, 1H), 3.52 (s, 2H), 3.58-3.72 (m, 5H), 3.95 (m, 1H), 4.25 (d, J=12.6 Hz, 1H), 6.99 (s, 4H), 7.35 (d, J=8.1 Hz, 2H), 7.40 (d, J=8.1 Hz, 2H);

Specific rotation: $[\alpha]_D^{25}$=−30.7 (c=1.07, methanol).

Example 32(8)

Calcium bis[(3S)-2-(4-{[bis(1H-imidazol-2-ylmethyl)amino]methyl}benzyl)-8-(1-ethylpropyl)-2,8-diazaspiro[4.5]decane-3-carboxylic acid]

The compound (16.5 g) obtained in Example 31(1) was dissolved in 52 mL of ethanol and an aqueous 2N sodium hydroxide solution (10 mL) was added thereto, followed by stirring at 70° C. for 2 hours. After completion of the reaction, the reaction solution was neutralized by adding an aqueous 5N hydrochloric acid solution (5.2 mL). To a separately prepared water 130 mL solution of calcium chloride (1.45 g), the neutralized solution was slowly added at 0° C., and the precipitated solid was filtered and washed with ethanol and water to obtain the title compound (14.2 g) having the following physical properties.

TLC: Rf 0.24 (dichloromethane:methanol:28% ammonia water=80:20:4);

Mass (FAB, Pos.): 1105 (M+H)+, 572 (1/2M+1/2Ca)+, 534 (1/2M−1/2Ca+2H)+;

NMR (CD$_3$OD): δ 0.84 (t, J=7.5 Hz, 6H), 1.14-1.75 (m, 9H), 1.88-2.45 (m, 7H), 2.78 (d, J=10.5 Hz, 1H), 3.07 (m, 1H), 3.30 (m, 1H), 3.49 (s, 2H), 3.62 (s, 4H), 4.05 (d, J=12.3 Hz, 1H), 6.99 (s, 4H), 7.30 (s, 4H).

Example 32(9)

Calcium bis[(3R)-2-(4-{[bis(1H-imidazol-2-ylmethyl)amino]methyl}benzyl)-8-(1-ethylpropyl)-2,8-diazaspiro[4.5]decane-3-carboxylic acid]

The same procedure as in Example 32(8) was carried out using the compound obtained in Example 31, the title compound was obtained.

Example 33

8-tert-butyl 3-ethyl (3R)-2-[4-({({1-[(dimethylamino)sulfonyl]-1H-imidazol-2-yl}methyl)[(1-methyl-1H-imidazol-2-yl)methyl]amino}methyl)benzyl]-2,8-diazaspiro[4.5]decane-3,8-dicarboxylate Under an argon atmosphere, diisopropylethylamine (0.24 mL) was added to an acetonitrile (1.5 mL) solution of the compound (290 mg) obtained in Example 7, and methanesulfonyl chloride (69.8 μL) was added at 0° C. After stirring the reaction solution for 15 minutes, diisopropylethylamine (0.24 mL) and an acetonitrile (1.5 mL) solution of the compound (217 mg) obtained in Example 23 were added at 0° C. After stirring the reaction solution at 50° C. for 12 hours, an aqueous saturated sodium hydrogen carbonate solution was added to the reaction solution and the solution was extracted with ethyl acetate. The organic layer was washed with saturated brine and then dried over anhydrous magnesium sulfate, and concentrated under reduced pressure. The residue was purified by silica gel chromatography (n-hexane:ethyl acetate=50:50→0:100→ethyl acetate:methanol:10% ammonia water=90:10→0:100) to obtain the title compound (389 mg) having the following physical properties.

TLC: Rf 0.48 (dichloromethane:methanol:28% ammonia water=90:10:1);

NMR (CDCl$_3$): δ 1.26 (t, J=6.7 Hz, 3H), 1.42-1.44 (m, 1H), 1.55-1.65 (m, 2H), 1.78-2.01 (m, 2H), 2.20 (d, J=9.1 Hz, 1H), 2.74 (s, 6H), 2.86 (d, J=9.1 Hz, 1H), 3.24-3.39 (m, 5H), 3.45 (d, J=13.1 Hz, 1H), 3.53 (s, 3H), 3.78 (s, 2H), 3.83 (s, 2H), 3.89-3.98 (m, 3H), 4.14 (q, J=6.7 Hz, 2H), 6.79 (d, J=1.2 Hz, 1H), 6.87 (d, J=1.2 Hz, 1H), 7.01 (d, J=1.7 Hz, 1H), 7.20-7.31 (m, 5H).

Example 34

Ethyl (3R)-2-[4-({(1H-imidazol-2-ylmethyl)[(1-methyl-1H-imidazol-2-yl)methyl]amino}methyl)benzyl]-2,8-diazaspiro[4.5]decane-3-carboxylate The same procedure as in Example 2 was carried out, except that the compound obtained in Example 33 was used in place of the compound obtained in Example 1 in Example 2, the title compound having the following physical properties was obtained.

TLC: Rf 0.43 (dichloromethane:methanol:28% ammonia water=80:20:1);

NMR (CDCl$_3$): δ 1.25 (t, J=6.9 Hz, 3H), 1.44-1.54 (m, 2H), 1.61-1.69 (m, 2H), 1.84 (dd, J=12.9, 7.5 Hz, 1H), 1.97 (dd, J=12.9, 8.5 Hz, 1H), 2.21 (d, J=9.1 Hz, 1H), 2.68-2.85 (m, 4H), 2.92 (d, J=9.1 Hz, 1H), 3.35 (dd, J=8.5, 7.5 Hz, 1H), 3.43-3.52 (m, 3H), 3.55 (s, 3H), 3.62 (s, 2H), 3.67 (s, 2H), 3.94 (d, J=13.1 Hz, 1H), 4.08-4.18 (m, 2H), 6.87 (d, J=1.3 Hz, 1H), 6.99 (d, J=1.3 Hz, 1H), 7.09 (s, 2H), 7.25-7.38 (m, 4H).

Example 35

Ethyl (3R)-2-[4-({(1H-imidazol-2-ylmethyl)[(1-methyl-1H-imidazol-2-yl)methyl]amino}methyl)benzyl]-8-isobutyl-2,8-diazaspiro[4.5]decane-3-carboxylate The same procedure as in Example 3 was carried out, except that the compound obtained in Example 34 was used in place of the compound obtained in Example 2, the title compound having the following physical properties was obtained.

TLC: Rf 0.61 (dichloromethane:methanol:28% ammonia water=90:10:1);

NMR (CDCl$_3$): δ 0.85 (d, J=6.5 Hz, 6H), 1.25 (t, J=7.1 Hz, 3H), 1.46-1.55 (m, 2H), 1.62-1.68 (m, 2H), 1.68-1.85 (m, 2H), 1.94 (dd, J=12.8, 8.6 Hz, 1H), 2.00 (d, J=7.4 Hz, 2H), 2.14-2.39 (m, 5H), 2.89 (d, J=9.1 Hz, 1H), 3.32 (t, J=8.1 Hz, 1H), 3.42-3.50 (m, 3H), 3.54 (s, 3H), 3.62 (s, 2H), 3.67 (s, 2H), 3.92 (d, J=13.1 Hz, 1H), 4.07-4.17 (m, 2H), 6.86 (d, J=1.3 Hz, 1H), 6.99 (d, J=1.3 Hz, 1H), 7.05-7.14 (m, 2H), 7.28 (d, J=8.2 Hz, 2H), 7.33 (d, J=8.2 Hz, 2H), 12.31 (s, 1H);

Specific rotation: $[\alpha]_D^{25}$=+36.0 (c=0.39, chloroform).

Examples 35(1) to 35(5)

The same procedure as in Example 33→Example 34→Example 35 was carried out, except that the compound obtained in Example 23 or the compound obtained in Example 24 was used in place of the compound obtained in Example 23 in Example 33, and that isobutylaldehyde or corresponding compound was used in place of isobutylaldehyde in Example 35, the following title compound was obtained.

Example 35(1)

Ethyl (3S)-2-[4-({(1H-imidazol-2-ylmethyl)[(1-methyl-1H-imidazol-2-yl)methyl]amino}methyl)benzyl]-8-isobutyl-2,8-diazaspiro[4.5]decane-3-carboxylate TLC: Rf 0.61 (dichloromethane:methanol:28% ammonia water=90:10:1);

NMR (CDCl$_3$): δ 0.85 (d, J=6.5 Hz, 6H), 1.25 (t, J=7.1 Hz, 3H), 1.46-1.55 (m, 2H), 1.60-1.76 (m, 3H), 1.80 (dd, J=12.8, 7.7 Hz, 1H), 1.94 (dd, J=12.8, 8.4 Hz, 1H), 2.00 (d, J=7.4 Hz, 2H), 2.13-2.36 (m, 5H), 2.89 (d, J=9.1 Hz, 1H), 3.32 (t, J=8.1 Hz, 1H), 3.43-3.51 (m, 3H), 3.54 (s, 3H), 3.62 (s, 2H), 3.67 (s, 2H), 3.92 (d, J=13.1 Hz, 1H), 4.07-4.16 (m, 2H), 6.86 (d, J=1.2 Hz, 1H), 6.99 (d, J=1.2 Hz, 1H), 7.05-7.14 (m, 2H), 7.28 (d, J=8.2 Hz, 2H), 7.33 (d, J=8.2 Hz, 2H), 12.31 (s, 1H);
Specific rotation: $[\alpha]_D^{25}$=−36.4 (c=0.36, chloroform).

Example 35(2)

Ethyl (3R)-8-(2,2-dimethylpropyl)-2-[4-({(1H-imidazol-2-ylmethyl)[(1-methyl-1H-imidazol-2-yl)methyl]amino}methyl)benzyl]-2,8-diazaspiro[4.5]decane-3-carboxylate TLC: Rf 0.48 (dichloromethane:methanol:28% ammonia water=90:10:1);
NMR (CDCl$_3$): δ 0.82 (s, 9H), 1.25 (t, J=7.1 Hz, 3H), 1.42-1.51 (m, 2H), 1.57-1.66 (m, 2H), 1.79 (dd, J=12.7, 8.1 Hz, 1H), 1.95 (dd, J=12.7, 8.1 Hz, 1H), 1.95 (s, 2H), 2.18 (d, J=9.3 Hz, 1H), 2.26-2.47 (m, 4H), 2.88 (d, J=9.3 Hz, 1H), 3.31 (t, J=8.1 Hz, 1H), 3.45 (s, 2H), 3.46 (d, J=13.2 Hz, 1H), 3.55 (s, 3H), 3.61 (s, 2H), 3.67 (s, 2H), 3.92 (d, J=13.2 Hz, 1H), 4.06-4.18 (m, 2H), 6.87 (d, J=1.3 Hz, 1H), 6.99 (d, J=1.3 Hz, 1H), 7.04-7.14 (m, 2H), 7.28 (d, J=8.2 Hz, 2H), 7.33 (d, J=8.2 Hz, 2H) 12.16-12.50 (m, 1H);
Specific rotation: $[\alpha]_D^{25}$=+45.3 (c=0.58, chloroform).

Example 35(3)

Ethyl (3S)-8-(2,2-dimethylpropyl)-2-[4-({(1H-imidazol-2-ylmethyl)[(1-methyl-1H-imidazol-2-yl)methyl]amino}methyl)benzyl]-2,8-diazaspiro[4.5]decane-3-carboxylate TLC: Rf 0.48 (dichloromethane:methanol:28% ammonia water=90:10:1);
NMR (CDCl$_3$): δ 0.82 (s, 9H), 1.25 (t, J=7.0 Hz, 3H), 1.42-1.51 (m, 2H), 1.57-1.65 (m, 2H), 1.79 (dd, J=12.7, 8.1 Hz, 1H), 1.95 (dd, J=12.7, 8.1 Hz, 1H), 1.95 (s, 2H), 2.17 (d, J=9.3 Hz, 1H), 2.26-2.47 (m, 4H), 2.88 (d, J=9.3 Hz, 1H), 3.31 (t, J=8.1 Hz, 1H), 3.45 (s, 2H), 3.46 (d, J=13.2 Hz, 1H), 3.55 (s, 3H), 3.61 (s, 2H), 3.67 (s, 2H), 3.92 (d, J=13.2 Hz, 1H), 4.07-4.16 (m, 2H), 6.86 (d, J=1.3 Hz, 1H), 6.99 (d, J=1.3 Hz, 1H), 7.04-7.15 (m, 2H), 7.28 (d, J=8.2 Hz, 2H), 7.33 (d, J=8.2 Hz, 2H) 12.17-12.47 (m, 1H);
Specific rotation: $[\alpha]_D^{25}$=−41.3 (c=0.64, chloroform).

Example 35(4)

Ethyl (3R)-8-cyclohexyl-2-[4-({(1H-imidazol-2-ylmethyl)[(1-methyl-1H-imidazol-2-yl)methyl]amino}methyl)benzyl]-2,8-diazaspiro[4.5]decane-3-carboxylate TLC: Rf 0.30 (dichloromethane:methanol:28% ammonia water=90:10:1);
NMR (CDCl$_3$): δ 1.00-1.31 (m, 7H), 1.45-1.86 (m, 1H), 1.94 (dd, J=12.8, 8.1 Hz, 1H), 2.13-2.28 (m, 2H), 2.32-2.57 (m, 4H), 2.89 (d, J=9.1 Hz, 1H), 3.32 (t, J=8.1 Hz, 1H), 3.43-3.52 (m, 3H), 3.55 (s, 3H), 3.62 (s, 2H), 3.68 (s, 2H), 3.92 (d, J=13.1 Hz, 1H), 4.07-4.17 (m, 2H), 6.87 (d, J=1.2 Hz, 1H), 7.00 (d, J=1.2 Hz, 1H), 7.08 (m, 1H), 7.12 (s, 1H), 7.29 (d, J=8.2 Hz, 2H), 7.35 (d, J=8.2 Hz, 2H), 12.33 (s, 1H);
Specific rotation: $[\alpha]_D^{25}$=+35.0 (c=0.55, chloroform).

Example 35(5)

Ethyl (3S)-8-cyclohexyl-2-[4-({(1H-imidazol-2-ylmethyl)[(1-methyl-1H-imidazol-2-yl)methyl]amino}methyl)benzyl]-2,8-diazaspiro[4.5]decane-3-carboxylate TLC: Rf 0.30 (dichloromethane:methanol:28% ammonia water=90:10:1);
NMR (CDCl$_3$): δ 1.05-1.32 (m, 7H), 1.46-1.86 (m, 11H), 1.94 (dd, J=12.8, 8.1 Hz, 1H), 2.13-2.27 (m, 2H), 2.31-2.55 (m, 4H), 2.89 (d, J=9.1 Hz, 1H), 3.32 (t, J=8.1 Hz, 1H), 3.43-3.52 (m, 3H), 3.55 (s, 3H), 3.62 (s, 2H), 3.68 (s, 2H), 3.92 (d, J=13.1 Hz, 1H), 4.07-4.18 (m, 2H), 6.87 (d, J=1.3 Hz, 1H), 7.00 (d, J=1.3 Hz, 1H), 7.06-7.10 (m, 1H), 7.11-7.14 (m, 1H), 7.29 (d, J=8.2 Hz, 2H), 7.35 (d, J=8.2 Hz, 2H), 12.34 (s, 1H);
Specific rotation: $[\alpha]_D^{25}$=−37.8 (c=0.37, chloroform).

Example 36

Ethyl (3R)-8-(1-ethylpropyl)-2-[4-({(1H-imidazol-2-ylmethyl)[(1-methyl-1H-imidazol-2-yl)methyl]amino}methyl)benzyl]-2,8-diazaspiro[4.5]decane-3-carboxylate The same procedure as in Example 4 was carried out, except that the compound obtained in Example 34 was used in place of the compound obtained in Example 2 in Example 4, the title compound having the following physical properties was obtained.
TLC: Rf 0.50 (dichloromethane:methanol:28% ammonia water=90:10:1);
NMR (CDCl$_3$): δ 0.85 (t, J=7.2 Hz, 6H), 1.18-1.32 (m, 5H), 1.35-1.52 (m, 4H), 1.58-1.65 (m, 2H), 1.78 (dd, J=12.9, 8.1 Hz, 1H), 1.95 (dd, J=12.9, 8.1 Hz, 1H), 2.07 (m, 1H), 2.18 (d, J=9.3 Hz, 1H), 2.29-2.45 (m, 4H), 2.88 (d, J=9.3 Hz, 1H), 3.31 (t, J=8.1 Hz, 1H), 3.45 (s, 2H), 3.47 (d, J=12.9 Hz, 1H), 3.55 (s, 3H), 3.61 (s, 2H), 3.67 (s, 2H), 3.90 (d, J=12.9 Hz, 1H), 4.12 (q, J=7.2 Hz, 2H), 6.86 (d, J=1.2 Hz, 1H), 6.98 (d, J=1.2 Hz, 1H), 7.05-7.12 (m, 2H), 7.28 (d, J=8.4 Hz, 2H), 7.33 (d, J=8.4 Hz, 1H), 12.31 (m, 11-1);
Specific rotation: $[\alpha]_D^{25}$=+44.1 (c=1.09, chloroform).

Example 36(1)

Ethyl (3S)-8-(1-ethylpropyl)-2-[4-({(1H-imidazol-2-ylmethyl)[(1-methyl-1H-imidazol-2-yl)methyl]amino}methyl)benzyl]-2,8-diazaspiro[4.5]decane-3-carboxylate The same procedure as in Example 33→Example 34→Example 36 was carried out, except that the compound obtained in Example 24 was used in place of the compound obtained in Example 23 in Example 33, the title compound having the following physical properties was obtained.
TLC: Rf 0.50 (dichloromethane:methanol:28% ammonia water=90:10:1);
NMR (CDCl$_3$): δ 0.85 (t, J=7.2 Hz, 6H), 1.18-1.32 (m, 5H), 1.35-1.52 (m, 4H), 1.58-1.65 (m, 2H), 1.78 (dd, J=12.9, 8.1 Hz, 1H), 1.95 (dd, J=12.9, 8.1 Hz, 1H), 2.07 (m, 1H), 2.18 (d, J=9.3 Hz, 1H), 2.29-2.45 (m, 4H), 2.88 (d, J=9.3 Hz, 1H), 3.31 (t, J=8.1 Hz, 1H), 3.45 (s, 2H), 3.47 (d, J=12.9 Hz, 1H), 3.55 (s, 3H), 3.61 (s, 2H), 3.67 (s, 2H), 3.90 (d, J=12.9 Hz, 1H), 4.12 (q, J=7.2 Hz, 2H), 6.86 (d, J=1.2 Hz, 1H), 6.98 (d, J=1.2 Hz, 1H), 7.05-7.12 (m, 2H), 7.28 (d, J=8.4 Hz, 2H), 7.33 (d, J=8.4 Hz, 1H), 12.31 (m, 1H);
Specific rotation: $[\alpha]_D^{25}$=−41.6 (c=1.08, chloroform).

Example 37

(3R)-2-[4-({(1H-imidazol-2-ylmethyl)[(1-methyl-1H-imidazol-2-yl)methyl]amino}methyl)benzyl]-8-isobutyl-2,8-diazaspiro[4.5]decane-3-carboxylic acid The same procedure as in Example 32 was carried out, except that the compound obtained in Example 35 was used in place of the compound obtained in Example 30, the title compound having the following physical properties was obtained.

TLC: Rf 0.28 (dichloromethane:methanol:28% ammonia water=80:20:1);
NMR (CD$_3$OD): δ 0.91 (d, J=6.5 Hz, 6H), 1.60-1.76 (m, 4H), 2.14-2.32 (m, 3H), 2.38-2.67 (m, 4H), 2.71-2.81 (m, 1H), 3.21-3.27 (m, 1H), 1.79-2.00 (m, 2H), 3.49 (s, 3H), 3.53 (s, 2H), 3.59-3.72 (m, 5H), 4.00 (d, J=12.6 Hz, 1H), 4.26 (d, J=12.6 Hz, 1H), 6.82 (d, J=1.2 Hz, 1H), 6.96 (d, J=1.2 Hz, 1H), 6.97-7.01 (m, 2H), 7.29 (d, J=8.2 Hz, 2H), 7.40 (d, J=8.2 Hz, 2H);
Specific rotation: $[\alpha]_D^{25}$=+34.7 (c=0.33, methanol).

Examples 37(1) to 37(7)

The same procedure as in Example 37 was carried out, except that corresponding compound was used in place of the compound obtained in Example 35 in Example 37, the following title compound was obtained.

Example 37(1)

(3S)-2-[4-({(1H-imidazol-2-ylmethyl)[(1-methyl-1H-imidazol-2-yl)methyl]amino}methyl)benzyl]-8-isobutyl-2,8-diazaspiro[4.5]decane-3-carboxylic acid TLC: Rf 0.28 (dichloromethane:methanol:28% ammonia water=80:20:1);
NMR (CD$_3$OD): δ 0.91 (d, J=6.5 Hz, 6H), 1.62-1.76 (m, 4H), 1.77-2.02 (m, 2H), 2.14-2.32 (m, 3H), 2.40-2.65 (m, 4H), 2.74 (d, J=11.6 Hz, 1H), 3.24 (d, J=11.6 Hz, 1H), 3.49 (s, 3H), 3.53 (s, 2H), 3.59-3.72 (m, 5H), 3.98 (d, J=12.6 Hz, 1H), 4.25 (d, J=12.6 Hz, 1H), 6.82 (d, J=1.2 Hz, 1H), 6.96 (d, J=1.2 Hz, 1H), 6.97-7.01 (m, 2H), 7.29 (d, J=8.1 Hz, 2H), 7.39 (d, J=8.1 Hz, 2H);
Specific rotation: $[\alpha]_D^{25}$=−33.9 (c=0.31, methanol).

Example 37(2)

(3R)-8-(2,2-dimethylpropyl)-2-[4-({(1H-imidazol-2-ylmethyl)[(1-methyl-1H-imidazol-2-yl)methyl]amino}methyl)benzyl]-2,8-diazaspiro[4.5]decane-3-carboxylic acid TLC: Rf 0.32 (dichloromethane:methanol:28% ammonia water=90:10:1);
NMR (CD$_3$OD): δ 0.86 (s, 9H), 1.56-1.72 (m, 4H), 1.93-2.05 (m, 1H), 2.04-2.18 (m, 2H), 2.18-2.33 (m, 1H), 2.38-2.64 (m, 4H), 2.82-3.03 (m, 1H), 3.22-3.41 (m, 1H), 3.49 (s, 3H), 3.54 (s, 2H), 3.65 (s, 2H), 3.66 (s, 2H), 3.74-3.91 (m, 1H), 4.07-4.26 (m, 1H), 4.25-4.35 (m, 1H), 6.82 (d, J=1.3 Hz, 1H), 6.96 (d, J=1.3 Hz, 1H), 6.99 (s, 2H), 7.31 (d, J=8.1 Hz, 2H), 7.42 (d, J=8.1 Hz, 2H);
Specific rotation: $[\alpha]_D^{25}$=+23.1 (c=0.53, methanol).

Example 37(3)

(3S)-8-(2,2-dimethylpropyl)-2-[4-({(1H-imidazol-2-ylmethyl)[(1-methyl-1H-imidazol-2-yl)methyl]amino}methyl)benzyl]-2,8-diazaspiro[4.5]decane-3-carboxylic acid TLC: Rf 0.32 (dichloromethane:methanol:28% ammonia water=90:10:1);
NMR (CD$_3$OD): δ 0.86 (s, 9I), 1.55-1.72 (m, 4H), 1.93-2.04 (m, 1H), 2.05-2.16 (m, 2H), 2.19-2.32 (m, 1H), 2.41-2.60 (m, 4H), 2.85-3.01 (m, 1H), 3.27-3.40 (m, 1H), 3.49 (s, 3H), 3.54 (s, 2H), 3.65 (s, 2H), 3.65-3.67 (m, 2H), 3.74-3.90 (m, 1H), 4.07-4.25 (m, 1H), 4.25-4.36 (m, 1H), 6.82 (d, J=1.3 Hz, 1H), 6.96 (d, J=1.3 Hz, 1H), 6.99 (s, 2H), 7.31 (d, J=8.1 Hz, 2H), 7.42 (d, J=8.1 Hz, 2H);
Specific rotation: $[\alpha]_D^{25}$=−20.0 (c=0.59, methanol).

Example 37(4)

(3R)-8-cyclohexyl-2-[4-({(1H-imidazol-2-ylmethyl)[(1-methyl-1H-imidazol-2-yl)methyl]amino}methyl)benzyl]-2,8-diazaspiro[4.5]decane-3-carboxylic acid TLC: Rf 0.29 (dichloromethane:methanol:28% ammonia water=80:20:4);
NMR (CD$_3$OD): δ 1.10-1.46 (m, 4H), 1.60-2.07 (m, 1H), 2.17 (dd, J=13.0, 8.6 Hz, 1H), 2.63 (d, J=9.9 Hz, 1H), 2.72-3.09 (m, 5H), 3.15 (d, J=9.9 Hz, 1H), 3.46-3.56 (m, 6H), 3.65 (s, 4H), 3.84 (d, J=12.8 Hz, 1H), 4.20 (d, J=12.8 Hz, 1H), 6.83 (d, J=1.3 Hz, 1H), 6.96 (d, J=1.3 Hz, 1H), 7.00 (s, 2H), 7.28 (d, J=8.2 Hz, 2H), 7.37 (d, J=8.2 Hz, 2H);
Specific rotation: $[\alpha]_D^{25}$=+30.9 (c=0.20, methanol).

Example 37(5)

(3S)-8-cyclohexyl-2-[4-({(1H-imidazol-2-ylmethyl)[(1-methyl-1H-imidazol-2-yl)methyl]amino}methyl)benzyl]-2,8-diazaspiro[4.5]decane-3-carboxylic acid TLC: Rf 0.29 (dichloromethane:methanol:28% ammonia water=80:20:4);
NMR (CD$_3$OD): δ 1.06-1.42 (m, 4H), 1.50-2.01 (m, 1H), 2.08 (dd, J=12.9, 8.6 Hz, 1H), 2.40 (d, J=10.2 Hz, 1H), 2.65-2.77 (m, 1H), 2.78-2.93 (m, 4H), 3.01 (d, J=10.2 Hz, 1H), 3.33-3.40 (m, 1H), 3.49 (s, 3H), 3.51 (s, 2H), 3.57-3.71 (m, 5H), 4.13 (d, J=12.8 Hz, 1H), 6.83 (d, J=1.3 Hz, 1H), 6.96 (d, J=1.3 Hz, 1H), 6.99 (s, 2H), 7.25 (d, J=8.1 Hz, 2H), 7.35 (d, J=8.1 Hz, 2H);
Specific rotation: $[\alpha]_D^{25}$=−28.8 (c=0.32, methanol).

Example 37(6)

(3R)-8-(1-ethylpropyl)-2-[4-({(1H-imidazol-2-ylmethyl)[(1-methyl-1H-imidazol-2-yl)methyl]amino}methyl)benzyl]-2,8-diazaspiro[4.5]decane-3-carboxylic acid TLC: Rf 0.25 (dichloromethane:methanol:28% ammonia water=50:10:1);
NMR (CD$_3$OD): δ 0.93 (t, J=7.2 Hz, 6H), 1.36-1.82 (m, 8H), 1.93 (dd, J=12.9, 8.1 Hz, 1H), 2.17 (12.9, 8.1 Hz, 1H), 2.42 (m, 1H), 2.60-2.80 (m, 5H), 3.20 (m, 1H), 3.49 (s, 3H), 3.53 (s, 2H), 3.58-3.70 (m, 5H), 3.95 (m, 1H), 4.24 (d, J=12.9H, 1H), 6.83 (d, J=1.2 Hz, 1H), 6.96 (d, J=1.2 Hz, 1H), 7.00 (s, 2H), 7.28 (d, J=8.1 Hz, 2H), 7.38 (d, J=8.1 Hz, 2H);
Specific rotation: $[\alpha]_D^{25}$=+32.3 (c=1.09, methanol).

Example 37(7)

(3S)-8-(1-ethylpropyl)-2-[4-({(1H-imidazol-2-ylmethyl)[(1-methyl-1H-imidazol-2-yl)methyl]amino}methyl)benzyl]-2,8-diazaspiro[4.5]decane-3-carboxylic acid TLC: Rf 0.25 (dichloromethane:methanol:28% ammonia water=50:10:1);
NMR (CD$_3$OD): δ 0.93 (t, J=7.2 Hz, 6H), 1.36-1.82 (m, 8H), 1.95 (dd, J=12.9, 8.1 Hz, 1H), 2.17 (12.9, 8.1 Hz, 1H), 2.42 (m, 1H), 2.60-2.80 (m, 5H), 3.20 (m, 1H), 3.49 (s, 3H), 3.53 (s, 2H), 3.58-3.70 (m, 5H), 3.95 (m, 1H), 4.24 (d, J=12.9H, 1H), 6.83 (d, J=1.2 Hz, 1H), 6.96 (d, J=1.2 Hz, 1H), 7.00 (s, 2H), 7.28 (d, J=8.1 Hz, 2H), 7.38 (d, J=8.1 Hz, 2H);
Specific rotation: [α]$_D^{25}$=−30.6 (c=1.03, methanol).

Example 38

1-[4-(diethoxymethyl)phenyl]-N,N-bis[(1-methyl-1H-imidazol-2-yl)methyl]methaneamine The same procedure as in Example 3 was carried out, except that 1-(1-methyl-1H-imidazol-2-yl)-N-[(1-methyl-1H-imidazol-2-yl)methyl]methaneamine (International Publication WO 2007/058322 pamphlet, Example 58) was used in place of the compound obtained in Example 2, and 4-(diethoxymethyl)benzaldehyde (CAS Registry Number: 81172-89-6) was used in place of isobutylaldehyde in Example 3, the title compound having the following physical properties was obtained.
TLC: Rf 0.39 (ethyl acetate:methanol:28% ammonia water=80:10:2);
NMR (CDCl$_3$): δ 1.19-1.29 (m, 6H), 3.27 (s, 6H), 3.44-3.61 (m, 4H), 3.62 (s, 2H), 3.68 (s, 4H), 5.48 (s, 1H), 6.78 (d, J=1.3 Hz, 2H), 6.92 (d, J=1.3 Hz, 2H), 7.20 (d, J=7.9 Hz, 2H), 7.39 (d, J=7.9 Hz, 2H).

Example 39

4-({bis[(1-methyl-1H-imidazol-2-yl)methyl]amino}methyl)benzaldehyde

The same procedure as in Example 25 was carried out, except that the compound obtained in Example 38 was used in placed of 2,2'-[{[4-(diethoxymethyl)benzyl]imino}bis(methylene)]bis(N,N-dimethyl-1H-imidazole-1-sulfonamide) in Example 25, the title compound having the following physical properties was obtained.
TLC: Rf 0.30 (ethyl acetate:methanol:28% ammonia water=80:10:2);
NMR (CDCl$_3$): δ 3.33 (s, 6H), 3.70 (s, 4H), 3.76 (s, 2H), 6.79 (d, J=1.3 Hz, 2H), 6.93 (d, J=1.3 Hz, 2H), 7.38 (d, J=8.1 Hz, 2H), 7.80 (d, J=8.1 Hz, 2H), 9.97 (s, 1H).

Example 40

8-tert-butyl 3-ethyl 2-[4-({bis[(1-methyl-1H-imidazol-2-yl)methyl]amino}methyl)benzyl]-2,8-diazaspiro[4.5]decane-3,8-dicarboxylate The same procedure was carried out, except that the compound obtained in Example 39 was used in place of 4-{[bis(1H-imidazol-2-ylmethyl)amino]methyl}benzaldehyde in Example 1, the title compound having the following physical properties was obtained.

TLC: Rf 0.53 (dichloromethane:methanol:28% ammonia water=80:10:2);
NMR (CDCl$_3$): δ 1.26 (t, J=7.0 Hz, 3H), 1.39-1.47 (m, 2H), 1.43 (s, 9H), 1.55-1.63 (m, 2H), 1.80-1.89 (m, 1H), 1.91-2.00 (m, 1H), 2.19 (d, J=9.2 Hz, 1H), 2.83 (d, J=9.2 Hz, 1H), 3.22-3.38 (m, 1H), 3.44 (d, J=13.2 Hz, 1H), 3.60 (s, 2H), 3.66 (s, 4H), 3.93 (d, J=13.2 Hz, 1H), 4.12 (q, J=7.0 Hz, 2H), 6.79 (d, J=1.3 Hz, 2H), 6.91 (d, J=1.3 Hz, 2H), 7.14 (d, J=8.1 Hz, 214), 7.24 (d, J=8.1 Hz, 2H).

Example 41

Ethyl 2-[4-({bis[(1-methyl-1H-imidazol-2-yl)methyl]amino}methyl)benzyl]-2,8-diazaspiro[4.5]decane-3-carboxylate The same procedure as in Example 2 was carried out, except that the compound obtained in Example 40 was used in place of the compound obtained in Example 1 in Example 2, the title compound having the following physical properties was obtained.
Rf 0.46 (chloroform:methanol: 28% ammonia water=40:10:2);
TLC: NMR (CDCl$_3$): δ 1.20-1.29 (m, 3H), 1.43 (t, J=5.6 Hz, 2H), 1.55-1.63 (m, 2H), 1.78-1.89 (m, 1H), 1.91-2.01 (m, 1H), 2.17 (d, J=9.2 Hz, 1H), 2.65-2.81 (m, 4H), 2.85 (d, J=9.2 Hz, 1H), 3.23-3.36 (m, 1H), 3.27 (s, 6H), 3.43 (d, J=13.2 Hz, 1H), 3.60 (s, 2H), 3.67 (s, 4H), 3.93 (d, J=13.2 Hz, 1H), 4.07-4.19 (m, 2H), 6.78 (d, J=1.3 Hz, 2H), 6.91 (d, J=1.3 Hz, 2H), 7.14 (d, J=8.1 Hz, 2H), 7.25 (d, J=8.1 Hz, 2H).

Example 42

Ethyl 2-[4-({bis[(1-methyl-1H-imidazol-2-yl)methyl]amino}methyl)benzyl]-8-(2,2-dimethylpropyl)-2,8-diazaspiro[4.5]decane-3-carboxylate The same procedure as in Example 3 was carried out, except that the compound obtained in Example 41 was used in place of the compound obtained in Example 2, and trimethylacetoaldehyde was used in place of isobutylaldehyde in Example 3, the title compound having the following physical properties was obtained.
TLC: Rf 0.56 (ethyl acetate:methanol:28% ammonia water=80:10:2);
NMR (CDCl$_3$): δ 0.82 (s, 9H), 1.25 (t, J=7.1 Hz, 3H), 1.45 (t, J=5.3 Hz, 2H), 1.60 (t, J=5.3 Hz, 2H), 1.73-1.82 (m, 1H), 1.86-1.96 (m, 1H), 1.95 (s, 2H), 2.14 (d, J=9.2 Hz, 1H), 2.28-2.45 (m, 4H), 2.82 (d, J=9.2 Hz, 1H), 3.24-3.33 (m, 7H), 3.41 (d, J=13.2, 1H), 3.60 (s, 2H), 3.67 (s, 4H), 3.92 (d, J=13.2 Hz, 1H), 4.07-4.19 (m, 2H), 6.78 (d, J=1.3 Hz, 2H), 6.92 (d, J=1.3 Hz, 2H), 7.14 (d, J=8.1 Hz, 2H), 7.25 (d, J=8.1 Hz, 2H).

Example 43

2-[4-({bis[(1-methyl-1H-imidazol-2-yl)methyl]amino}methyl)benzyl]-8-(2,2-dimethylpropyl)-2,8-diazaspiro[4.5]decane-3-carboxylic acid The same procedure as in Example 32 was carried out, except that the compound obtained in Example 42 was used in place of the compound obtained in Example 8 in Example 32, the title compound having the following physical properties was obtained.
TLC: Rf 0.66 (dichloromethane:methanol:28% ammonia water=40:10:2);

NMR (CD₃OD): δ 0.87 (s, 9H), 1.54-1.75 (m, 4H), 1.97-2.08 (m, 1H), 2.13 (s, 2H), 2.19-2.32 (m, 1H), 2.52 (s, 4H), 2.92 (d, J=10.4 Hz, 1H), 3.35 (s, 6H), 3.35-3.44 (m, 1H), 3.56 (s, 2H), 3.66 (s, 4H), 3.76-3.87 (m, 1H), 4.18 (d, J=12.6 Hz, 1H), 4.30 (d, J=12.6 Hz, 1H), 6.85 (d, 0.7 Hz, 2H), 7.00 (d, J=0.7 Hz, 2H), 7.19 (d, J=8.1 Hz, 2H), 7.42 (d, J=8.1 Hz, 2H).

Example 44

Methyl 2-(4-{[bis(1H-imidazol-2-ylmethyl)amino]methyl}benzyl)-8-cyclohexyl-2,8-diazaspiro[4.5]decane-3-carboxylate The compound (102 mg) obtained in Example 5(1) was dissolved in methanol (1 mL) and, furthermore, thionyl chloride (0.25 mL) was added at 0° C. The reaction solution was stirred at 60° C. for 1 hour. The reaction solution was concentrated under reduced pressure and the residue was purified by silica gel chromatography (manufactured by Fuji Silysia Chemical Ltd., CHROMATOREX NH (trade name)) (dichloromethane:methanol=1:0→4:1) to obtain the title compound (96.4 mg) having the following physical properties.

TLC: Rf 0.36 (dichloromethane:methanol:28% ammonia water=90:10:1);

NMR (CDCl₃): δ 0.97-1.34 (m, 6H), 1.43-1.89 (m, 9H), 1.95 (dd, J=13.0, 8.1 Hz, 1H), 2.15-2.29 (m, 1H), 2.24 (d, J=9.7 Hz, 1H), 2.31-2.57 (m, 4H), 2.97 (d, J=9.7 Hz, 1H), 3.33 (t, J=8.1 Hz, 1H), 3.56-3.61 (m, 1H), 3.61 (s, 4H), 3.61 (s, 3H), 3.66 (s, 2H), 3.80 (d, J=13.0 Hz, 1H), 7.06 (s, 4H), 7.22-7.35 (m, 4H).

Example 44(1) to 44(4)

The same procedure as in Example 44, except that corresponding compound was used in place of the compound obtained in Example 5(1) in Example 44, the following compounds were obtained.

Example 44(1)

Methyl (3S)-2-(4-{[bis(1H-imidazol-2-ylmethyl)amino]methyl}benzyl)-8-(2,2-dimethylpropyl)-2,8-diazaspiro[4.5]decane-3-carboxylate TLC: Rf 0.29 (dichloromethane:methanol:28% ammonia water=90:10:1);

NMR (CDCl₃): δ 0.82 (s, 9H), 1.42-1.52 (m, 2H), 1.58-1.66 (m, 2H), 1.77 (dd, J=12.9, 8.1 Hz, 1H), 1.94 (dd, J=12.9, 8.1 Hz, 1H), 1.96 (s, 2H), 2.22 (d, J=9.3 Hz, 1H), 2.30-2.45 (m, 4H), 2.96 (d, J=9.3 Hz, 1H), 3.31 (t, J=8.1 Hz, 1H), 3.50-3.68 (m, 10H), 3.80 (d, J=12.9 Hz, 1H), 7.04 (s, 4H), 7.24-7.34 (m, 4H);

Specific rotation: $[\alpha]_D^{25}$=−38.4 (c=0.65, chloroform).

Example 44(2)

Methyl 2-(4-{[bis(1H-imidazol-2-ylmethyl)amino]methyl}benzyl)-8-(2,2-dimethylpropyl)-2,8-diazaspiro[4.5]decane-3-carboxylate TLC: Rf 0.42 (dichloromethane:methanol:28% ammonia water=90:10:1);

NMR (CDCl₃): δ 0.82 (s, 9H), 1.42-1.52 (m, 2H), 1.58-1.66 (m, 2H), 1.77 (dd, J=12.8, 8.1 Hz, 1H), 1.96 (dd, J=12.8, 8.1 Hz, 1H), 1.96 (s, 2H), 2.22 (d, J=9.3 Hz, 1H), 2.28-2.47 (m, 4H), 2.96 (d, J=9.3 Hz, 1H), 3.31 (t, J=8.1 Hz, 1H), 3.55 (d, J=12.8 Hz, 1H), 3.60 (s, 4H), 3.61 (s, 3H), 3.64 (s, 2H), 3.79 (d, J=12.8 Hz, 1H), 7.05 (s, 4H), 7.22-7.33 (m, 4H).

Example 44(3)

Methyl 8-(1-ethylpropyl)-2-[4-({(1H-imidazol-2-ylmethyl)[(1-methyl-1H-imidazol-2-yl)methyl]amino}methyl)benzyl]-2,8-diazaspiro[4.5]decane-3-carboxylate TLC: Rf 0.41 (dichloromethane:methanol:28% ammonia water=90:10:1);

NMR (CDCl₃): δ 0.85 (t, J=7.3 Hz, 6H), 1.15-1.71 (m, 8H), 1.79 (dd, J=12.8, 8.2 Hz, 1H), 1.93 (dd, J=12.8, 8.2 Hz, 1H), 2.01-2.14 (m, 1H), 2.19 (d, J=9.1 Hz, 1H), 2.25-2.48 (m, 4H), 2.89 (d, J=9.1 Hz, 1H), 3.33 (t, J=8.2 Hz, 1H), 3.45 (s, 2H), 3.48 (d, J=13.2 Hz, 1H), 3.54 (s, 3H), 3.62 (s, 2H), 3.65 (s, 3H), 3.67 (s, 2H), 3.89 (d, J=13.2 Hz, 1H), 6.86 (d, J=1.3 Hz, 1H), 6.99 (d, J=1.3 Hz, 1H), 7.04-7.14 (m, 2H), 7.26 (d, J=8.2 Hz, 2H), 7.33 (d, J=8.2 Hz, 2H), 12.22-12.37 (m, 1H).

Example 44(4)

Methyl (3S)-2-(4-{[bis(1H-imidazol-2-ylmethyl)amino]methyl}benzyl)-8-(1-ethylpropyl)-2,8-diazaspiro[4.5]decane-3-carboxylate TLC: Rf 0.22 (dichloromethane:methanol:28% ammonia water=90:10:1);

NMR (CDCl₃): δ 0.86 (t, J=7.3 Hz, 6H), 1.14-1.32 (m, 2H), 1.34-1.55 (m, 4H), 1.56-1.66 (m, 2H), 1.71-1.83 (m, 1H), 1.87-2.00 (m, 1H), 2.03-2.14 (m, 1H), 2.23 (d, J=9.3 Hz, 1H), 2.29-2.48 (m, 4H), 2.96 (d, J=9.3 Hz, 1H), 3.32 (t, J=8.1 Hz, 1H), 3.56 (d, J=13.0 Hz, 1H), 3.59-3.63 (m, 7H), 3.64 (s, 2H), 3.80 (d, J=13.0 Hz, 1H), 7.06 (s, 4H), 7.21-7.33 (m, 4H);

Specific rotation: $[\alpha]_D^{25}$=−43.2 (c=0.88, chloroform).

Example 45

2-(dimethylamino)-2-oxoethyl (3S)-2-(4-{[bis(1H-imidazol-2-ylmethyl)amino]methyl}benzyl)-8-(2,2-dimethylpropyl)-2,8-diazaspiro[4.5]decane-3-carboxylate To an N,N-dimethylformamide (1 mL) solution of the compound (80 mg) obtained in Example 32(5), 2-hydroxy-N,N-dimethylacetoamide (CAS Registry Number: 14658-93-6; 77 mg), diisopropylethylamine (39 μL) and N,N,N',N'-tetramethyl-O-(7-azobenzotriazol-1-yl)uronium hexafluorophosphate (86 mg) were added. The reaction solution was stirred at room temperature for 16 hours. To this solution, an aqueous saturated sodium hydrogen carbonate solution was added, and the solution was extracted with ethyl acetate. The organic layer was washed with saturated brine and then dried over anhydrous sodium sulfate, and concentrated under reduced pressure. The residue was purified by silica gel chromatography (CHROMATOREX NH (trade name), manufactured by Fuji Silysia Chemical Ltd.) (ethyl acetate:methanol=1:0→30:1→15:1) to obtain the title compound (68 mg) having the following physical properties.

TLC: Rf 0.22 (dichloromethane:methanol:28% ammonia water=90:10:1);

NMR (CDCl₃): δ 0.82 (s, 9H), 1.42-1.52 (m, 2H), 1.60-1.68 (m, 2H), 1.90 (dd, J=12.9, 8.1 Hz, 1H), 1.97 (s, 2H), 2.01 (dd, J=12.9, 8.1 Hz, 1H), 2.27 (d, J=9.0 Hz, 1H), 2.30-2.50 (m, 4H), 2.91 (s, 3H), 2.95 (s, 3H), 2.99 (d, J=9.0 Hz, 1H), 3.41 (t, J=8.1 Hz, 1H), 3.53-3.70 (m, 7H), 3.83 (d, J=12.9 Hz, 1H), 4.59 (d, J=14.4 Hz, 1H), 4.65 (d, J=14.4 Hz, 1H), 7.05 (s, 4H), 7.23-7.29 (m, 4H);

Specific rotation: $[\alpha]_D^{25}$=−41.8 (c=1.00, chloroform).

Example 45(1) to 45(6)

The same procedure as in Example 45, except that corresponding compounds were respectively used in place of the compound obtained in Example 32(5) and 2-hydroxy-N,N-dimethylacetoamide in Example 45, the following title compound was obtained.

Example 45(1)

2-(diethylamino)-2-oxoethyl (3S)-2-(4-{[bis(1H-imidazol-2-ylmethyl)amino]methyl}benzyl)-8-(1-ethylpropyl)-2,8-diazaspiro[4.5]decane-3-carboxylate TLC: Rf 0.63 (dichloromethane:methanol:28% ammonia water=80:20:2);

NMR (CDCl$_3$): δ 0.85 (t, J=7.3 Hz, 6H), 1.11 (t, J=7.0 Hz, 3H), 1.15-1.33 (m, 5H), 1.33-1.53 (m, 4H), 1.62 (t, J=5.1 Hz, 2H), 1.82-1.93 (m, 1H), 1.94-2.15 (m, 2H), 2.24 (d, J=9.2 Hz, 1H), 2.28-2.52 (m, 4H), 2.95 (d, J=9.2 Hz, 1H), 3.23 (q, J=7.1 Hz, 2H), 3.30-3.48 (m, 3H), 3.48-3.71 (m, 7H), 3.86 (d, J=13.2 Hz, 1H), 4.55-4.74 (m, 2H), 7.03 (s, 4H), 7.14-7.24 (m, 4H).

Example 45(2)

2-oxo-2-(1-pyrrolidinyl)ethyl (3S)-2-(4-{[bis(1H-imidazol-2-ylmethyl)amino]methyl}benzyl)-8-(1-ethylpropyl)-2,8-diazaspiro[4.5]decane-3-carboxylate TLC: Rf 0.63 (dichloromethane:methanol:28% ammonia water=80:20:2);

NMR (CDCl$_3$): δ 0.86 (t, J=7.4 Hz, 6H), 1.14-1.34 (m, 2H), 1.34-1.56 (m, 4H), 1.64 (t, J=5.3 Hz, 2H), 1.75-2.15 (m, 7H), 2.28 (d, J=9.2 Hz, 1H), 2.31-2.50 (m, 4H), 2.98 (d, J=9.2 Hz, 1H), 3.29-3.43 (m, 3H), 3.44-3.52 (m, 2H), 3.52-3.73 (m, 7H), 3.82 (d, J=13.2 Hz, 1H), 4.40-4.66 (m, 2H), 7.04 (s, 4H), 7.19-7.25 (m, 4H).

Example 45(3)

2-(4-morpholinyl)ethyl (3S)-2-(4-{[bis(1H-imidazol-2-ylmethyl)amino]methyl}benzyl)-8-(2,2-dimethylpropyl)-2,8-diazaspiro[4.5]decane-3-carboxylate TLC: Rf 0.35 (dichloromethane:methanol:28% ammonia water=90:10:1);

NMR (CDCl$_3$): δ 0.83 (s, 9H), 1.45-1.54 (m, 2H), 1.62-1.70 (m, 2H), 1.80-2.00 (m, 2H), 1.98 (s, 2H), 2.15 (d, J=9.0 Hz, 1H), 2.30-2.51 (m, 8H), 2.55-2.64 (m, 2H), 3.00 (d, J=9.6 Hz, 1H), 3.33 (t, J=8.1 Hz, 1H), 3.48-3.74 (m, 1H), 3.95 (d, J=13.2 Hz, 1H), 4.10-4.28 (m, 2H), 7.06 (s, 4H), 7.25-7.31 (m, 4H);

Specific rotation: $[\alpha]_D^{25}$=−37.1 (c=0.33, chloroform).

Example 45(4)

Butyl (3S)-2-(4-{[bis(1H-imidazol-2-ylmethyl)amino]methyl}benzyl)-8-(2,2-dimethylpropyl)-2,8-diazaspiro[4.5]decane-3-carboxylate TLC: Rf 0.44 (dichloromethane:methanol:28% ammonia water=90:10:1);

NMR (CDCl$_3$): δ 0.82 (s, 9H), 0.91 (t, J=7.2 Hz, 3H), 1.26-1.67 (m, 8H), 1.77 (dd, J=12.9, 8.1 Hz, 1H), 1.88 (dd, J=12.9, 8.1 Hz, 1H), 1.96 (s, 2H), 2.20 (d, J=9.0 Hz, 1H), 2.30-2.48 (m, 4H), 2.93 (d, J=9.0 Hz, 1H), 3.30 (t, J=8.1 Hz, 1H), 3.54 (d, J=12.9 Hz, 1H), 3.61 (s, 4H), 3.64 (s, 2H), 3.84 (d, J=12.9 Hz, 1H), 4.00 (t, J=6.6 Hz, 2H), 7.05 (s, 4H), 7.24-7.32 (m, 4H);

Specific rotation: $[\alpha]_D^{25}$=−39.6 (c=1.00, chloroform).

Example 45(5)

Propyl (3S)-2-(4-{[bis(1H-imidazol-2-ylmethyl)amino]methyl}benzyl)-8-(2,2-dimethylpropyl)-2,8-diazaspiro[4.5]decane-3-carboxylate TLC: Rf 0.42 (dichloromethane:methanol:28% ammonia water=90:10:1);

NMR (CDCl$_3$): δ 0.82 (s, 9H), 0.92 (t, J=7.2 Hz, 3H), 1.40-1.54 (m, 2H), 1.55-1.70 (m, 4H), 1.77 (dd, J=12.9, 8.1 Hz, 1H), 1.93 (dd, J=12.9, 8.1 Hz, 1H), 1.96 (s, 2H), 2.20 (d, J=9.0 Hz, 1H), 2.30-2.46 (m, 4H), 2.93 (d, J=9.0 Hz, 1H), 3.30 (t, J=8.1 Hz, 1H), 3.52 (d, J=12.9 Hz, 1H), 3.60 (s, 4H), 3.63 (s, 2H), 3.83 (d, J=12.9 Hz, 1H), 3.97 (t, J=6.6 Hz, 2H), 7.04 (s, 4H), 7.20-7.30 (m, 4H);

Specific rotation: $[\alpha]_D^{25}$=−41.3 (c=1.02, chloroform).

Example 45(6)

Isopropyl (3S)-2-(4-{[bis(1H-imidazol-2-ylmethyl)amino]methyl}benzyl)-8-(2,2-dimethylpropyl)-2,8-diazaspiro[4.5]decane-3-carboxylate TLC: Rf 0.37 (dichloromethane:methanol:28% ammonia water=90:10:1);

NMR (CDCl$_3$): δ 0.82 (s, 9H), 1.19-1.28 (m, 6H), 1.40-1.52 (m, 2H), 1.58-1.66 (m, 2H), 1.74 (dd, J=12.9, 8.1 Hz, 1H), 1.92 (dd, J=12.9, 8.1 Hz, 1H), 1.96 (s, 2H), 2.19 (d, J=9.3 Hz, 1H), 2.28-2.47 (m, 4H), 2.92 (d, J=9.3 Hz, 1H), 3.27 (t, J=8.1 Hz, 1H), 3.50 (d, J=12.9 Hz, 1H), 3.60 (s, 4H), 3.65 (s, 2H), 3.87 (d, J=12.9 Hz, 1H), 4.95 (m, 1H), 7.05 (s, 4H), 7.23-7.34 (m, 4H);

Specific rotation: $[\alpha]_D^{25}$=−40.7 (c=1.03, chloroform).

Reference Example 1

1-(4-{[8-[1-ethylpropyl]-2,8-diazaspiro[4.5]deca-2-yl)methyl}phenyl]-N,N-bis(1H-imidazol-2-ylmethyl)methaneamine 4-{[bis(1H-imidazol-2-ylmethyl)amino]methyl}benzaldehyde (International Publication WO 2007/058322 pamphlet, Example 28; 169 mg) was dissolved in dimethylformamide (4 mL), and 4 droplets of acetic acid, 8-(1-ethylpropyl)-2,8-diazaspiro[4.5]decane dihydrochloride (100 mg) and sodium triacetoxyborohydride (151 mg) were sequentially added thereto, followed by stirring at room temperature for 2 hours. After completion of the reaction, an aqueous saturated sodium hydrogen carbonate solution was added, followed by stirring for a while and extracted with ethyl acetate. The organic layer was washed with water and brine, dried over magnesium sulfate and then concentrated. The residue was purified by silica gel column chromatography (FL60D (trade name), manufactured by Fuji Silysia Chemical Ltd.) (ethyl acetate:methanol:28% ammonia water=9:1→ethyl acetate:methanol:28% ammonia water=80:10:2) to obtain the title compound (127 mg) having the following physical properties.

TLC: Rf 0.61 (ethyl acetate:methanol:ammonia water=80:10:2);

NMR (CD$_3$OD): δ 0.86 (t, J=7.41 Hz, 6H), 1.19-1.34 (m, 2H), 1.36-1.63 (m, 8H), 2.00-2.17 (m, 1H), 2.31-2.44 (m, 4H), 2.35 (s, 2H), 2.53 (t, J=6.86 Hz, 2H), 3.52 (s, 2H), 3.55 (s, 2H), 3.57 (s, 4H), 7.01 (s, 4H), 7.18 (d, J=8.10 Hz, 2H), 7.22 (d, J=8.10 Hz, 2H)

Reference Example 2

5-{[bis(1H-imidazol-2-ylmethyl)amino]methyl}-2-[(8-cyclohexyl-2,8-diazaspiro[4.5]deca-2-yl)methyl]benzenecarboxylic acid Under an argon atmosphere, 3-bromo-4-methylbenzenecarboxylic acid (CAS Registry Number: 7697-26-9; 15.3 g) was dissolved in a tetrahydrofuran-methanol (100 mL-50 mL) mixed solvent and trimethylsilyldiazomethane (2M hexane solution) (42.7 mL) was added, followed by stirring at room temperature for 1 hour. To the reaction solution, the reagent was decomposed by adding acetic acid (1 mL) and water (100 mL) was added, and the solution was extracted twice with ethyl acetate (100 mL). The organic layers were combined, washed with saturated brine and then dried over anhydrous magnesium sulfate. Anhydrous magnesium sulfate was removed by filtration and then the filtrate was concentrated. The residue was purified by silica gel chromatography (ethyl acetate) to obtain an ester compound (12.9 g).

Under an argon atmosphere, an ester compound (10.0 g) was dissolved in carbon tetrachloride (100 mL). Subsequently, N-bromosuccinimide (8.17 g) and benzoyl peroxide (2.12 g) were added, followed by stirring at 75° C. for 4 hours. After completion of the reaction, aqueous sodium hydrogen carbonate (50 mL) was added and the solution was extracted twice with dichloromethane (100 mL). The organic layers were combined, washed with saturated brine and then dried over anhydrous magnesium sulfate. After removing anhydrous magnesium sulfate by filtration, the filtrate was concentrated to obtain a brominated compound (13.1 g).

Under an argon atmosphere, the brominated compound (8.72 g) and tert-butyl 2,8-diazaspiro[4.5]decane-2-carboxylate (8.39 g) were dissolved in acetone (100 mL). Subsequently, potassium carbonate (8.04 g) was added, followed by stirring at 50° C. for 4 hours. After completion of the reaction, water (50 mL) was added, followed by extraction twice with ethyl acetate (100 mL). The organic layers were combined, washed with saturated brine and then dried over anhydrous magnesium sulfate. After removing anhydrous magnesium sulfate by filtration, the filtrate was concentrated to obtain a compound (9.49 g).

Under an argon atmosphere, the compound (5.00 g) was dissolved in tetrahydrofuran (80 mL), followed by cooling to 0° C. Subsequently, lithium aluminum hydride (812 mg) was added, followed by stirring at 0° C. for 30 minutes. After completion of the reaction, ice water (50 mL) was added, followed by extraction twice with ethyl acetate (50 mL). The organic layers were combined, washed with saturated brine and then dried over anhydrous magnesium sulfate. After removing anhydrous magnesium sulfate by filtration, the filtrate was concentrated to obtain an alcohol compound (4.39 g).

Under an argon atmosphere, an alcohol compound (3.00 g) was dissolved in a dimethyl sulfoxide-methanol (20 mL-10 mL) mixed solvent and then triethylamine (1.90 mL) was added. The atmosphere in the reaction system was deaerated by a water-jet aspirator and replaced again by argon. 1,3-bisdiphenylphosphinopropane (282 mg) and palladium acetate (153 mg) were added and then the atmosphere in the reaction system was replaced by carbon monoxide, followed by stirring at 100° C. for 20 hours. To the reaction solution, water (30 mL) was added, followed by extraction twice with dichloromethane (50 mL). The organic layers were combined, washed with saturated brine and then dried over anhydrous magnesium sulfate. After removing anhydrous magnesium sulfate by filtration, the filtrate was concentrated and the resultant residue was purified by silica gel column chromatography (hexane:ethyl acetate=5:1→0:1 ethyl acetate:methanol=0:1→10:1) to obtain an ester compound (923 mg).

Under an argon atmosphere, the ester compound (923 mg) was dissolved in dichloromethane (10 mL) and then Dess-Martin Periodinane (1.12 g) was added, followed by stirring at room temperature for 3 hours. To the reaction solution, ice water (50 mL) was added, followed by extraction twice with ethyl acetate (50 mL). The organic layers were combined, washed with saturated brine and then dried over anhydrous magnesium sulfate. After removing anhydrous magnesium sulfate by filtration, the filtrate was concentrated to obtain a crude product (1.43 g) of an aldehyde compound.

Under an argon atmosphere, the aldehyde compound (crude 1.34 g) and 2,2'-[iminobis(methylene)]bis(N,N-dimethyl-1H-imidazole-1-sulfonamide) (International Publication WO 2007/058322 pamphlet, Example 3; 1.04 g) were dissolved in dimethylformamide (10 mL) and then acetic acid (1 mL) was added, followed by stirring for 1 hour. Then, sodium triacetoxyborohydride (937 mg) was added, followed by stirring at room temperature for 3 hours. After completion of the reaction, water (20 mL) was added, followed by stirring for 1 hour and then extraction twice with dichloromethane (20 mL). The organic layers were combined, washed with saturated brine and then dried over anhydrous magnesium sulfate. After removing anhydrous magnesium sulfate by filtration, the filtrate was concentrated and the resultant residue was purified by silica gel column chromatography (hexane:ethyl acetate=2:1→1:2→ethyl acetate:methanol:28% ammonia water=20:1:0→10:1:2) to obtain a crude product of an amino compound (1.21 g).

Under an argon atmosphere, the amino compound (crude 1.21 g) was dissolved in dichloromethane (10 mL) and then trifluoroacetic acid (5 mL) was added, followed by stirring at room temperature for 2 hours. After completion of the reaction, the reaction solution was concentrated and diluted with dichloromethane (20 mL) and then washed with aqueous saturated sodium hydrogen carbonate (10 mL) and saturated brine, and dried over anhydrous magnesium sulfate. After removing anhydrous magnesium sulfate by filtration, the filtrate was concentrated and the resultant residue was purified by silica gel column chromatography (ethyl acetate:methanol:28% ammonia water=100:10:0→80:20:4) to obtain an amino compound (330 mg).

Under an argon atmosphere, the amino compound (330 mg) and cyclohexanone (99 μL) were dissolved in dimethylformamide (5 mL) and then sodium triacetoxyborohydride (252 mg) was added, followed by stirring at room temperature for 18 hours. After completion of the reaction, water (10 mL) was added, followed by stirring for 1 hour. The aqueous layer was saturated with sodium chloride and extracted twice with dichloromethane (20 mL). The organic layers were combined and dried over anhydrous magnesium sulfate. After removing anhydrous magnesium sulfate by filtration, the filtrate was concentrated and the resultant residue was purified by silica gel column chromatography (ethyl acetate:methanol:28% ammonia water=100:10:0→80:20:2) to obtain an N-alkyl compound (330 mg).

N-alkyl compound (85 mg) was dissolved in a tetrahydrofuran-methanol (2 mL-2 mL) mixed solvent and then an aqueous 2N sodium hydroxide solution (2 mL) was added, followed by stirring at 50° C. for 15 hours. After completion of the reaction, an aqueous 1N hydrochloric acid solution was added until pH 7 to 8, and the aqueous layer was saturated with sodium chloride and extracted twice with dichloromethane (20 mL). The organic layers were combined and dried over anhydrous magnesium sulfate. After removing anhydrous magnesium sulfate by filtration, the filtrate was concentrated to obtain a carboxylic acid derivative (60 mg).

The carboxylic acid derivative (60 mg) was dissolved in methanol (3 mL) and then a 4N hydrochloric acid-dioxane solution (3 mL) was added, followed by stirring at 50° C. for 3 hours. After completion of the reaction, the reaction solution was concentrated and the resultant residue was purified by silica gel column chromatography (ethyl acetate:methanol:28% ammonia water=100:10:2→80:20:2→dichloromethane:methanol:28% ammonia water=80:20:2) to obtain the title compound (35 mg) having the following physical properties.

TLC: Rf 0.60 (dichloromethane:methanol:28% ammonia water=80:20:5);

NMR (CD$_3$OD): δ 1.02-2.00 (m, 16H), 2.39 (m, 1H), 2.52-2.75 (m, 4H), 3.01 (brs, 2H), 3.15-3.30 (m, 2H), 3.57 (s, 2H), 3.68 (s, 4H), 4.24 (s, 2H), 6.97 (s, 4H), 7.30 (d, J=7.5 Hz, 1H), 7.39 (d, J=7.5 Hz, 1H), 7.90 (m, 1H).

Reference Example 3

8-(4-{[bis(1H-imidazol-2-ylmethyl)amino]methyl}benzyl)-2-(1-ethylpropyl)-2,8-diazaspiro[4.5]decane-3-carboxylic acid 8-tert-butyl 3-ethyl 2,8-diazaspiro[4.5]decane-3,8-dicarboxylate (Japanese Unexamined Patent Publication (Kokai) No. 2004-002470, Example 21f; 1.29 g) was dissolved in 3-pentanone (5.3 mL) and titanium tetraethoxide (1.3 mL) was added thereto, followed by stirring at 50° C. for 1 hour. After added tetrahydrofuran (20 mL) thereto, sodium triacetoxyborohydride (2.6 g) was slowly added, followed by stirring at 50° C. for 1 hour. After completion of the reaction, an aqueous saturated sodium hydrogen carbonate solution was added. After stirring for a while, precipitated insolubles were filtered with celite and the filtrate was extracted with ethyl acetate. The organic layer was washed with an aqueous saturated sodium hydrogen carbonate solution, water and brine, dried over magnesium sulfate and then concentrated. The residue was purified by silica gel column chromatography (FL60D (trade name), manufactured by Fuji Silysia Chemical Ltd.) (hexane:ethyl acetate=9:1) to obtain an alkyl compound (773 mg).

The alkyl compound (773 mg) was dissolved in ethanol (2 mL) and a 4N hydrogen chloride/dioxane solution (4 mL) was added thereto, followed by stirring at room temperature overnight. After completion of the reaction and concentration, the residue was purified by silica gel column chromatography (FL60D (trade name), manufactured by Fuji Silysia Chemical Ltd.) (ethyl acetate:methanol=9:1→ethyl acetate:methanol:28% ammonia water=80:10:2→dichloromethane:methanol:28% ammonia water=80:10:2) to obtain an amine compound (460 mg).

4-{[bis(1H-imidazol-2-ylmethyl)amino]methyl}benzaldehyde (International Publication WO 2007/058322 pamphlet, Example 28; 100 mg) was dissolved in dimethylformamide (4 mL), and acetic acid (4 droplets), an amine compound (115 mg) and sodium triacetoxyborohydride (108 mg) were sequentially added thereto, followed by stirring at room temperature overnight. After completion of the reaction, an aqueous saturated sodium hydrogen carbonate solution was added. After stirring for a while, the solution was extracted with ethyl acetate. The organic layer was washed with water and brine, dried over magnesium sulfate and then concentrated. The residue was purified by silica gel column chromatography (FL60D (trade name), manufactured by Fuji Silysia Chemical Ltd.) (ethyl acetate:methanol=9:1→ethyl acetate:methanol:28% ammonia water=80:10:2) to obtain an ester compound (157 mg).

The ester compound (157 mg) was dissolved in ethanol (2 mL) and an aqueous 2N sodium hydroxide solution (280 μL) was added thereto, followed by stirring at 70° C. overnight. After completion of the reaction and concentration, the residue was acidified by adding an aqueous 5N hydrochloric acid solution (0.5 mL) and then concentrated. Ethanol was added to this residue and the precipitated sodium chloride was removed by filtration, and a mother liquor was concentrated. This residue was purified by silica gel column chromatography (CHROMATOREX NH (trade name), manufactured by Fuji Silysia Chemical Ltd.) (ethyl acetate:methanol=9:1→dichloromethane:methanol=4:1) to obtain the title compound (122 mg) having the following physical properties.

TLC: Rf 0.57 (dichloromethane:methanol:ammonia water=40:10:2);

NMR (CD$_3$OD): δ 0.98-1.09 (m, 6H), 1.55-1.86 (m, 8H), 2.14 (dd, J=13.20, 10.06 Hz, 1H), 2.26 (dd, J=13.20, 4.03 Hz, 1H), 2.31-2.56 (m, 4H), 2.99 (d, J=11.71 Hz, 1H), 3.03-3.15 (m, 1H), 3.48 (s, 2H), 3.51 (s, 2H), 3.56 (d, J=11.71 Hz, 1H), 3.64 (s, 4H), 4.00 (dd, J=10.06, 4.03 Hz, 1H), 6.98 (s, 4H), 7.23 (d, J=8.10 Hz, 2H), 7.29 (d, J=8.10 Hz, 2H)

Reference Example 4

(3S)-2-(4-{[bis(1H-imidazol-2-ylmethyl)amino]methyl}benzyl)-8-(1-ethylpropyl)-2,8-diazaspiro[4.5]decane-3-carboxyamide Under an argon atmosphere, the compound (315 mg) obtained in Example 32(7) was dissolved in dimethylformamide (3 mL), and then 28% ammonia water (199 μL) and HATU (2-(1H-azabenzotriazol-1-yl)-1,1,3,3-tetramethyl uronium hexafluorophosphate methaneaminium) (337 mg) were added, followed by stirring at room temperature for 15 hours. After completion of the reaction, water (10 mL) and then an aqueous saturated sodium hydrogen carbonate were added, followed by extraction twice with dichloromethane (20 mL). The organic layers were combined, washed with saturated brine and then dried over anhydrous magnesium sulfate. After removing anhydrous magnesium sulfate by filtration, the filtrate was concentrated and the resultant residue was purified by silica gel column chromatography (CHROMATOREX NH (trade name), manufactured by Fuji Silysia Chemical Ltd.) (hexane:ethyl acetate=50:50→0:100→ethyl acetate:methanol=100:0→80:20) to obtain the title compound having the following physical properties (yield: 204 mg).

TLC: Rf 0.70 (dichloromethane:methanol:28% ammonia water=80:20:4);

NMR (CDCL$_3$): δ 0.86 (t, J=7.2 Hz, 6H), 1.18-2.16 (m, 1H), 2.28 (d, J=9.3 Hz, 1H), 2.30-2.46 (m, 4H), 3.04 (d, J=9.3 Hz, 1H), 3.18 (dd, J=11.2, 7.2 Hz, 1H), 3.58-3.64 (m, 4H), 3.65 (s, 2H), 3.67 (s, 2H), 5.38 (m, 1H), 6.91 (m, 1H), 7.04 (s, 4H), 7.21 (d, J=7.8 Hz, 2H), 7.30 (d, J=7.8 Hz, 2H).

Reference Example 5

2-(4-{[bis(1H-imidazol-2-ylmethyl)amino]methyl}benzyl)-8-(1-ethylpropyl)-2,8-diazaspiro[4.5]decane-4-carboxylic acid Under an argon atmosphere at 0° C., diethylphosphonoethyl acetate (CAS Registry Number: 867-13-0: 2.48 g) was dissolved in anhydrous tetrahydrofuran (30 mL) and sodium hydride (522 mg) was added dropwise. After stirring for 20 minutes, a solution prepared by dissolving 1-(tert-butoxycarbonyl)-4-piperidone (CAS Registry Number: 79099-07-3: 2 g) in anhydrous tetrahydrofuran (15 mL) was added dropwise, followed by stirring at room temperature for 3 hours. After adding dropwise water until termination of bubbling, the solvent was distilled off. After the addition of water and stirring, the solution was extracted with ethyl acetate. The organic layer was washed with water and saturated brine and then dried over anhydrous magnesium sulfate, and the solvent was distilled off. The residue was purified by silica gel column chromatography to obtain a carboxylic acid derivative (2.46 g).

Under an argon atmosphere at room temperature, carboxylic acid derivative and N-benzyl-1-methoxy-N-[(trimethylsilyl)methyl]methaneamine (CAS Registry Number: 93102-05-7; 958 mg) were dissolved in anhydrous toluene (13 mL) and trifluoroacetic acid (12.0 μL) was added, followed by stirring for 40 hours. After the addition of water and stirring, the solution was extracted with ethyl acetate. The organic layer was washed with saturated brine and then dried over anhydrous sodium sulfate, and the solvent was distilled off. The residue was purified by silica gel column chromatography to obtain a spiro compound (654 mg).

The spiro compound (600 mg) was dissolved in ethanol (7.5 mL) and a 4 N hydrochloric acid-ethyl acetate solution (7.5 mL) was added at room temperature. After stirring for 35 minutes, a 4N hydrochloric acid-ethyl acetate solution (7.5 mL) was further added, followed by stirring for 45 minutes. The solvent was distilled off to obtain an amine compound (430 mg).

Under an argon atmosphere at 50° C., an amine compound (421 mg), 3-pentanone (1.77 mL) and titanium tetraethoxide (0.44 mL) were added, followed by stirring for 1 hour. Dry tetrahydrofuran (7.0 mL) and sodium triacetoxyborohydride (885 mg) were added, followed by stirring for 40 minutes. The reaction solution was returned to room temperature and then an aqueous saturated sodium hydrogen carbonate solution was added, followed by stirring for 30 minutes. After filtration with celite, the filtrate was concentrated under reduced pressure. The residue was purified by column chromatography to obtain an N-alkyl compound (444 mg).

The N-alkyl compound (144 mg) was dissolved in ethanol (7.7 mL) at 50° C., and acetic acid (0.77 mL) and palladium-carbon hydroxide (70 mg) were added, followed by hydrogen substitution and further stirring for 1 hour. The reaction solution was filtered with celite and the filtrate was concentrated under reduced pressure. The residue was purified by column chromatography to obtain an amine compound (94 mg).

Under an argon atmosphere at room temperature, the amine compound (94 mg) and 4-{[bis(1H-imidazol-2-ylmethyl)amino]methyl}benzaldehyde (International Publication WO 2007/058322 pamphlet, Example 28; 98 mg) were dissolved in anhydrous dimethylformamide (3.3 mL) and acetic acid (50 μL), and sodium triacetoxyborohydride (106 mg) was added, followed by stirring for 1 hour. An aqueous saturated sodium carbonate solution was added and the solution was extracted with ethyl acetate. The organic layer was washed with water and saturated brine and then dried over anhydrous sodium sulfate, and the solvent was distilled off. The residue was purified by column chromatography to obtain a carboxylic acid derivative (103 mg).

The carboxylic acid derivative (65 mg) was dissolved in ethanol (1.2 mL) at 70° C. and an aqueous 2N sodium hydroxide solution (0.12 mL) was added, followed by stirring for 21 hours. Then, an aqueous 2N sodium hydroxide solution (0.12 mL) was further added, followed by stirring for 4 hours. The solvent was distilled off and an aqueous 5N hydrochloric acid solution (0.5 mL) was added to the residue. The solvent was distilled off and a desalination operation was carried out using ethanol, and then the residue was purified by column chromatograpy to obtain the title compound (51 mg) having the following physical properties.

TLC: Rf0.53 (dichloromethane:methanol:28% ammonia water=80:20:4); NMR (CD$_3$OD): δ 0.98 (td, J=7.4, 1.8 Hz, 6H), 1.46-1.66 (m, 2H), 1.66-1.86 (m, 4H), 1.88-2.06 (m, 1H), 2.08-2.25 (m, 1H), 2.54-2.69 (m, 2H), 2.69-2.97 (m, 5H), 2.98-3.09 (m, 1H), 3.13-3.28 (m, 2H), 3.52 (s, 2H), 3.65 (s, 4H), 3.71-3.85 (m, 2H), 6.99 (s, 4H), 7.32 (s, 4H)

Reference Example 6

2-(4-{[bis(1H-imidazol-2-ylmethyl)amino]methyl}benzyl)-8-isobutyl-2,8-diazaspiro[4.5]decane-7-carboxylic acid Benzylamine (3.0 g) was dissolved in acetonitrile (30 mL), and 4-bromo-1-butene (3.8 g) and triethylamine (4.7 mL) were added thereto, followed by stirring with heating at reflux for 8 hours. After completion of the reaction, the reaction solution was poured into ice water and the solution was extracted with ethyl acetate. The organic layer was washed with water and brine, dried over magnesium sulfate and then concentrated. The residue was purified by silica gel column chromatography (FL60D (trade name), manufactured by Fuji Silysia Chemical Ltd.) (hexane:ethyl acetate=4:1→ethyl acetate:methanol=9:1) to obtain an amine compound (2.8 g).

The amine compound (2.3 g) was dissolved in 40 mL of acetonitrile, and a molecular sieve 4A and glyoxylic acid (1.4 g) were added thereto, followed by stirring at room temperature for 5 hours. After removal of the molecular sieve and concentration, the residue was purified by silica gel column chromatography (FL60D (trade name), manufactured by Fuji Silysia Chemical Ltd.) (hexane:ethyl acetate=9:1→4:1→1:1) to obtain a ketone compound (2.2 g).

The ketone compound (2.2 g) was dissolved in 5 mL of methanol, and 2 mL of an ammonia/methanol solution was added thereto, followed by stirring at room temperature overnight. After completion of the reaction and concentration, the residue was purified by silica gel column chromatography (FL60D (trade name), manufactured by Fuji Silysia Chemical Ltd.) (hexane:ethyl acetate=4:1→1:1) to obtain a carboxylic acid derivative (2.5 g).

The carboxylic acid derivative (2.5 g) was dissolved in 100 mL of methanol, and di-tert-butyl dicarbonate (2.7 g) and palladium hydroxide (500 mg) were added, followed by stirring under a hydrogen atmosphere at room temperature for 2 hours. After completion of the reaction, the reaction solution was filtered with celite. A mother liquor was concentrated and the residue was purified by silica gel column chromatography (FL60D (trade name), manufactured by Fuji Silysia Chemical Ltd.) (hexane:ethyl acetate=4:1→1:1)) to obtain an ester compound (2.4 g).

The ester compound (1.9 g) was dissolved in 40 mL of tetrahydrofuran, and lithium borohydride (240 mg) was added thereto at 0° C., followed by stirring at room temperature for 3 hours. After completion of the reaction, an aqueous saturated ammonium chloride solution was added, followed by stirring and then extraction with dichloromethane. The organic layer was dried over magnesium sulfate and then concentrated to obtain an alcohol compound (1.9 g).

The alcohol compound (1.9 g) was dissolved in 25 mL of dimethylformamide, and imidazole (749 mg) and tert-butyldimethylchlorosilane (1.2 g) were added thereto, followed by stirring at room temperature for 2 hours. After completion of the reaction, the reaction solution was poured into an ice-aqueous saturated sodium hydrogen carbonate solution and the solution was extracted with ethyl acetate. The organic layer was washed with an aqueous saturated sodium hydrogen carbonate solution, water and brine, dried over magnesium sulfate and then concentrated. The residue was purified by silica gel column chromatography (FL60D (trade name), manufactured by Fuji Silysia Chemical Ltd.) (hexane:ethyl acetate=4:1)) to obtain a silylated compound (2.0 g).

A Dess-Martin reagent (3.7 g) was suspended in 30 mL of acetonitrile, and a silylated compound (2.0 g) dissolved in 10 mL of acetonitrile was slowly added thereto, followed by stirring at room temperature for 2 hours. After completion of the reaction, ethyl acetate was added, and the solution was poured into an ice-aqueous saturated sodium thio sulfate solution and extracted with ethyl acetate. The organic layer was washed with an aqueous saturated sodium hydrogen carbonate solution, water and brine, dried over magnesium sulfate and then concentrated. The residue was purified by silica gel column chromatography (FL60D (trade name), manufactured by Fuji Silysia Chemical Ltd. (hexane:ethyl acetate=9:1→4:1) to obtain a ketone compound (1.6 g).

Sodium hydride (209 mg) was suspended in 15 mL of tetrahydrofuran, and diethylmethyl phosphonate (1.1 g) was added thereto at 0° C., followed by stirring at 0° C. for 30 minutes. The ketone compound (1.6 g) dissolved in 5 mL of tetrahydrofuran was slowly added, followed by stirring at 0° C. for 1 hour. After completion of the reaction, the reaction solution was poured into an ice-aqueous saturated ammonium chloride solution and the solution was extracted with ethyl acetate. The organic layer was washed with water and brine, dried over magnesium sulfate and then concentrated. The residue was purified by silica gel column chromatography (FL60D (trade name), manufactured by Fuji Silysia Chemical Ltd.) (hexane:ethyl acetate=19:1→9:1→4:1) to obtain a carboxylic acid derivative (1.5 g).

The carboxylic acid derivative (1.9 g) was dissolved in 10 mL of acetonitrile, and nitromethane (1.3 mL) and diazabicycloundecene (3.5 mL) were added thereto, followed by stirring at 75° C. overnight. After completion of the reaction, the reaction solution was poured into an ice-aqueous saturated ammonium chloride solution and the solution was extracted with ethyl acetate. The organic layer was washed with water and brine, dried over magnesium sulfate and then concentrated. The residue was purified by silica gel column chromatography (FL60D (trade name), manufactured by Fuji Silysia Chemical Ltd.) (hexane:ethyl acetate=29:1→9:1) to obtain a nitro compound (1.1 g).

The nitro compound (1.2 g) was dissolved in 40 mL of ethanol and 5 mL of Raney nickel was added thereto, followed by stirring under a hydrogen atmosphere at room temperature for 1.5 hours. After completion of the reaction, the reaction solution was filtered with celite and the filtrate was concentrated. The residue was purified by silica gel column chromatography (FL60D (trade name), manufactured by Fuji Silysia Chemical Ltd.) (ethyl acetate) to obtain a ketone compound (910 mg).

The ketone compound (780 mg) was dissolved in 4 mL of toluene and borane dimethyl sulfide (372 μL) was added thereto, followed by stirring with heating at reflux for 6 hours. After completion of the reaction, an aqueous saturated sodium carbonate solution was slowly added at 0° C. After stirring at room temperature for 30 minutes, the solution was extracted with ethyl acetate. The organic layer was washed with water and brine, dried over magnesium sulfate and then concentrated. The residue was dissolved in 10 mL of methanol and 200 mg of palladium-carbon was added, followed by stirring at room temperature overnight. The mixture was filtered with celite and the filtrate was concentrated. The residue was purified by silica gel column chromatography (FL60D (trade name), manufactured by Fuji Silysia Chemical Ltd.) (hexane:ethyl acetate=1:1→ethyl acetate→ethyl acetate:methanol:ammonia water=8:1:0.2→dichloromethane:methanol:ammonia water=8:1:0.2) to obtain a Spiro compound (486 mg).

The Spiro compound (486 mg) was dissolved in 7 mL of acetonitrile, and triethylamine (265 μL) and benzyl chloroformate (259 mg) were added thereto at 0° C., followed by stirring at 0° C. for 1 hour. After completion of the reaction, the reaction solution was poured into an ice-aqueous saturated ammonium hydrogen carbonate solution and the solution was extracted with ethyl acetate. The organic layer was washed with water and brine, dried over magnesium sulfate and then concentrated. The residue was purified by silica gel column chromatography (FL60D (trade name), manufactured by Fuji Silysia Chemical Ltd.) (hexane:ethyl acetate=9:1→4:1) to obtain a benzyloxycarbonylated compound (593 mg).

The benzyloxycarbonylated compound (593 mg) was dissolved in 1 mL of ethyl acetate and 3 mL of a 4N hydrochloric/ethyl acetate solution was added thereto at 0° C., followed by stirring at room temperature for 2 hours. After completion of the reaction and concentration, the residue was purified by silica gel column chromatography (CHROMATOREX NH (trade name), manufactured by Fuji Silysia Chemical Ltd.) (ethyl acetate→ethyl acetate:methanol=9:1) to obtain an alcohol compound (144 mg).

The alcohol compound (108 mg) was dissolved in 4 mL of methanol and di-tert-butyl dicarbonate (93 mg) was added thereto, followed by stirring at room temperature overnight. After completion of the reaction and concentration, the residue was purified by silica gel column chromatography (FL60D (trade name), manufactured by Fuji Silysia Chemical Ltd.) (ethyl acetate→ethyl acetate:methanol=9:1→ethyl acetate:methanol:ammonia water=8:1:0.2) to obtain a N-tert-butoxycarbonylated compound (207 mg).

The N-tert-butoxycarbonylated compound (207 mg) was dissolved in 4 mL of dimethyl sulfoxide, and triethylamine (149 μL) and a sulfur trioxide-pyridine complex (170 mg) was added thereto, followed by stirring at room temperature for 1 hour. After completion of the reaction, ethyl acetate was added, and the solution was poured into ice water and extracted with ethyl acetate. The organic layer was washed with water and brine, dried over magnesium sulfate and then concentrated. The residue was purified by silica gel column chromatography (hexane:ethyl acetate=5:1) to obtain an aldehyde compound (147 mg).

The aldehyde compound (147 mg) was dissolved in 4 mL of tert-butanol/water (4/1), and 2-methylbutene (170 μL) and sodium dihydrogen phosphate (43 mg) were added thereto and sodium chlorite (141 mg) was added at 0° C., followed by stirring at room temperature for 1 hour. After completion of the reaction, an aqueous 5% citric acid solution was added, and the solution was extracted with ethyl acetate. The organic layer was washed with water and brine, dried over magnesium sulfate and then concentrated to obtain a carboxylic acid derivative. This carboxylic acid derivative was dissolved in methanol, trimethylsilyldiazomethane was added at 0° C. and then concentrated. The residue was purified by silica gel column chromatography (FL60D (trade name), manufactured by Fuji Silysia Chemical Ltd.) (hexane:ethyl acetate=9:1→4:1→2:1) to obtain a carboxylic acid derivative (122 mg).

The carboxylic acid derivative (122 mg) was dissolved in 1 mL of methanol and 2 mL of a 10%-hydrochloric acid/methanol solution was added thereto, followed by stirring at room temperature overnight. After completion of the reaction and concentration, the residue was purified by silica gel column chromatography (ethyl acetate→ethyl acetate:methanol=9:1) to obtain an amino compound (112 mg).

The amino compound (129 mg) was dissolved in 4 mL of acetonitrile, and 1-iodo-2-methylpropane (89 μL) and potassium carbonate (81 mg) were added thereto, followed by stirring with heating at reflux for 28 hours. After completion of the reaction, the reaction solution was poured into ice water and the solution was extracted with ethyl acetate. The organic layer was washed with water and brine, dried over magnesium sulfate and then concentrated. The residue was purified by silica gel column chromatography (FL60D (trade name), manufactured by Fuji Silysia Chemical Ltd.) (hexane:ethyl acetate=2:1 ethyl acetate:methanol:ammonia water=8:1:0.2) to obtain an N-alkyl compound (53 mg).

The N-alkyl compound (53 mg) was dissolved in 5 mL of methanol and 10 mg of palladium-carbon was added thereto, followed by stirring under a hydrogen atmosphere at room temperature for 2 hours. After completion of the reaction, the reaction solution was filtered with celite and the filtrate was concentrated. The residue was purified by silica gel column chromatography (CHROMATOREX NH (trade name), manufactured by Fuji Silysia Chemical Ltd.) (ethyl acetate→ethyl acetate:methanol=9:1) to obtain an amino compound (26 mg).

4-{[bis(1H-imidazol-2-ylmethyl)amino]methyl}benzaldehyde (International Publication WO 2007/058322 pamphlet, Example 28; 39 mg) was dissolved in 3 mL of acetonitrile and 3 droplets of acetic acid were added thereto, and the amino compound (26 mg) and sodium triacetoxyborohydride (28 mg) were added, followed by stirring at room temperature overnight. Furthermore, 4-{[bis(1H-imidazol-2-ylmethyl)amino]methyl}benzaldehyde (9 mg) and sodium triacetoxyborohydride (6 mg) were added thereto, followed by stirring at room temperature for 4 hours. After completion of the reaction, the reaction solution was poured into an ice-aqueous saturated sodium carbonate solution and the solution was extracted with ethyl acetate. The organic layer was washed with an aqueous saturated sodium hydrogen carbonate solution, water and brine, dried over magnesium sulfate and then concentrated. The residue was purified by silica gel column chromatography (FL60D (trade name), manufactured by Fuji Silysia Chemical Ltd.) (ethyl acetate:methanol=9:1→ethyl acetate:methanol:ammonia water=8:1:0.2) to obtain a carboxylic acid derivative (46 mg).

The carboxylic acid derivative (46 mg) was dissolved in 2 mL of methanol and 2N sodium hydroxide (86 μL) was added thereto, followed by stirring at room temperature for 3 days. Furthermore, 2N sodium hydroxide (86 μL) was added thereto, followed by stirring at 50° C. for 4 hours, then at 70° C. for 4 hours. Furthermore, 5N sodium hydroxide (86 μL) was added thereto, followed by stirring at 70° C. overnight. After completion of the reaction and concentration, 5N hydrochloric acid was added to the residue until pH 1 to 2 and the residue was concentrated. Ethanol was added to the residue and precipitated NaCl was filtered, and then the filtrate was concentrated. The residue was purified by silica gel column chromatography (CHROMATOREX NH (trade name), manufactured by Fuji Silysia Chemical Ltd.) (ethyl acetate:methanol=9:1 dichloromethane:methanol=4:1 dichloromethane:methanol:ammonia water=4:1:0.2) to obtain the title compound (36 mg) having the following physical properties.

TLC: Rf 0.42 (chloroform:methanol: 28% ammonia water=40:10:2);

NMR (CDCl$_3$): δ 0.97 (d, J=6.77 Hz, 3H), 1.06 (d, J=6.77 Hz, 3H), 1.69 (t, J=6.77 Hz, 2H), 1.76-1.96 (m, 3H), 2.04-2.21 (m, 2H), 2.50-2.90 (m, 6H), 3.03 (dd, J=12.53, 9.42 Hz, 1H), 3.29-3.36 (m, 1H), 3.51 (s, 2H), 3.50-3.58 (m, 1H), 3.64 (s, 6H), 7.00 (s, 4H), 7.23-7.40 (m, 4H)

Reference Example 7

2-(4-{[bis(1H-imidazol-2-ylmethyl)amino]methyl}benzyl)-8-(1-ethylpropyl)-2,8-diazaspiro[4.5]decane-1-carboxylic acid Under an argon atmosphere at −78° C., 1-tert-butyl 4-ethylpiperidine-1,4-dicarboxylate (CAS Registry Number: 142851-03-4; 110 mL) was dissolved in 150 mL of anhydrous tetrahydrofuran and 22.4 mL of lithium diisopropylamide was added dropwise. After stirring as it is for 1 hour, 3.44 mL of allyl bromide was added dropwise, followed by stirring for 15 hours while raising the temperature to room temperature. The solution was diluted by adding water and extracted three times with ethyl acetate. The organic layers were combined, washed with saturated brine and then dried over anhydrous magnesium sulfate, and the solvent was distilled off. The residue was purified by silica gel column chromatography to obtain a carboxylic acid derivative (8.67 g).

Under an argon atmosphere at −78° C., a carboxylic acid derivative (4.86 g) was dissolved in methanol (30 mL) and an ozone gas was bubbled for 1 hour while stirring. After argon bubbling for 30 minutes, dimethyl sulfide (2.39 mL) was added, followed by stirring for 15 hours while returning the temperature to room temperature. The solvent was distilled off and the solution was diluted with water and extracted three times with ethyl acetate. The organic layers were combined, washed with saturated brine and then dried over anhydrous magnesium sulfate, the solvent was distilled off. The residue was purified by silica gel column chromatography to obtain a ketone compound (3.78 g).

Under an argon atmosphere at room temperature, the ketone compound (3.77 g) and benzylamine (1.35 mL) were dissolved in N,N-dimethylformamide (12.6 mL) and acetic acid (1.26 mL) was added, followed by stirring. Sodium triacetoxyborohydride (4.01 g) was added, followed by stirring for 3 hours. After raising the temperature to 40° C., the mixture was stirred for 18 hours. After dilution with water, the solution was made basic by adding sodium carbonate and extracted three times with ethyl acetate. The organic layers were combined, washed with saturated brine and then dried over anhydrous sodium sulfate, and the solvent was distilled off. The residue was purified by silica gel column chromatography to obtain a ketone compound (2.88 g).

Under an argon atmosphere at −40° C., the ketone compound (591 mg) was dissolved in tetrahydrofuran (10 mL) and hydrogenated diisobutyl aluminum (1M tetrahydrofuran solution) (2.26 mL) was added dropwise. After stirring at the same temperature for 2 hours, an aqueous solution (2 mL) of potassium cyanide (336 mg) was added, followed by stirring for 30 minutes while gradually raising the temperature at room temperature. After dilution with water, the solution was extracted three times with ethyl acetate. The organic layers were combined, washed with saturated brine and then dried over anhydrous sodium sulfate, and the solvent was distilled off. The residue was purified by silica gel column chromatography to obtain a cyanide (190 mg).

Under an argon atmosphere at −78° C., lithium diisopropylamide (2M heptane/tetrahydrofuran/ethylbenzene solution) (0.429 mL) was added to hexamethylphosphoric acid triamide (0.149 mL), followed by stirring for 5 minutes and further dropwise addition of a solution prepared by dissolving the cyanide (152 mg) in 5 mL of tetrahydrofuran. After stirring for 5 minutes, ethyl chloroformate (81.6 μL) was added and stirred for 1.5 hours. After dilution with water, the solution was extracted three times with ethyl acetate. The organic layers were combined, washed with saturated brine and then dried over anhydrous sodium sulfate, and the solvent was distilled off. The residue was purified by silica gel column chromatography to obtain a carboxylic acid derivative (147 mg).

At room temperature, the carboxylic acid derivative (147 mg) was dissolved in ethanol (6 mL) and water (3 mL), and sodium borohydride (130 mg) was added thereto, followed by stirring for 5 hours. After dilution with water, the solution was extracted three times with dichloromethane. The organic layers were combined, washed with saturated brine and then dried over anhydrous magnesium sulfate, and the solvent was distilled off. The residue was purified by silica gel column chromatography to obtain an alcohol compound (95.0 mg).

At room temperature, the alcohol compound (146 mg) was dissolved in ethanol (5 mL) and palladium hydroxide carbon (50 mg) was added, and the atmosphere in the reaction system was replaced by a hydrogen gas, followed by stirring at 60° C. for 3 hours. After filtration with celite, the solvent was distilled off from the filtrate to obtain a carboxylic acid derivative (100 mg).

At room temperature, the carboxylic acid derivative (100 mg) was dissolved in tetrahydrofuran (3 mL) and an aqueous sodium carbonate solution (3 mL), and benzyl chloroformate (98.6 μL) was added, followed by stirring for 3 hours. After dilution with water, the solution was extracted three times with dichloromethane. The organic layers were combined, washed with saturated brine and then dried over anhydrous magnesium sulfate, and the solvent was distilled off. The residue was purified by silica gel column chromatography to obtain a carboxylic acid derivative (108.9 mg).

Under an argon atmosphere at 0° C., the carboxylic acid derivative (108 mg) was dissolved in dichloromethane (2 mL), and dimethyl sulfoxide (74.7 μL) and triethanolamine (149 μL) were added. After the addition of a sulfur trioxide-pyridine complex (84.9 mg), the temperature was raised to room temperature, followed by stirring for 24 hours. After dilution with water, the solution was extracted three times with dichloromethane. The organic layers were combined, washed with saturated brine and then dried over anhydrous magnesium sulfate, and the solvent was distilled off. The residue was purified by silica gel column chromatography to obtain an aldehyde compound (75.0 mg).

At room temperature, the aldehyde compound (75.0 mg) was dissolved in a solution (5 mL) (tert-butanol:water=5:1), and 2-methyl-2-butene (0.119 mL), sodium dihydrogen phosphate (44.6 mg) and sodium chlorite (50.6 mg) were sequentially added, followed by stirring for 2 hours and 15 minutes. After dilution with water, the solution was extracted three times with ethyl acetate. The organic layers were combined, washed with saturated brine and then dried over anhydrous magnesium sulfate, and the solvent was distilled off. At room temperature, methanol (5 mL) was added and trimethylsilyldiazomethane (2M hexane solution) (22 mL) was added. After stirring for 1 minute, the solvent was distilled off. The residue was purified by silica gel column chromatography to obtain a carboxylic acid derivative (63.0 mg).

At room temperature, the carboxylic acid derivative (63.0 mg) was dissolved in ethanol (5 mL) and palladium hydroxide carbon (30 mg) was added, and the atmosphere in the reaction system was replaced by a hydrogen gas, followed by stirring at room temperature for 30 minutes. After filtration with celite, the solvent was distilled off from the filtrate to obtain an amine compound (53.0 mg).

At room temperature, the amine compound (53.0 mg) and the compound (111.6 mg) obtained in Example 25 were dissolved in methanol (1 mL) and water (0.1 mL), and 2-picolineborane (31.2 mg) was added, followed by stirring for 4 hours. Thereafter, 0.5N hydrochloric acid (2 mL) was added, followed by further stirring for 30 minutes. After dilution with water, the solution was extracted three times with dichloromethane. The organic layers were combined, washed with saturated brine and then dried over anhydrous magnesium sulfate, and the solvent was distilled off. The residue was purified by silica gel column chromatography to obtain a carboxylic acid derivative (78.6 mg).

At 0° C., the carboxylic acid derivative (78.6 mg) was dissolved in methanol (0.98 mL) and 10% sulfuric acid (0.49 mL) was added, followed by stirring for 18 hours while raising the temperature to room temperature. After neutralizing with an aqueous sodium carbonate solution, the solution was extracted three times with dichloromethane. The organic layers were combined, washed with saturated brine and then dried over anhydrous sodium sulfate, and the solvent was distilled off. The residue was purified by silica gel column chromatography to obtain an amine compound (54.9 mg).

Under an argon atmosphere at room temperature, the amine compound (54.9 mg), 3-pentanone (165 μL) and titanium ethoxide (49.0 μL) were mixed, followed by stirring at 50° C. for 1 hour. After returning the temperature to room temperature, tetrahydrofuran (2 mL) was added and further sodium triacetoxyborohydride (49.6 mg) was added, followed by stirring for 1 hour. An aqueous sodium carbonate solution and dichloromethane were added, followed by stirring and further filtration with celite. The oil layer was separated from the filtrate and extracted twice with dichloromethane from the aqueous layer. The organic layers were combined, washed with saturated brine and then dried over anhydrous sodium sulfate, and the solvent was distilled off. The residue was purified by silica gel column chromatography to obtain a carboxylic acid derivative (31.9 mg).

At room temperature, a 10% hydrochloric acid methanol solution (1 mL) was added to the carboxylic acid derivative (31.9 mg), followed by stirring at 40° C. for 15 hours. The solvent was distilled off, dilution with water, and then the solution was washed once with ethyl acetate. The aqueous layer was made basic by adding sodium carbonate and then extracted three times with dichloromethane. The organic layers were combined, washed with saturated brine, dried over anhydrous sodium sulfate, and then the solvent was distilled off. The residue was purified by silica gel column chromatography to obtain an amine compound (18.0 mg).

At room temperature, the amine compound (18.0 mg) was dissolved in ethanol (0.1 mL) and 2N sodium hydroxide (0.1 mL) was added, followed by stirring at 70° C. for 24 hours. Thereafter, ethanol (0.05 mL) and 2N sodium hydroxide (0.2 mL) were added, followed by stirring at 80° C. for 23 hours. 2N hydrochloric acid (0.3 mL) was added and the solvent was distilled off. The residue was purified twice by silica gel column chromatography to obtain the title compound (13.0 mg) having the following physical properties.

TLC: Rf 0.43 (dichloromethane:methanol: 28% ammonia water=80:20:4)

NMR (CD$_3$OD): δ 0.97 (t, J=7.3 Hz, 6H) 1.41-1.65 (m, 4H) 1.65-1.96 (m, 6H) 2.09-2.30 (m, 1H) 2.46-2.85 (m, 4H) 2.89-3.20 (m, 3H) 3.51 (s, 2H) 3.53-3.78 (m, 1H) 3.64 (s, 4H) 4.13 (d, J=12.6 Hz, 1H) 6.98 (s, 4H) 7.23-7.41 (m, 4H)

BIOLOGICAL EXAMPLES

HIV Infection Inhibitory Activity

1. HIV Infection Inhibitory Test Using PBMC

Human PBMC (peripheral blood mononuclear cells) was isolated from HIV-negative healthy persons and subjected to stimulated culture in the presence of PHA (Phytohemagulutinin) and IL-2. Stimulated PBMC was inoculated in each of 96-well microplates and X$^4$-HIV-1 strains (for example, HIV-1NL4.3 strains) were exposed in the co-presence of a test compound. After culturing for 7 days, a reverse transcriptase activity of HIV-1 in the culture supernatant was measured and an inhibitory ratio (%) of the test compound was calculated by the following calculation formula, and a concentration (IC$_{90}$ value) showing a 90% inhibitory ratio was determined.

Inhibition={(Et−Ec)/Et}×100     [Equation 1]

Et: reverse transcriptase activity value in the absence of a test compound

Ec: reverse transcriptase activity value in the presence of a test compound

For example, the IC$_{90}$ value of the compound of Example 5(5) was 0.27 nM, that of the compound of Example 32(6) was 0.27 nM, and that of the compound of Example 32(7) was 0.23 nM.

2. Blood Kinetic Test

A test compound was weighed, dissolved in WellSolve (trade name; manufactured by Celeste Corporation)/water/physiological saline=1/9/10 which was heated at 60° C. and adjusted to 20 mg/mL. Thereafter, the test compound was diluted by 10 times with distilled water for injection, and further diluted by 2 times with physiological saline. Then, intravenous administration was performed by rapid single administration of an intravenously administered solution (1 mg/kg) from the tail vein of Crl:CD(SD) Rat (male, manufactured by CHARLES RIVER LABORATORIES JAPAN, INC). The administration is conducted under fasting conditions; water is freely ingested. A 0.35 mL blood sample is taken from cervical vein by using Heparinized Syringe at 5 minutes, 15 minutes, 30 minutes, 1 hour, 2 hours, 4 hours, 6 hours, 8 hours, and 24 hours after administration. The obtained blood is stored in ice, and after centrifugation at 12,000 rpm for 5 minutes, blood plasma is fractionated. An internal standard solution (100 μL) and acetonitrile (2 mL) was added to 100 μL of plasma, followed by stirring and further centrifugation at 2,500 rpm for 10 minutes. The supernatant was desiccated by a centrifugal thickener and then 150 μL of an aqueous 67% dimethyl sulfoxide solution was added to the residue thereby dissolving again the residue, and 20 μL of the resultant solution was analyzed by LC/MS/MS.

Analysis by LC/MS/MS was carried out under the following conditions.

[LC Conditions]

Measurement device: Waters 2795 (manufactured by Waters Corporation)

Analytical column: Unison UK-C18, 3.0 μm particle size, 2.0 mm×30 mm (manufactured by Imtakt Corporation)

Analytical column temperature: Room temperature

Flow rate: 200 μL/min

Moving bed: 5 mM IPC-PFAA-7 solution/acetonitrile (9/1→1/9)

[MS/MS Conditions]

Measurement device: Quatro micro API (manufactured by Micromass Communications Inc.)

Method for ionization: ES+

Capillary electric potential: 3.30 kV

Source temperature: 120° C.

Desolvation temperature: 350° C.

Multiplier: 650 V

The monitor ion which was suitable for each sample was selected. For example, in the compound of Example 5(5), a monitor ion having a M/Z value of 374.30 was used as the monitor ion.

A curve of the compound concentration in plasma versus the time of each compound was adapted to a 1 or 2 compartment model using pharmacokinetic analysis software WinNonlin (trade name) (ver4.0.1, Pharsight Corporation).

3. Evaluation of Compounds

As a result of a clinical trial against HIV-infected patients harboring X4-tropic virus of AMD 11070 as a CXCR4 inhibitor, efficacy was confirmed when the blood concentration maintains the concentration or more, which exhibits 90% of an inhibitory ratio, determined by an HIV infection inhibitory test using PBMC (Clinical Infectious Diseases, 48, 798 (2009)). As a result, considering that the compound capable of maintaining the blood concentration of an IC$_{90}$ value or more for a long period of time, determined by the above test 1 after administering the compound in the above test 2, can exhibit a persistent and strong HIV infection inhibitory activity, time (T$_{90}$) to maintain the IC$_{90}$ value determined by the above test 1 was determined by the formula of a curve of the compound concentration in plasma versus the time determined by the above test 2. The results are shown in Table 1.

TABLE 1

| | Compound | T$_{90}$ (h) |
|---|---|---|
| a | [chemical structure] | 91 |

TABLE 1-continued

| | Compound | $T_{90}$ (h) |
|---|---|---|
| b | | 12 |
| c | | 7 |
| d | | 5 |
| e | | 17 |
| f | | 6 |

TABLE 1-continued

| Compound | $T_{90}$ (h) |
|---|---|
| g [structure] | 2 |
| h [structure] | 1.2 |
| i [structure] | 3 |
| j [structure] | <1 |
| k [structure] | 14 |
| l [structure] | 4 |

TABLE 1-continued

| Compound | $T_{90}$ (h) |
|---|---|
| m (structure) | 4 |

In the present invention, as shown in formula (I), it is important to have a carboxyl group at the 3-position of 2,8-diazaspiro[4.5]decane and to substitute $R^3$ on the nitrogen atom at the 8-position.

In Table 1, the compound (a) (the compound of Example 5(5)) is one of the compounds represented by formula (I) of the present invention. The compounds (b) (the compound of Reference Example 1), (c) (the compound of Reference Example 4), (d) (the compound of Reference Example 2), (e) (the compound of Reference Example 5), (f) (the compound of Reference Example 7), (g) (the compound of Reference Example 6) and (h) (the compound of Reference Example 3) are not specifically described in the aforementioned Patent Documents 1 to 7, and are described for comparison as the compound having a chemical structure similar to that of the compound (a) of the present invention. Also, the compound (i) is a known compound described specifically in Example 65-1 of the aforementioned Patent Document 8, the compound (j) is a known compound described specifically in Example 49(19) of the aforementioned Patent Document 3, the compound (k) is a known compound described specifically in Example 29(49) of the aforementioned Patent Document 5, the compound (l) is a known compound described specifically in Example 9 of the aforementioned Patent Document 6, and the compound (m) is a known compound described specifically in Example 25(2) of the aforementioned Patent Document 7.

As shown in Table 1, the compound (a) of the present invention maintained the blood concentration of $IC_{90}$ value or more for 91 hours after intravenous administration. To the contrary, in the compound having no carboxyl group in the molecule like the compound (b), and the compound having an amidated carboxyl group like the compound (c), the time maintained the blood concentration of $IC_{90}$ value or more for was only 12 hours or less after intravenous administration. In the compound having a carboxyl group in the molecule but having no 2,8-diazaspiro[4.5]decane like the compound (i), and the compounds in which a carboxyl group is bound to that other than 2,8-diazaspiro[4.5]decane like compounds (d), (l), (m) and (k) maintained the blood concentration of $IC_{90}$ value or more for 14 hours or less after intravenous administration. Furthermore, the compounds in which a carboxyl group is bound to the site of 2,8-diazaspiro[4.5]decane, which is different from that of the compound (a), like the compounds (e), (f), (g) and (h) also maintained the blood concentration of $IC_{90}$ value or more within 17 hours after intravenous administration. As described above, it is necessary that the carboxyl group is bound to the 3-position of 2,8-diazaspiro[4.5]decane. But, in the compound in which the carboxyl group is bound to the 3-position of 2,8-diazaspiro[4.5]decane and $R^3$ is substituted on the nitrogen atom at the 2-position, like the compound (J) maintained the blood concentration of $IC_{90}$ value or more within 1 hour after intravenous administration. In other words, only the compound of the present application, which has a carboxyl group at the 3-position of 2,8-diazaspiro[4.5]decane, and $R^3$ substituted on the nitrogen atom at the 8-position, maintained the blood concentration of $IC_{90}$ value or more for 3 days or more after intravenous administration, whereas, other compounds could not maintain the blood concentration of $IC_{90}$ value or more for only 1 day after intravenous administration.

From these results, it is considered that it is impossible to achieve the object of the present invention even when the carboxyl group is included in the molecule. Like the compound represented by formula (I) of the present invention, it could not be entirely expected to obtain such a useful effect by introducing a carboxyl group into the position where a specific spatial relation with a basic nitrogen atom in the molecule is maintained.

As described above, the compound (a) of the present invention is a compound which persists an effective blood concentration for a long period of time and also has a strong HIV infection inhibitory activity, and is a very high-safety compound exhibiting a reduced risk of side effects (for example, phospholipidosis induction activity), as described hereinafter.

<Activity>

Both of T cell-directed (X4) HIV-1 and SDF-1 bind to CXCR4 and therefore CXCR4 binding sites at both of HIV-side and SDF-1-side as well as SDF-1- and HIV-binding sites at the CXCR4 side may presumably have any common characteristics. Thus, in order to find a compound inhibiting absorption of HIV viruses to a cell namely a different mechanism from those of pre-existing anti-AIDS drugs (reverse transcriptase inhibitors and protease inhibitors), an assay system using an endogenous ligand for CXCR4, SDF-1 instead of HIV may be available.

Specifically, as a system of screening a compound that inhibits the binding between SDF-1 and CXCR4, for example a system of measuring the binding between iodine-labeled SDF-1 and a human T cell strain in which CXCR4 is known to be expressed is operable.

1. Study for Inhibition of Binding Human SDF-1 to CEM Cells

To human T cell strain CEM cells in a binding buffer (containing 2-[4-(2-Hydroxyethyl)-1-piperadinyl]ethansulfonic acid; HEPES and BSA), the test compound and $^{125}$I-SDF-1 (PerkinElmer) were added and the mixture was incubated at 4° C. for 60 minutes. The reacted CEM cells were rapidly filtrated with a GF/B membrane filter plate (Packard) to adsorb. The plate was washed with phosphate buffered saline (hereinafter abbreviated to PBS) three times and then dried. Microscint+20 (Packard) was added thereto. An amount of the radioactivity bound to the CEM cells was measured using Top Count (Packard) and inhibition ratio (%) of the test compound was calculated according to the following equation:

$$\text{Inhibition} = \{(Et-Ea)/(Et-Ec)\} \times 100 \quad \text{[Equation 2]}$$

Et: Amount of radioactivity when the test compound is not added,
Ec: Amount of radioactivity when non-radioactive SDF-1 (Pepro Tech) is added in an amount of 1,000 times as much as $^{125}$I-SDF-1 as a test compound, and
Ea: Amount of radioactivity when the test compound is added.

All compounds of the present invention shown in Examples exhibited inhibition ratio of 50% or more in a concentration of 10 μM. For example, the concentration showing 50% of an inhibition ratio of the compound of Example 5(5) was 3 nM, that of the compound of Example 32(6) was 3.3 nM, that of the compound of Example 32(7) was 3.2 nM, that of the compound of Example 37(6) was 11.3 nM, and that of the compound of Example 37(7) was 11.1 nM.

<Toxicity>

International Publication WO 2007/0058322 pamphlet (Patent Document 5) discloses that, in the method described in Test Example 4 of Biological Example, since the treatment concentration of the compound described in the Patent Document was 50 μM and the compound was determined as negative, the compound is evaluated as a safe compound having a low phospholipidosis induction activity. However, it has been found that even in case of the compound which was evaluated as negative by the method and determined as safe, vacuolation of cytoplasm as an indicator of phospholipidosis is recognized when administered to animals, for example, rats and it is actually a compound having a problem with salty. Thus, the present inventors newly constructed an evaluation system under more severe conditions and carried out the evaluation. As a result, it has been found that the compound determined as negative in the maximum treatment concentration of this system is a compound with no risk of phospholipidosis even in case of the system using animals.

1. Phospholipid Accumulation Measurement

100 L/well as required (1 dose 2 wells) of cell suspension of CHL/IU (cell line derived from a Chinese hamster lung) ($7 \times 10^4$ cells/mL) prepared by MEM (minimum essential medium) culture medium was added to a 96-well plate (96-well clear-bottom plate), and cultured for about 24 hours. After culture, the supernatant of the 96-well plate was removed, and the 100 μL/well compounds of each concentration dissolved and suspended in a minimum essential medium (MEM) including 25 μM nitrobenzoxazole dipalmitoyl phosphatidylethanolamine (NBD-PE) (hereinafter abbreviated to a NPD-PE medium) were added and treated for about 48 hours. The treatment concentrations of each compound were set to be 5, 50, 100, 200 and 400 μM. The positive control substance was set to be amiodarone hydrochloride, and the treatment concentrations were set to be 1.25, 2.5, 5, 10 and 20 μM. In addition, 5-well untreated controls (only MEM) and 5-well NBD-PE controls (made by means of adding a 1/100 amount of DMSO to the NBD-PE culture medium) were set per compound, and cultured in the same manner. After finishing the culture, the cultures were washed twice with PBS (−) 100 μL/well, and the MEM (100 μL) was added to all of the treatment wells including two empty wells for WST-1 background controls and cultured for about half an hour. The fluorescence intensities of each well were measured by using a microplate reader (manufactured by Molecular Devices Inc., SPECTRA max M2; the excitation wavelength 485 nm/fluorescence wavelength 535 nm).

2. Analysis

Using the average values of each dose×2 wells, a phospholipid increase rate (%) to the NBD-PE control was calculated by using the following calculating formula:

$$\begin{aligned}
&\text{Rate of increase of phospholipid accumulation} \\
&(\%) = 100 \times \{(\text{test substance fluorescence intensity} - \text{non-treated control fluorescence intensity})/ \\
&(\text{NBD-PE control fluorescence intensity} - \text{non-treated control fluorescence intensity})\}
\end{aligned}$$

3. Cytotoxicity Test 96-well plate measured in the phospholipid accumulation measurement was measured by means of Plate Reader (manufactured by Molecular Devices Inc., SPECTRA max M2) with the main wavelength of 450 nm and the correct wavelength of 690 nm to calculate a Pre value. An amount of 5 μL/well of Premix WST-1 was added to each of the 96-well plates by which Pre measurement was conducted. After culture for 2 to 4 hours, the 96-well plate was measured as well as the Pre measurement to calculate an Aft value. Then, the background control value was subtracted from the each measured value. A value which was calculated by subtracting the Pre value from the Aft value was used, then the cell growth rate (%) was calculated by using the following calculating formula:

$$\text{Cell growth rate (\%)} = 100 \times \{(\text{test substance OD})/(\text{NBD-PE control OD})\}$$

4. Determination

A test dose that indicated value of 25% or more of the maximum phospholipid accumulation increase rate of amiodarone which was the positive control was determined as positive. In addition, the dose whose cell growth rate was equal to or less than 50% in the cytotoxicity test was not used for determination of existence or nonexistence of a phospholipidosis inductive effect.

The compounds of Example 5(5), Example 32(6), Example 32(7), Example 37(6) and Example 37(7) were determined as negative even at 400 μM, and they have found to be compounds with no phospholipidosis induction activity.

FORMULATION EXAMPLES

Formulation Example 1

(3S)-2-(4-{[bis(1H-imidazol-2-ylmethyl)amino]methyl}benzyl)-8-(1-ethylpropyl)-2,8-diazaspiro[4.5]decane-3-carboxylic acid (100 g), calcium carboxymethyl cellulose (disintegrant, 20.0 g), magnesium stearate (lubricant, 10.0 g) and microcrystalline cellulose (870 g) were mixed by a conventional method and then compressed to obtain 10,000 tablets each containing 20 mg of an active ingredient per tablet.

Formulation Example 2

(3S)-2-(4-{[bis(1H-imidazol-2-ylmethyl)amino]methyl}benzyl)-8-(1-ethylpropyl)-2,8-diazaspiro[4.5]decane-3-carboxylic acid (100 g), mannitol (2 kg) and distilled water (50 L) were mixed by a conventional method, filtered with a dust filter, and then each ampoule was filled with 5 mL of the obtained mixture and subjected to heat sterilization in an autoclave to obtain 10,000 ampoules each containing 10 mg of an active ingredient.

INDUSTRIAL APPLICABILITY

The compound of the present invention has an antagonistic activity against CXCR4 and is therefore useful as a preventive and/or therapeutic agent for CXCR4-mediated diseases or cancerous diseases. Examples of CXCR4-mediated diseases include inflammatory and immune diseases, allergic diseases, infections (for example, human immunodeficiency virus (HIV) infection), diseases associated with HIV infection (for example, acquired immunodeficiency syndrome (AIDS)), cancer, cancer metastasis, psychoneurotic diseases, cardiovascular diseases, metabolic diseases and the like. Furthermore, the compound of the present invention is a very high-safety compound exhibiting a highly reduced risk of side effects (for example, phospholipidosis induction activity), and is therefore useful as pharmaceuticals.

The invention claimed is:

1. A compound represented by formula (I):

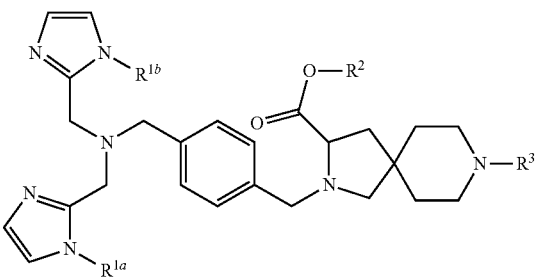

(I)

wherein $R^{1a}$ and $R^{1b}$ each independently represents a hydrogen atom or a C1-4 alkyl group, $R^3$ represents a C3-8 branched-chain alkyl group or a C5-6 cycloalkyl group, and $R^2$ represents hydrogen atom or a C1-4 alkyl group, a salt thereof, an N-oxide thereof, or a solvate thereof.

2. The compound according to claim 1, wherein $R^2$ is a hydrogen atom.

3. The compound according to claim 1, wherein $R^{1a}$ is a hydrogen atom, and also $R^{1b}$ is a hydrogen atom or a methyl group.

4. The compound according to claim 1, wherein $R^3$ is a 1-ethylpropyl, 2,2-dimethylpropyl, 2-methylpropyl or cyclohexyl group.

5. The compound according to claim 1, which is:
  (1) 2-(4-{[bis(1H-imidazol-2-ylmethyl)amino]methyl}benzyl)-8-(1-ethylpropyl)-2,8-diazaspiro[4.5]decane-3-carboxylic acid,
  (2) 8-(1-ethylpropyl)-2-[4-({(1H-imidazol-2-ylmethyl)[(1-methyl-1H-imidazol-2-yl)methyl]amino}methyl)benzyl]-2,8-diazaspiro[4.5]decane-3-carboxylic acid,
  (3) (3R)-8-(1-ethylpropyl)-2-[4-({(1H-imidazol-2-ylmethyl)[(1-methyl-1H-imidazol-2-yl)methyl]amino}methyl)benzyl]-2,8-diazaspiro[4.5]decane-3-carboxylic acid,
  (4) (3S)-8-(1-ethylpropyl)-2-[4-({(1H-imidazol-2-ylmethyl)[(1-methyl-1H-imidazol-2-yl)methyl]amino}methyl)benzyl]-2,8-diazaspiro[4.5]decane-3-carboxylic acid,
  (5) (3R)-2-(4-{[bis(1H-imidazol-2-ylmethyl)amino]methyl}benzyl)-8-(1-ethylpropyl)-2,8-diazaspiro[4.5]decane-3-carboxylic acid, or
  (6) (3S)-2-(4-{[bis(1H-imidazol-2-ylmethyl)amino]methyl}benzyl)-8-(1-ethylpropyl)-2,8-diazaspiro[4.5]decane-3-carboxylic acid.

6. A pharmaceutical composition comprising the compound represented by formula (I) according to claim 1, a salt thereof, an N-oxide thereof or a solvate thereof.

7. The pharmaceutical composition according to claim 6, which is an CXCR4 antagonist.

* * * * *